US012799101B2

(12) United States Patent
Lu

(10) Patent No.: US 12,799,101 B2
(45) Date of Patent: Nov. 17, 2026

(54) JAK INHIBITOR COMPOUND AND USE THEREOF

(71) Applicant: Liang Lu, Shanghai (CN)

(72) Inventor: Liang Lu, Shanghai (CN)

( * ) Notice: Subject to any disclaimer, the term of this patent is extended or adjusted under 35 U.S.C. 154(b) by 1130 days.

(21) Appl. No.: 17/852,990

(22) Filed: Jun. 29, 2022

(65) Prior Publication Data

US 2022/0388992 A1 Dec. 8, 2022

Related U.S. Application Data

(63) Continuation of application No. PCT/CN2020/141251, filed on Dec. 30, 2020.

(30) Foreign Application Priority Data

Dec. 30, 2019 (CN) ........................ 201911394671.X

(51) Int. Cl.

| | |
|---|---|
| ***C07D 403/14*** | (2006.01) |
| ***A61K 31/4178*** | (2006.01) |
| ***A61K 31/437*** | (2006.01) |
| ***A61K 31/439*** | (2006.01) |
| ***A61K 31/4439*** | (2006.01) |
| ***A61K 31/454*** | (2006.01) |
| ***A61K 31/496*** | (2006.01) |
| ***A61K 31/497*** | (2006.01) |
| ***A61K 31/5377*** | (2006.01) |
| ***A61P 1/00*** | (2006.01) |
| ***A61P 3/10*** | (2006.01) |
| ***A61P 11/00*** | (2006.01) |
| ***A61P 11/06*** | (2006.01) |
| ***A61P 17/00*** | (2006.01) |
| ***A61P 19/02*** | (2006.01) |
| ***A61P 25/00*** | (2006.01) |
| ***A61P 27/02*** | (2006.01) |
| ***A61P 29/00*** | (2006.01) |
| ***A61P 35/00*** | (2006.01) |
| ***A61P 37/02*** | (2006.01) |
| ***A61P 37/06*** | (2006.01) |
| ***C07D 401/14*** | (2006.01) |
| ***C07D 403/04*** | (2006.01) |
| ***C07D 405/14*** | (2006.01) |
| ***C07D 471/04*** | (2006.01) |
| ***C07D 471/08*** | (2006.01) |

(52) U.S. Cl.

CPC ......... *C07D 403/14* (2013.01); *C07D 401/14* (2013.01); *C07D 403/04* (2013.01); *C07D 405/14* (2013.01); *C07D 471/08* (2013.01)

(58) Field of Classification Search

CPC .. C07D 403/14; C07D 401/14; C07D 403/04; C07D 405/14; C07D 471/08

See application file for complete search history.

(56) References Cited

U.S. PATENT DOCUMENTS

| | | | | |
|---|---|---|---|---|
| 6,313,129 | B1 | 11/2001 | Uckun et al. | |
| 2005/0090529 | A1 | 4/2005 | McAlpine et al. | |
| 2013/0029968 | A1 | 1/2013 | Coe et al. | |
| 2022/0073524 | A1 * | 3/2022 | Lu ............................ | A61P 1/00 |

FOREIGN PATENT DOCUMENTS

| | | | |
|---|---|---|---|
| CN | 105566321 | A | 5/2016 |
| CN | 106432246 | A | 2/2017 |
| CN | 106459048 | A | 2/2017 |
| CN | 106478607 | A | 3/2017 |
| CN | 106831779 | A | 6/2017 |
| CN | 108349972 | A | 7/2018 |
| CN | 109867676 | A | 6/2019 |

(Continued)

OTHER PUBLICATIONS

Chagas, C. M., Moss, S. & Alisaraie, L. Int. J. Pharma. 2018, 549, 133-149 (Year: 2018).*

(Continued)

*Primary Examiner* — Clinton A Brooks
*Assistant Examiner* — Kendall Nicole Heitmeier
(74) *Attorney, Agent, or Firm* — MASCHOFF BRENNAN

(57) ABSTRACT

The present disclosure relates to a class of JAK inhibitor compounds and uses thereof. Specifically, the present disclosure discloses a compound represented by formula (I), isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof. The present disclosure also relates to the application of the compounds in medicine.

(I)

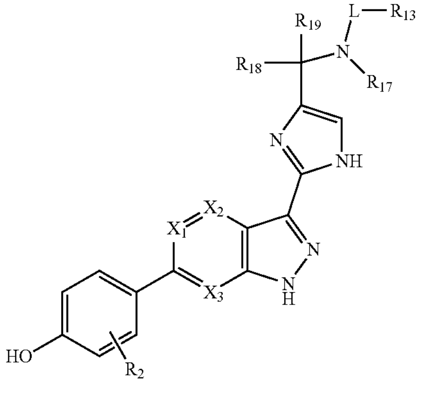

12 Claims, No Drawings

(56) References Cited

FOREIGN PATENT DOCUMENTS

| | | | | | |
|---|---|---|---|---|---|
| CN | 110461839 | A | | 11/2019 | |
| JP | 2014522865 | A | | 9/2014 | |
| JP | 2017515836 | A | | 6/2017 | |
| JP | 2018531982 | A | | 11/2018 | |
| WO | 2012047017 | A2 | | 4/2012 | |
| WO | 2013014567 | A1 | | 1/2013 | |
| WO | WO-2015173683 | A1 | * | 11/2015 | ............. A61P 37/00 |

OTHER PUBLICATIONS

Kishimoto, T. et. al. Int. J. Mol. Sci. 2020, 21(1), 34 (Year: 2020).*
Najjar, A. & Karaman, R. Expert Opinion on Drug Discovery, 2018, 14(3), 199-220 (Year: 2018).*
Tague, A. J., et, al. Med. Chem. Lett. 2021, 12, 413-419 (Year: 2021).*
European Extended Search Report and Written Opinion for related European Application No. 20909530.6 dated Mar. 20, 2023.
The first Office Action issued by the China National Intellectual Property Administration (CNIPA) dated Jul. 17, 2023 for the Chinese Patent Application No. 202011617816.0. (English translation included).
The first Office Action issued by the Japanese Patent Office dated May 31, 2023 for the Japanese Patent Application No. 2022-564690. (English translation included).
Jones, P. et al., Design and Synthesis of a Pan-Janus Kinase Inhibitor Clinical Candidate (PF-06263276) Suitable for Inhaled and Topical Delivery for the Treatment of Inflammatory Diseases of the Lungs and Skin, Journal of Medicinal Chemistry, 60, 767-786, Dec. 2016.
Liao, G. et al., Research and Development of Small Molecule Janus Kinase Inhibitors, Progress in Pharmaceutical Sciences, 38(2), 112-119, Feb. 2014. (English abstract included).
Yin, Y. et al., Research progress of JAK-3 kinase and its inhibitors, Acta Pharmaceutica Sinica, 51(10), 1520-1529, Oct. 2016. (English abstract included).
Chang, X. L. et al., Synthesis and in vitro Activity Evaluation of Azo-indole JAK Inhibitors, Pharmaceutical Journal of Chinese People's Liberation Army, 33(3) 207-211, Jun. 2017. (English abstract included).
International Search Report and Written Opinion of PCT/CN2020/141251, dated Mar. 26, 2021.
Borie et al., "JAK3 inhibition as a new concept for immune suppression", Current Opinion in Investigational Drugs (London, England : 2000), Nov. 1, 2003, 4(11):1297-1303.
Stahl et al., "Handbook of Pharmaceutical Salts: Properties, Selection, and Use", Chemistry International, 2002, vol. 24, No. 3.
Atallah et al., "Prospect of JAK2 inhibitor therapy in myeloproliferative neoplasms", Expert Reviews , Anticancer Ther. 9(5), 663-670, 2009.
Barosi et al., "Novel strategies for patients with chronic myeloproliferative disorders", Current Opinion in Hematology, 16(2): 129-134, Mar. 2009.
Kisseleva et al., "Signaling through the JAK/STAT pathway, recent advances and future challenges", Gene 285, 1-24, 2002.
Santos et al., "Phase 2 study of CEP-701, an orally available JAK2 inhibitor, in patients with primary or post-polycythemia vera/essential thrombocythemia myelofibrosis", Blood, Feb. 11, 2010, vol. 115, No. 6.
Yamaoka et al., "The Janus kinases (Jaks)", Genome Biology 2004, 5:(12), 253, Nov. 2004.

* cited by examiner

JAK INHIBITOR COMPOUND AND USE THEREOF

CROSS REFERENCE TO RELATED APPLICATION

This application is a continuation of International Application No. PCT/CN2020/141251, filed Dec. 30, 2020; which claims priority to Chinese Patent Application No. 201911394671.X, filed on Dec. 30, 2019; both of which are incorporated herein by reference in their entireties.

TECHNICAL FIELD

The present disclosure provides a class of novel compounds with pharmacological activity, which can be used to inhibit Janus kinase (JAK). The present disclosure also relates to a composition comprising the compound, and use of the compound and the composition in the preparation of a medicament for the treatment and/or prevention of JAK-related diseases or disorders.

BACKGROUND

Protein kinases are a family of enzymes that catalyze phosphorylation of specific residues in proteins, and are broadly classified into tyrosine and serine/threonine kinases. Inappropriate kinase activities caused by mutations, over-expression or inappropriate regulation, abnormal regulation or dysregulation, and excessive or insufficient production of growth factors or cytokines are involved in many diseases, including but not limited to cancers, cardiovascular diseases, allergies, asthma and other respiratory diseases, autoimmune diseases, inflammatory diseases, bone diseases, metabolic disorders and neurological and neurodegenerative disorders (such as Alzheimer's disease). Inappropriate kinase activity triggers a variety of biological cell responses associated with cell growth, cell differentiation, cell function, survival, apoptosis, and cell motility related to the aforementioned diseases and other related diseases. Therefore, protein kinases have become an important class of enzymes as targets for therapeutic intervention. In particular, the JAK family of cellular protein tyrosine kinases plays an important role in cytokine signal transduction (Kisseleva et al., Gene, 2002, 285, 1; Yamaoka et al., Genome Biology 2004, 5, 253).

Since the first JAK inhibitor was discovered in the early 1990s, the development of JAK inhibitors has gone through nearly 30 years. JAK is a family of intracellular non-receptor tyrosine kinases, which plays an important role in cytokine receptor signaling pathway by interacting with signal transducer and activator of transcription (STAT). JAK/STAT signaling pathway is involved in many important biological processes such as cell proliferation, differentiation, apoptosis and immune regulation. Compared with other signal pathways, the transmission process of this signal pathway is relatively simple. It is mainly composed of three components, namely tyrosine kinase associated receptor, tyrosine kinase JAK, signal transducer and activator of transcription STAT.

Many cytokines and growth factors transmit signals through the JAK-STAT signal pathway, including interleukins (such as IL-2 to IL-7, IL-9, IL-10, IL-15, IL-21, and the like), GM-CSF (granulocyte/macrophage colony stimulating factor), GH (growth hormone), EGF (epidermal growth factor), PRL (prolactin), EPO (erythropoietin), TPO (thrombopoietin), PDGF (platelet derived factors) and interferons (including IFN-α, IFN-β, IFN-γ and the like) and so on. These cytokines and growth factors have corresponding receptors on the cell membrane. The common feature of these receptors is that the receptor itself does not have kinase activity, but its intracellular segment has a binding site for tyrosine kinase JAK. After the receptor binds to a ligand, tyrosine residues of various target proteins are phosphorylated by activation of JAK that binds to the receptor to realize signal transfer from the extracellular to the intracellular.

JAK is a cytoplasmic tyrosine kinase that transduces cytokine signals from membrane receptors to STAT transcription factors. As mentioned above, JAK is the abbreviation of Janus kinase in English. In Roman mythology, Janus is the double-faced god in charge of the beginning and the end. The reason why it is called Janus kinase is that JAK can phosphorylate cytokine receptors that it binds to, and also phosphorylate multiple signal molecules containing specific SH2 domains. The JAK protein family includes 4 members: JAK1, JAK2, JAK3, and TYK2. They have 7 JAK homology domains (JH) in structure in which the JH1 domain is a kinase domain having the function of encoding kinase proteins; JH2 domain is a "pseudo" kinase domain, which regulates the activity of JH1; and JH3-JH7 constitute a four-in-one domain, which regulates the binding of JAK proteins to receptors.

STAT is a type of cytoplasmic protein that can bind to DNA in the regulatory region of target genes, and is a downstream substrate of JAK. Seven members of the STAT family have been discovered, namely STAT1, STAT2, STAT3, STAT4, STAT5A, STAT5B and STAT6. STAT protein can be divided into the following functional segments in structure including N-terminal conserved sequence, DNA binding region, SH3 domain, SH2 domain and C-terminal transcription activation region. Among them, the segment of the most conserved in sequence and most important in function is the SH2 domain, which has the same core sequence "GTFLLRFSS" as the SH2 domain of tyrosine kinase Src.

JAK-STAT signaling pathway has a wide range of functions and is involved in many important biological processes such as cell proliferation, differentiation, apoptosis, and immune regulation. At present, the research related to disease and drug innovation mainly focuses on inflammatory diseases and neoplastic diseases in which the inflammatory diseases mainly include rheumatoid arthritis, canine dermatitis, psoriasis, ulcerative colitis and Crohn's disease; and the neoplastic diseases mainly involve myelofibrosis, polycythemia vera and primary platelets hyperplasia. In addition, mutations in JAK molecule itself can also cause acute myeloid leukemia (AML), acute lymphocytic leukemia (ALL), ductal breast carcinoma and non-small cell lung cancer (NSCLC), polycythemia vera (PV), essential thrombocythemia (ET), idiopathic myelofibrosis (IMF), chronic myeloid leukemia (CML), and the like.

JAK is a very important drug target. JAK inhibitors developed for this target are mainly used to screen therapeutic drugs for blood system diseases, tumors, rheumatoid arthritis and psoriasis. JAK-1, JAK-2 and TYK-2 are expressed in various tissue cells of human body. JAK-3 is mainly expressed in various hematopoietic tissue cells, mainly in bone marrow cells, thymocytes, NK cells and activated B lymphocytes and T lymphocytes. Studies have shown that JAK2 inhibitors are suitable for myeloproliferative diseases (Santos et al., Blood, 2010, 115:1131; Barosi G. and Rosti V., Curr. Opin. Hematol., 2009, 16:129; Atallah E. and Versotvsek S., 2009 Exp. Rev. Anticancer Ther.

9:663), and JAK3 inhibitors are suitable as immunosuppressive agents (such as, U.S. Pat. No. 6,313,129; Borie et al., Curr. Opin. Investigational Drugs, 2003, 4:1297).

Currently, JAK inhibitors approved by the FDA and EMA include Tofacitinib, Ruxolitinib, and Oclacitinib. JAK inhibitors in the middle and late stages of clinical research include Filgotinib, Peficitinib and so on.

Tofacitinib, a JAK3 inhibitor, was developed by Pfizer and was approved by the FDA in November 2012 for the treatment of moderate to severe rheumatoid arthritis (RA) due to inadequate response or intolerance to methotrexate in adult patients. It is the first oral JAK inhibitor approved for RA treatment. After that, it was approved by Japan PMDA for listing in March 2013 under the trade name Xeljanz. On Mar. 16, 2017, Pfizer China announced that the CFDA had formally approved Pfizer's application for the marketing of the oral JAK inhibitor. It was reported that the drug was approved for the treatment of adult patients with moderate to severe rheumatoid arthritis having inadequate response or intolerance to methotrexate. At present, Tofacitinib is close to being approved for indications such as psoriasis, ulcerative colitis, juvenile idiopathic arthritis; and clinical trials for the treatment of indications such as Crohn's disease and alopecia areata have also entered the mid- to late-stage. The main side effects of Tofacitinib are serious infection rate and increased low-density lipoprotein level. The most common adverse effects are upper respiratory tract infection, headache, diarrhea, nasal congestion, sore throat and nasopharyngitis. In addition, it has been have reported that Tofacitinib can cause side effects such as anemia and neutropenia in clinical studies.

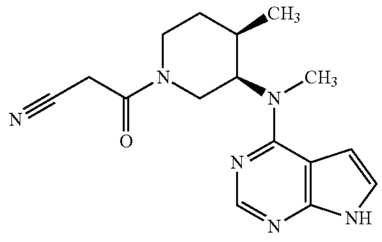

Tofacitinib

Ruxolitinib, a JAK1 and JAK2 inhibitor, was jointly developed by Incyte and Novartis and was approved by the FDA of US in November 2011. It is also the first approved drug specifically for the treatment of myelofibrosis. It was approved by EMA in August 2012 and approved by Japan PMDA for listing in July 2014. The drug is sold by Incyte in the United States under the trade name Jakafi; and is sold by Novartis in Europe and Japan under the trade name Jakavi. Ruxolitinib is under a number of clinical trials in the middle and late stages, wherein the indications include a variety of cancers, GVHD (rejection reaction), alopecia areata, allergic dermatitis, rheumatoid arthritis, vitiligo, psoriasis, and the like. The most common hematological adverse effects with an incidence of >20% of Ruxolitinib are low platelet counts and anemia. The most common non-hematological adverse effects with an incidence of >10% are ecchymosis, dizziness and headache.

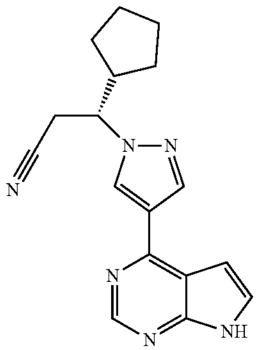

Ruxolitinib

Olatinib, approved by the FDA of US in 2013, is used to control itching and atopic dermatitis caused by canine allergic dermatitis. Olatinib is a new type of JAK and JAK1-dependent cytokine inhibitor. Olatinib is not only a very effective JAK1 inhibitor, but can also inhibit the function of JAK1-dependent cytokines in some anti-allergic, inflammation and pruritic reactions. It has little effect on cytokines that are not involved in activation of JAK1. Oral administration of 0.4-0.6 mg/kg Olatinib twice a day is safe and effective for the treatment of itching caused by allergic dermatitis. During the treatment, Olatinib can relieve itching within 24 hours. In experiments, more than 70% of experimental animals (dogs) alleviated the itching response by more than 50% on the 7th day. However, Olatinib cannot yet be used to treat human diseases.

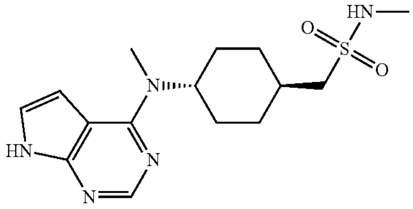

Oclacitinib

Filgotinib, a JAK1 inhibitor, passed Phase III clinical trials in September 2018 for the treatment of rheumatoid arthritis. At the same time, the study of Filgotinib for the treatment of ulcerative colitis and Crohn's disease is currently in clinical phase II/III trials. Filgotinib is a selective JAK1 inhibitor with IC50 of 10 nM, 28 nM, 810 nM and 116 nM for JAK1, JAK2, JAK3 and TYK2, respectively.

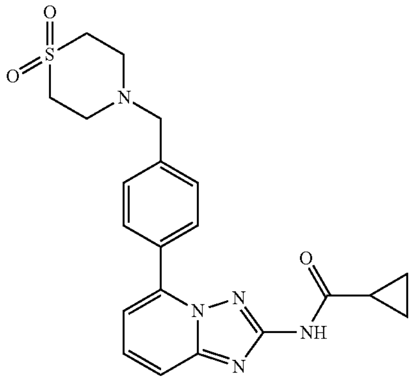

Filgotinib

Peficitinib, a JAK1 and JAK3 inhibitor, developed by Astellas, is currently in Phase III clinical trial for the treatment of rheumatoid arthritis. The Phase II clinical study for the treatment of psoriasis has been completed. Peficitinib is a new oral JAK inhibitor. Peficitinib inhibits the enzyme activities of JAK1, JAK2, JAK3 and TYK2 with IC50 of 3.9 nM, 5.0 nM, 0.71 nM and 4.8 nM, respectively.

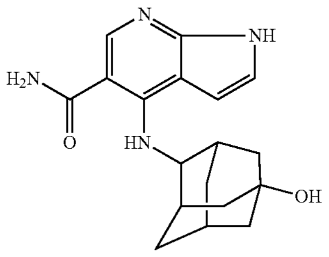

Peficitinib

Although some JAK inhibitors have been approved for listing, and a large number of JAK inhibitors are still in clinical research, these JAK inhibitors are not satisfactory in terms of efficacy or safety. Therefore, there is always a need for JAK inhibitors with better efficacy and/or fewer side effects.

SUMMARY

It is one object of the present disclosure to provide a novel JAK inhibitor alternative to existing JAK inhibitors, so as to provide more options for the treatment of JAK-related diseases.

A further object of the present disclosure is to provide a novel JAK inhibitor with better efficacy and/or better safety than existing JAK inhibitors.

In a first aspect, the present disclosure provides a compound of Formula (I) as a JAK inhibitor (I)

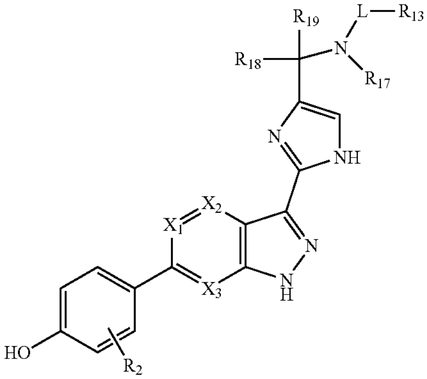

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, wherein L is C═O, O═S═O, $CH_2$ or a linkage; and $X_1$ is N or $CR_{14}$; and $X_2$ is N or $CR_{15}$; and $X_3$ is N or $CR_{16}$; and $R_{13}$ is H, —C(═O)—$R_{20}$, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, and $R_{13}$ is substituted with 0, 1, 2, 3, or 4 $R_1$(s); and $R_{17}$ is selected from the group consisting of H, —OH, —SH, —CN, halogen, —$NO_2$, —$SF_5$, —S—$C_{1-4}$ alkyl, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, —N($R_9$)($R_{10}$), —N($R_{11}$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O)$_2R_{12}$), —S(═O)$_2$—N($R_9$)($R_{10}$), —$SR_{12}$ and —$OR_{12}$, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; or $R_{13}$ and $R_{17}$ form a 4-10 membered heterocycloalkyl with L and N atoms to which they are attached together, and the 4-10 membered heterocycloalkyl is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; and $R_{18}$ and $R_{19}$ are each independently selected from the group consisting of H, —OH, —SH, —CN, halogen, —$NO_2$, —$SF_5$, —S—$C_{1-4}$ alkyl, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, —N($R_9$)($R_{10}$), —N($R_{11}$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O)$_2R_{12}$), —S(═O)$_2$—N($R_9$)($R_{10}$), —$SR_{12}$ and —$OR_{12}$, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; or $R_{18}$ and $R_{19}$ form $C_{3-10}$ cycloalkyl or a 4-10 membered heterocycloalkyl with carbon atom to which they are attached together, and the $C_{3-10}$ cycloalkyl and 4-10 membered heterocycloalkyl are optionally substituted with 1, 2, 3 or 4 substitutes each independently selected from halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl$)_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; and 0, 1, 2, 3 or 4 $R_2$(s) are present in formula (I), and each $R_2$ is independently selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, —N($R_9$)($R_{10}$), —N($R_1$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O$)_2R_{12}$), —S(═O$)_2$—N($R_9$)($R_{10}$), —$SR_{12}$ and —$OR_{12}$, in which the —S—$C_{1-4}$ alkyl, $C_{1-6}$ alkyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—$OR_{12}$, —C(═O)H, —C(═O)$R_{12}$, —C(═O)—N($R_9$)($R_{10}$), —N($R_{11}$)(S(═O$)_2R_{12}$), —S(═O$)_2$—N($R_9$)($R_{10}$), —$SR_{12}$ and —$OR_{12}$; and each $R_1$ is independently selected from H, halogen, —OH, —$NO_2$, —CN, —$SF_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, —N($R_9$)($R_{10}$), —N($R_{11}$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O$)_2R_{12}$), —S(═O$)_2$—N($R_9$)($R_{10}$), —$SR_{12}$ and —$OR_{12}$, in which the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4$(s); and $R_{14}$, $R_{15}$, $R_{16}$ are each independently selected from H, —OH, —SH, —CN, halogen, —$NO_2$, —$SF_5$, —S—$C_{1-4}$ alkyl, $C_{1-6}$ alkyl, $C_{2-8}$ alkenyl, $C_{2-8}$ alkynyl, $C_{1-6}$ alkoxy, $C_{3-7}$ cycloalkyl, 3-7 membered heterocycloalkyl, $C_{5-7}$ aryl, 5-7 membered heteroaryl, —N($R_9$)($R_{10}$), —N($R_{11}$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O$)_2R_{12}$), —S(═O$)_2$—N($R_9$)($R_{10}$), —$SR_{12}$ and —$OR_{12}$, in which the —S—$C_{1-4}$ alkyl, $C_{1-6}$ alkyl, $C_{1-6}$ alkoxy, $C_{3-7}$ cycloalkyl, and 3-7 membered heterocycloalkyl are optionally substituted with 1, 2 or 3 substitutes selected from halogen, —OH, —$NH_2$, —$NH(CH_3)$, —$N(CH_3)_2$, —CN, $C_{1-4}$ alkyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl$)_2$, —N($C_{1-4}$ alkyl)(C(═O)$C_{1-4}$ alkyl), $C_{1-4}$ haloalkyl, $C_{1-4}$ alkoxy and $C_{1-4}$ haloalkoxy; and $R_{20}$ is independently selected from H, —OH, —SH, —CN, halogen, —$NO_2$, —$SF_5$, —S—$C_{1-4}$ alkyl, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, —N($R_9$)($R_{10}$), —N($R_{11}$)(C(═O)$R_{12}$), —C(═O)—N($R_9$)($R_{10}$), —C(═O)—$R_{12}$, —C(═O)—$OR_{12}$, —OC(═O)$R_{12}$, —N($R_{11}$)(S(═O$)_2R_{12}$), —S(═O$)_2$—N($R_9$)($R_{10}$), —$SR_{12}$ and —$OR_{12}$, in which each option in the group is optionally substituted with 1, 2, 3 or 4 substitutes selected from halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl$)_2$, —N($C_{1-4}$ alkyl)(C(═O)$C_{1-4}$ alkyl), $C_{1-4}$ haloalkyl, $C_{1-4}$ alkoxy and $C_{1-4}$ haloalkoxy; and $R_3$ and $R_4$ are each independently selected from H, halogen, —OH, —$NO_2$, —CN, —$SF_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, —N($R_5$)($R_6$), —N($R_{11}$)(C(═O)$R_{12}$), —CON($R_7$)($R_8$), —C(═O)—$R_{12}$, —C(═O)—$OR_{12}$, —OC(═O)$R_{12}$, —N($R_{11}$)(S(═O$)_2R_{12}$), —S(═O$)_2$—N($R_9$)($R_{10}$), —$SR_{12}$ and —$OR_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, or 3 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—$OR_{12}$, —C(═O)H, —C(═O)$R_{12}$, —C(═O)—N($R_9$)($R_{10}$), —N($R_{11}$)(S(═O$)_2R_{12}$), —S(═O$)_2$—N($R_9$)($R_{10}$), —$SR_{12}$ and —$OR_{12}$; and $R_5$, $R_6$, $R_7$, $R_8$, $R_9$, $R_{10}$, $R_{11}$, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each option in the group is optionally substituted with 1, 2, 3 or 4 substituent(s) each independently selected from the group consisting of halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl$)_2$, $C_{1-4}$ haloalkyl, $C_{1-4}$ alkoxy and $C_{1-4}$ haloalkoxy.

Preferably, the present disclosure relates to a compound of Formula (I)

(I)

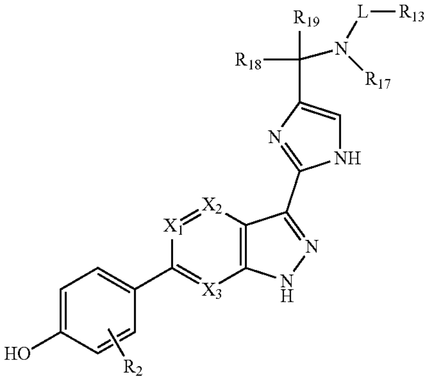

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, wherein L is C=O, O=S=O, $CH_2$ or a linkage; and $X_1$ is N or $CR_{14}$; and $X_2$ is N or $CR_{15}$; and $X_3$ is N or $CR_{16}$; and $R_{13}$ is H, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, and $R_{13}$ is substituted with 0, 1, 2, 3, or 4 $R_1$(s); and $R_{17}$ is selected from the group consisting of H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, —C(=O)—N($R_9$)($R_{10}$), —C(=O)—$R_{12}$, —C(=O)—O$R_{12}$, and —S(=O)$_2$—N($R_9$)($R_{10}$), in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, —N($C_{1-4}$ alkyl)(C(=O)$C_{1-4}$ alkyl), $C_{1-4}$ haloalkyl, $C_{1-4}$ alkoxy and $C_{1-4}$haloalkoxy; or $R_{13}$ and $R_{17}$ form a 4-10 membered heterocycloalkyl with L and N atoms to which they are attached together, and the 4-10 membered heterocycloalkyl is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, —N($C_{1-4}$ alkyl)(C(=O) $C_{1-4}$ alkyl), $C_{1-4}$ haloalkyl, $C_{1-4}$ alkoxy and $C_{1-4}$haloalkoxy; and $R_{18}$ and $R_{19}$ are each independently selected from the group consisting of H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, —N($C_{1-4}$ alkyl)(C(=O) $C_{1-4}$ alkyl), $C_{1-4}$ haloalkyl, $C_{1-4}$ alkoxy and $C_{1-4}$haloalkoxy; or $R_{18}$ and $R_{19}$ form $C_{3-10}$ cycloalkyl or a 4-10 membered heterocycloalkyl with carbon atom to which they are attached together, and the $C_{3-10}$ cycloalkyl and 4-10 membered heterocycloalkyl are optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, —N($C_{1-4}$ alkyl)(C(=O) $C_{1-4}$ alkyl), $C_{1-4}$ haloalkyl, $C_{1-4}$ alkoxy and $C_{1-4}$haloalkoxy; and 0, 1, 2, 3 or 4 $R_2$(s) are present in formula (I), and each $R_2$ is independently selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, —N($R_9$)($R_{10}$), —N($R_{11}$)(C(=O)$R_{12}$), —C(=O)—N($R_9$)($R_{10}$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the —S—$C_{1-4}$ alkyl, $C_{1-6}$ alkyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$; and each $R_1$ is independently selected from H, halogen, —OH, —$NO_2$, —CN, —$SF_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, —N($R_9$)($R_{10}$), —N($R_{11}$)(C(=O)$R_{12}$), —C(=O)—N($R_9$)($R_{10}$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4$(s); and $R_{14}$, $R_{15}$, $R_{16}$ are each independently selected from H, —OH, —SH, —CN, halogen, —$NO_2$, —$SF_5$, —S—$C_{1-4}$ alkyl, $C_{1-6}$ alkyl, $C_{2-8}$ alkenyl, $C_{2-8}$ alkynyl, $C_{1-6}$ alkoxy, $C_{3-7}$ cycloalkyl, 3-7 membered heterocycloalkyl, $C_{5-7}$ aryl, 5-7 membered heteroaryl, —N($R_9$)($R_{10}$), —N($R_{11}$)(C(═O)$R_{12}$), —C(═O)—N($R_9$)($R_{10}$), —C(═O)—$R_{12}$, —C(═O)—O$R_{12}$, —OC(═O)$R_{12}$, —N($R_{11}$)(S(═O)$_2$$R_{12}$), —S(═O)$_2$—N($R_9$)($R_{10}$), —S$R_{12}$ and —O$R_{12}$, in which the —S—$C_{1-4}$ alkyl, $C_{1-6}$ alkyl, $C_{1-6}$ alkoxy, $C_{3-7}$ cycloalkyl, and 3-7 membered heterocycloalkyl are optionally substituted with 1, 2 or 3 substitutes selected from halogen, —OH, —$NH_2$, —NH($CH_3$), —N($CH_3$)$_2$, —CN, $C_{1-4}$ alkyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$ haloalkoxy; and $R_3$ and $R_4$ are each independently selected from H, halogen, —OH, —$NO_2$, —CN, —$SF_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, —N($R_5$)($R_6$), —N($R_{11}$)(C(═O)$R_{12}$), —CON($R_7$)($R_8$), —C(═O)—$R_{12}$, —C(═O)—O$R_{12}$, —OC(═O)$R_{12}$, —N($R_{11}$)(S(═O)$_2$$R_{12}$), —S(═O)$_2$—N($R_9$)($R_{10}$), —S$R_{12}$ and —O$R_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, or 3 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—O$R_{12}$, —C(═O)H, —C(═O)$R_{12}$, —C(═O)—N($R_9$)($R_{10}$), —N($R_{11}$)(S(═O)$_2$$R_{12}$), —S(═O)$_2$—N($R_9$)($R_{10}$), —S$R_{12}$ and —O$R_{12}$; and $R_5$, $R_6$, $R_7$, $R_8$, $R_9$, $R_{10}$, $R_{11}$, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each option in the group are each optionally substituted with 1, 2, 3 or 4 substituent(s) each independently selected from the group consisting of halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy.

In some preferred embodiments of the present disclosure, an isotopically labeled compound of the above-mentioned compound of formula (I) is provided. In some more preferred embodiments of the present disclosure, an isotopically labeled compound of the compound of formula (I) is provided, wherein all Hs are each independently and optionally replaced by D.

In some preferred embodiments of the present disclosure, in formula (I), $X_1$ is N. In some preferred embodiments of the present disclosure, in formula (I), $X_2$ is N. In some preferred embodiments of the present disclosure, in formula (I), $X_3$ is N. In some preferred embodiments of the present disclosure, in formula (I), $X_1$ is $CR_{14}$, $X_2$ is $CR_{15}$, and $X_3$ is $CR_{16}$. In some preferred embodiments of the present disclosure, in formula (I), $X_1$ is $CR_{14}$, $X_2$ is $CR_{15}$, $X_3$ is $CR_{16}$, and $X_1$, $X_2$, and $X_3$ are each independently selected from H, —OH, —CN, halogen, $C_{1-6}$ alkyl, $C_{1-6}$ alkoxy, $C_{3-7}$ cycloalkyl, and 3-7 membered heterocycloalkyl. In some preferred embodiments of the present disclosure, in formula (I), $X_1$, $X_2$ and $X_3$ are the same. In some preferred embodiments of the present disclosure, in formula (I), $X_1$, $X_2$ and $X_3$ are CH. In some preferred embodiments of the present disclosure, in formula (I), $X_1$, $X_2$ and $X_3$ are N.

In some more preferred embodiments of the present disclosure, there is provided an isotopically labeled compound of the compound of formula (I), wherein all H are each independently and optionally replaced by D, and $X_1$, $X_2$ and $X_3$ are the same. In some more preferred embodiments of the present disclosure, there is provided an isotopically labeled compound of the compound of formula (I), wherein all Hs are each independently and optionally replaced by D, and $X_1$, $X_2$ and $X_3$ are all CH.

In some preferred embodiments of the present disclosure, in formula (I), L is C═O, O═S═O or $CH_2$. In some particularly preferred embodiments of the present disclosure, in formula (I), L is C═O. In some particularly preferred embodiments of the present disclosure, in formula (I), L is O═S═O. In some particularly preferred embodiments of the present disclosure, in formula (I), L is $CH_2$. In other embodiments of the present disclosure, in formula (I), L is a linkage.

In some particularly preferred embodiments of the present disclosure, in formula (I), $X_1$, $X_2$ and $X_3$ are all CH, and L is C═O.

In some particularly preferred embodiments of the present disclosure, in formula (I), $X_1$, $X_2$ and $X_3$ are all CH, and L is O═S═O.

In some particularly preferred embodiments of the present disclosure, in formula (I), $X_1$, $X_2$ and $X_3$ are all CH, and L is $CH_2$.

In some particularly preferred embodiments of the present disclosure, in formula (I), $X_1$, $X_2$ and $X_3$ are all CH, and L is a linkage.

In some particularly preferred embodiments of the present disclosure, in formula (I), $X_1$, $X_2$ and $X_3$ are all N, and L is C═O.

In some particularly preferred embodiments of the present disclosure, in formula (I), $X_1$, $X_2$ and $X_3$ are all N, and L is O═S═O.

In some particularly preferred embodiments of the present disclosure, in formula (I), $X_1$, $X_2$ and $X_3$ are all N, and L is $CH_2$.

In some particularly preferred embodiments of the present disclosure, in formula (I), $X_1$, $X_2$ and $X_3$ are all N, and L is a linkage.

In some particularly preferred embodiments of the present disclosure, in formula (I), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is C═O.

In some particularly preferred embodiments of the present disclosure, in formula (I), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is O═S═O.

In some particularly preferred embodiments of the present disclosure, in formula (I), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is $CH_2$.

In some particularly preferred embodiments of the present disclosure, in formula (I), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is a linkage.

In some preferred embodiments of the present disclosure, in formula (I), $R_{13}$ is H, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl wherein $R_{13}$ is optionally substituted with 1, 2, 3 or 4 $R_1$(s). In some preferred embodiments of the present disclosure, in formula (I), $R_{13}$ is H, $C_{1-6}$ alkyl or $C_{3-7}$ cycloalkyl, 3-7 membered heterocycloalkyl, $C_{5-7}$ aryl, 5-7 membered heteroaryl wherein $R_{13}$ is optionally substituted with 1, 2, 3 or 4 $R_1$(s). In some preferred embodiments of the present disclosure, in formula (I), $R_{13}$ is $C_{1-6}$ alkyl or $C_{3-7}$ cycloalkyl, 4-6 membered heterocycloalkyl, phenyl, 5-6 membered heteroaryl wherein $R_{13}$ is optionally substituted with 1, 2, 3 or 4 $R_1$(s). In some preferred embodiments of the present disclosure, in formula (I), $R_{13}$ is $C_{1-4}$ alkyl or $C_{3-7}$ cycloalkyl, 4-6 membered heterocycloalkyl, phenyl, 5-6 membered heteroaryl wherein $R_{13}$ is optionally substituted with 1, 2, 3 or 4 $R_1$(s). In some preferred embodiments of the present disclosure, in formula (I), $R_{13}$ is $C_{1-4}$ alkyl or $C_{3-7}$ cycloalkyl, 4-6 membered heterocycloalkyl wherein $R_{13}$ is optionally substituted with 1, 2, 3 or 4 $R_1$(s). In some preferred embodiments of the present disclosure, in formula (I), $R_{13}$ is $C_{1-4}$ alkyl or $C_{3-6}$ cycloalkyl, 5-6 membered heterocycloalkyl wherein $R_{13}$ is optionally substituted with 1, 2, 3 or 4 $R_1$(s). In some preferred embodiments of the present disclosure, in formula (I), $R_{13}$ is $C_{1-3}$ alkyl, cyclopropyl or 6 membered heterocycloalkyl wherein $R_{13}$ is optionally substituted with 1, 2, 3 or 4 $R_1$(s). In some particularly preferred embodiments of the present application, in formula (I), $R_{13}$ is methyl, ethyl, n-propyl, isopropyl, cyclopropyl or pyrazinyl wherein $R_{13}$ is optionally substituted with 1, 2, 3 or 4 $R_1$(s). In some particularly preferred embodiments of the present application, in formula (I), $R_{13}$ is methyl. In some particularly preferred embodiments of the present application, in formula (I), $R_{13}$ is ethyl. In some particularly preferred embodiments of the present application, in formula (I), $R_{13}$ is n-propyl. In some particularly preferred embodiments of the present application, in formula (I), $R_{13}$ is isopropyl. In some particularly preferred embodiments of the present application, in formula (I), $R_{13}$ is cyclopropyl. In some particularly preferred embodiments of the present application, in formula (I), $R_{13}$ is pyrazinyl. In some particularly preferred embodiments of the present application, in formula (I), $R_{13}$ is pyrazinyl and is substituted with piperidinyl. In some particularly preferred embodiments of the present application, in formula (I), $R_{13}$ is pyrazinyl and is substituted with morpholinyl.

In some preferred embodiments of the present disclosure, in formula (I), $R_{17}$ is H, —OH, —SH, —CN, halogen, —$NO_2$, —$SF_5$, —S—$C_{1-4}$ alkyl, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, and is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy. In some preferred embodiments of the present disclosure, in formula (I), $R_{17}$ is H, —OH, $C_{1-6}$ alkyl, $C_{3-7}$ cycloalkyl, 4-6 membered heterocycloalkyl, phenyl, or 5-6 membered heteroaryl, and is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy. In some preferred embodiments of the present disclosure, in formula (I), $R_{17}$ is H, —OH or $C_{1-6}$ alkyl, and is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy. In some particularly preferred embodiments of the present disclosure, in formula (I), $R_{17}$ is H.

In some preferred embodiments of the present disclosure, in formula (I), $R_{13}$ and $R_{17}$ form a 4-6 membered heterocycloalkyl with L and N atoms to which they are attached together, and the 4-6 membered heterocycloalkyl is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy. In some preferred embodiments of the present disclosure, in formula (I), $R_{13}$ and $R_{17}$ form a 4-6 membered azacycloalkyl with L and N atoms to which they are attached together, and the 4-6 membered azacycloalkyl is optionally substituted with 1, 2 or 3 substitutes each independently selected from halogen, —$CF_3$, —OH, —$NH_2$, —NH($CH_3$), —N($CH_3$)$_2$, —CN, oxo, and $C_{1-4}$ alkyl. In some preferred embodiments of the present disclosure, in formula (I), $R_{13}$ and $R_{17}$ form a 5 membered heterocycloalkyl with L and N atoms to which they are attached together, and the 5 membered heterocycloalkyl is optionally substituted with 1, 2 or 3 substitutes each independently selected from halogen, —$CF_3$, —OH, —$NH_2$, —NH($CH_3$), —N($CH_3$)$_2$, —CN, oxo, and $C_{1-4}$ alkyl. In some preferred embodiments of the present disclosure, in formula (I), $R_{13}$ and $R_{17}$ form pyrrolidinyl with L and N atoms to which they are attached together. In some preferred embodiments of the present disclosure, in formula (I), $R_{13}$ and $R_{17}$ form pyrrolidinyl with L and N atoms to which they are attached together and the pyrrolidinyl is substituted with —OH.

In some preferred embodiments of the present disclosure, in formula (I), $R_{18}$ and $R_{19}$ are each independently selected from the group consisting of H, $C_{1-6}$ alkyl, $C_{1-4}$ haloalkyl, $C_{2-8}$ alkenyl, $C_{2-8}$ alkynyl, $C_{3-7}$ cycloalkyl, 4-14 membered heterocycloalkyl, $C_{6-10}$ aryl, and 5-10 membered heteroaryl, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, and —S—$C_{1-4}$ alkyl. In some preferred embodiments of the present disclosure, in formula (I), $R_{18}$ and $R_{19}$ are each independently selected from the group consisting of H and $C_{1-6}$ alkyl, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, and oxo. In some particularly preferred embodiments of the present disclosure, in formula (I), $R_{18}$ is H. In some particularly preferred embodiments of the present disclosure, in formula (I), $R_{19}$ is H. In some particularly preferred embodiments of the present disclosure, in formula (I), $R_{18}$ and $R_{19}$ both are H.

In some preferred embodiments of the present disclosure, in formula (I), $R_{18}$ and $R_{19}$ form $C_{3-6}$ cycloalkyl or a 4-10 membered heterocycloalkyl with carbon atom to which they are attached together, and the $C_{3-6}$ cycloalkyl and 4-10 membered heterocycloalkyl are optionally substituted with 1, 2, or 3 substitutes each independently selected from halogen, —$CF_3$, —OH, —$NH_2$, —NH($CH_3$), —N($CH_3$)$_2$, —CN, oxo, and $C_{1-4}$ alkyl.

In some particularly preferred embodiments of the present disclosure, in formula (I), one, two or three $R_2$(s) are present and each $R_2$ is selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, and 4-10 membered heterocycloalkyl, in which the —S—$C_{1-4}$ alkyl, $C_{1-6}$ alkyl, $C_{3-7}$ cycloalkyl, and 4-10 membered heterocycloalkyl are each optionally substituted with 1, 2 or 3 substituent(s) each independently selected from the group consisting of halogen, —OH, —$NH_2$, —NH($CH_3$), —N($CH_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one, two or three $R_2$(s) are present and each $R_2$ is selected from halogen, $C_{1-6}$ alkyl and $C_{3-6}$ cycloalkyl, in which the $C_{1-6}$ alkyl and $C_{3-6}$ cycloalkyl are each optionally substituted with 1, 2 or 3 substituent(s) each independently selected from the group consisting of halogen, —OH, —$NH_2$, —NH($CH_3$), —N($CH_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one, two or three $R_2$(s) are present and each $R_2$ is selected from halogen, and $C_{1-6}$ alkyl, in which the $C_{1-6}$ alkyl is optionally substituted with 1, 2 or 3 substituent(s) each independently selected from the group consisting of halogen, —OH, —$NH_2$, —NH($CH_3$), —N($CH_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one, or two $R_2$(s) are present and each $R_2$ is selected from halogen, and $C_{1-6}$ alkyl. In some particularly preferred embodiments of the present disclosure, in formula (I), one or two $R_2$(s) are present and each $R_2$ is selected from fluorine, chlorine, bromine, methyl, ethyl, n-propyl, isopropyl, n-butyl, and isobutyl. In some preferred embodiments of the present disclosure, in formula (I), one or two $R_2$(s) are present, and each $R_2$ is selected from fluorine, chlorine, methyl, ethyl, n-propyl, and isopropyl. In some preferred embodiments of the present disclosure, in formula (I), one or two $R_2$(s) are present, and each $R_2$ is selected from fluorine, methyl, and ethyl. In some preferred embodiments of the present disclosure, in formula (I), one or two $R_2$ (s) are present, and each $R_2$ is selected from fluorine and ethyl. In some preferred embodiments of the present disclosure, in formula (I), one $R_2$ is present, and $R_2$ is selected from fluorine and ethyl. In some preferred embodiments of the present disclosure, in formula (I), two $R_2$(s) are present, and each $R_2$ is selected from fluorine and ethyl. In some particularly preferred embodiments of the present disclosure, in formula (I), two $R_2$(s) are present which are respectively fluorine and ethyl. In some particularly preferred embodiments of the present disclosure, in formula (I), one $R_2$ is present, and $R_2$ is an ethyl group. In some particularly preferred embodiments of the present disclosure, in formula (I), one $R_2$ is present, and $R_2$ is fluoro.

In some preferred embodiments of the present disclosure, in formula (I), $R_{13}$ is substituted with 0, 1, 2, 3 or 4 $R_1$(s), and each $R_1$ is independently selected from H, halogen, —OH, —$NO_2$, —CN, —$SF_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl, wherein the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and wherein the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3 or 4 $R_4$(s). In some preferred embodiments of the present disclosure, in formula (I), $R_{13}$ is substituted with 0, 1, 2, 3 or 4 $R_1$(s), and each $R_1$ is independently selected from H, halogen, —OH, —$NO_2$, —CN, —$SF_5$, —SH, —S—$C_{1-4}$ alkyl, $C_{1-8}$ alkyl, $C_{3-7}$ cycloalkyl, 3-7 membered heterocycloalkyl, $C_{5-7}$ aryl, and 5-7 membered heteroaryl, wherein the —S—$C_{1-4}$ alkyl, and $C_{1-8}$ alkyl are optionally substituted with 1, 2, 3 or 4 $R_3$(s), and wherein the $C_{3-7}$ cycloalkyl, 3-7 membered heterocycloalkyl, $C_{5-7}$ aryl, and 5-7 membered heteroaryl are optionally substituted with 1, 2, 3, or 4 $R_4$(s). In some preferred embodiments of the present disclosure, in formula (I), $R_{13}$ is substituted with 0, 1, 2, 3 or 4 $R_1$(s), and each $R_1$ is independently selected from halogen, —OH, $C_{1-8}$ alkyl, $C_{3-7}$ cycloalkyl, 3-7 membered heterocycloalkyl, $C_{5-7}$ aryl, 5-7 membered heteroaryl, wherein the $C_{1-8}$ alkyl is optionally substituted with 1, 2, 3 or 4 $R_3$(s), and wherein the $C_{3-7}$ cycloalkyl, 3-7 membered heterocycloalkyl, $C_{5-7}$ aryl, 5-7 membered heteroaryl are optionally substituted with 1, 2, 3 or 4 $R_4$(s). In some preferred embodiments of the present disclosure, in formula (I), $R_{13}$ is substituted with 0, 1, 2, 3 or 4 $R_1$(s), and each $R_1$ is independently selected from halogen, —OH, $C_{1-8}$ alkyl, $C_{3-7}$ cycloalkyl, and 3-7 membered heterocycloalkyl, wherein the $C_{1-8}$ alkyl is optionally substituted with 1, 2, or 3 $R_3$(s), and wherein the $C_{3-7}$ cycloalkyl, and 3-7 membered heterocycloalkyl are optionally substituted with 1, 2, or 3 $R_4$(s). In some preferred embodiments of the present disclosure, in formula (I), $R_{13}$ is substituted with 0, 1, 2, 3 or 4 $R_1$(s), and each $R_1$ is independently selected from halogen, —OH, $C_{1-6}$ alkyl, $C_{3-7}$ cycloalkyl, 5-7 membered heterocycloalkyl, wherein the $C_{1-6}$ alkyl is optionally substituted with 1, 2, or 3 $R_3$(s), and wherein the $C_{3-7}$ cycloalkyl, and 5-7-membered heterocycloalkyl are optionally substituted with 1, 2, or 3 $R_4$(s). In some preferred embodiments of the present disclosure, in formula (I), $R_{13}$ is substituted with 0, 1, 2, 3 or 4 $R_1$(s), and each $R_1$ is independently selected from halogen, —OH, $C_{1-4}$ alkyl, $C_{3-6}$ cycloalkyl, and 5-7 membered heterocycloalkyl, wherein the $C_{1-4}$ alkyl is optionally substituted with 1 or 2 $R_3$(s), and wherein the $C_{3-6}$ cycloalkyl and 5-7 membered heterocycloalkyl are optionally substituted with 1, 2, or 3 $R_4$(s). In some preferred embodiments of the present disclosure, in formula (I), $R_{13}$ is substituted with 0, 1, 2, 3 or 4 $R_1$(s), and each $R_1$ is independently selected from 5-7 membered heterocycloalkyl, wherein the 5-7 membered heterocycloalkyl is optionally substituted with 1, 2, or 3 $R_4$(s). In some particularly preferred embodiments of the present disclosure, in formula (I), $R_{13}$ is substituted with 0 or 1 $R_1$, and $R_1$ is selected from piperidinyl or morpholinyl. In some particularly preferred embodiments of the present disclosure, in formula (I), $R_1$ is absent. In some particularly preferred embodiments of the present disclosure, in formula (I), $R_{13}$ is substituted with 1 $R_1$. In some particularly preferred embodiments of the present application, in formula (I), $R_{13}$ is substituted with 1 $R_1$, and $R_1$ is piperidinyl. In some particularly preferred embodiments of the present application, in formula (I), $R_{13}$ is substituted with 1 $R_1$, and $R_1$ is morpholinyl.

The preferred options of the respective substituents mentioned in the above various preferred embodiments can be combined with each other in any way, and various combinations thereof are within the scope of the present disclosure.

In the most preferred embodiments of the present disclosure, the compound of formula (I) is each specific compound shown in Examples herein. That is, the compound of formula (I) is selected from N-((2-(6-(2-ethyl-5-fluoro-4-hydroxyphenyl)-1H-indazol-3-yl)-1H-imidazol-4-yl)methyl)-5-(piperidin-1-yl)pyrazine-2-carboxamide;
N-((2-(6-(2-ethyl-5-fluoro-4-hydroxyphenyl)-1H-indazol-3-yl)-1H-imidazol-4-yl)methyl)propionamide;
N-((2-(6-(2-ethyl-5-fluoro-4-hydroxyphenyl)-1H-indazol-3-yl)-1H-imidazol-4-yl)methyl)cyclopropanecarboxamide;
N-((2-(6-(2-ethyl-5-fluoro-4-hydroxyphenyl)-1H-indazol-3-yl)-1H-imidazol-4-yl)methyl)isobutyramide;
N-((2-(6-(2-ethyl-5-fluoro-4-hydroxyphenyl)-1H-indazol-3-yl)-1H-imidazol-4-yl)methyl)methanesulfonamide;
N-((2-(6-(2-ethyl-5-fluoro-4-hydroxyphenyl)-1H-indazol-3-yl)-1H-imidazol-4-yl)methyl)-5-morpholinopyrazine-2-carboxamide;
(S)-1-((2-(6-(2-ethyl-5-fluoro-4-hydroxyphenyl)-1H-indazol-3-yl)-1H-imidazol-4-yl)methyl)pyrrolidin-3-ol;
1-((2-(6-(2-ethyl-5-fluoro-4-hydroxyphenyl)-1H-indazol-3-yl)-1H-imidazol-4-yl)methyl)piperidin-4-ol;
N-((2-(6-(2-ethyl-5-fluoro-4-hydroxyphenyl)-1H-indazol-3-yl)-1H-imidazol-4-yl)methyl)-N-methylcyclopropanecarboxamide (Ex-10) 1-((2-(6-(2-ethyl-5-fluoro-4-hydroxyphenyl)-1H-indazol-3-yl)-1H-imidazol-4-yl)methyl)piperidine-4-nitrile;
1-((2-(6-(2-ethyl-5-fluoro-4-hydroxyphenyl)-1H-indazol-3-yl)-1H-imidazol-4-yl)methyl)pyrrolidine-3-carbonitrile;
5-ethyl-2-fluoro-4-(3-(4-(morpholinomethyl)-1H-imidazol-2-yl)-1H-indazol-6-yl)phenol;
5-ethyl-2-fluoro-4-(3-(4-((pyridin-3-ylamino)methyl)-1H-imidazol-2-yl)-1H-indazol-6-yl)phenol;
5-ethyl-2-fluoro-4-(3-(4-(((1-methyl-1H-pyrazol-4-yl)amino)methyl)-1H-imidazol-2-yl)-1H-indazol-6-yl)phenol;
3-((2-(6-(2-ethyl-5-fluoro-4-hydroxyphenyl)-1H-indazol-3-yl)-1H-imidazol-4-yl)methyl)-1-(2-hydroxyethyl)-1-methylurea;
4-(3-(4-(((cyclopropylmethyl)amino)methyl)-1H-imidazol-2-yl)-1H-indazol-6-yl)-5-ethyl-2-fluorophenol;
N-((2-(6-(2-ethyl-5-fluoro-4-hydroxyphenyl)-1H-indazol-3-yl)-1H-imidazol-4-yl)methyl)cyclopropanesulfonamide;
N-((2-(6-(2-ethyl-5-fluoro-4-hydroxyphenyl)-1H-indazol-3-yl)-1H-imidazol-4-yl)methyl)ethanesulfonamide;
N-((2-(6-(2-ethyl-5-fluoro-4-hydroxyphenyl)-1H-indazol-3-yl)-1H-imidazol-4-yl)methyl)-4-hydroxypiperidine-1-carboxamide;
(R)—N-((2-(6-(2-ethyl-5-fluoro-4-hydroxyphenyl)-1H-indazol-3-yl)-1H-imidazol-4-yl)methyl)-3-hydroxy-N-methylpyrrolidine-1-carboxamide;
(R)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide;
(S)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide;
5-ethyl-2-fluoro-4-(3-(4-(((2-hydroxyethyl)(methyl)amino)methyl)-1H-imidazol-2-yl)-1H-indazol-6-yl)phenol;
N-((2-(6-(2-ethyl-5-fluoro-4-hydroxyphenyl)-1H-indazol-3-yl)-1H-imidazol-4-yl)methyl)propane-2-sulfonamide;
methyl ((2-(6-(2-ethyl-5-fluoro-4-hydroxyphenyl)-1H-indazol-3-yl)-1H-imidazol-4-yl)methyl)carbamate;
2-cyanoethyl ((2-(6-(2-ethyl-5-fluoro-4-hydroxyphenyl)-1H-indazol-3-yl)-1H-imidazol-4-yl)methyl) carbamate;
N-((2-(6-(2-ethyl-5-fluoro-4-hydroxyphenyl)-1H-indazol-3-yl)-1H-imidazol-4-yl)methyl)cyclobutanecarboxamide;
N-((2-(6-(2-ethyl-5-fluoro-4-hydroxyphenyl)-1H-indazol-3-yl)-1H-imidazol-4-yl)methyl)-1-methylpyrrolidine-3-carboxamide;
4-(3-(4-((2-azabicyclo[2.2.2]octan-2-yl)methyl)-1H-imidazol-2-yl)-1H-indazol-6-yl)-5-ethyl-2-fluorophenol;
4-(3-(4-((cyclobutylamino)methyl)-1H-imidazol-2-yl)-1H-indazol-6-yl)-5-ethyl-2-fluorophenol;
5-ethyl-2-fluoro-4-(3-(4-(((tetrahydrofuran-3-yl)amino)methyl)-1H-imidazol-2-yl)-1H-indazol-6-yl) phenol;
5-ethyl-2-fluoro-4-(3-(4-((pyridin-2-ylamino)methyl)-1H-imidazol-2-yl)-1H-indazol-6-yl)phenol;
N-((2-(6-(2-ethyl-5-fluoro-4-hydroxyphenyl)-1H-indazol-3-yl)-1H-imidazol-4-yl)methyl)-1-methyl-1H-pyrazole-4-carboxamide;
5-ethyl-2-fluoro-4-(3-(4-(((1-methylpyrrolidin-3-yl)amino)methyl)-1H-imidazol-2-yl)-1H-indazole-6-yl)phenol;
N-((2-(6-(2-ethyl-5-fluoro-4-hydroxyphenyl)-1H-indazol-3-yl)-1H-imidazol-4-yl)methyl)morpholine-4-carboxamide;
N-((2-(6-(2-ethyl-5-fluoro-4-hydroxyphenyl)-1H-indazol-3-yl)-1H-imidazol-4-yl)methyl)-4-methylpiperazine-1-carboxamide; and
5-ethyl-4-(3-(4-((4-ethylpiperazin-1-yl)methyl)-1H-imidazol-2-yl)-1H-indazol-6-yl)-2-fluorophenol.

For simplicity, hereinafter, the term "a compound as shown by Formula (I)" or "a compound of Formula (I)" or "a compound of the invention" or "a compound according to the invention" also encompasses any optical isomer, geometric isomer, tautomer or a mixture of various isomers of the compound of Formula (I).

The term "optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, or a Z isomer. A geometric isomer comprises a cis isomer, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state. As used herein, the term "a compound as shown by Formula (I)" also encompasses any tautomer of the compound of Formula (I).

Unless otherwise indicated, reference to "a compound as shown by Formula (I)" or "a compound of Formula (I)" or "a compound of the invention" or "a compound according to the invention" herein also encompasses isotopically-labeled compounds obtained by replacing any atom of the compound with its isotopic atom.

The invention comprises all pharmaceutically acceptable isotopically-labeled compounds of Formula (I) wherein one or more atoms are replaced by atoms having the same atomic number but different atomic mass or mass number than those normally found in nature.

Examples of isotopes suitable for inclusion in the compounds of the invention include isotopes of hydrogen, such as $^{2}H$ (D) and $^{3}H$ (T), of carbon, such as $^{11}C$, $^{13}C$ and $^{14}C$, of chlorine, such as $^{36}Cl$, of fluorine, such as $^{18}F$, of iodine, such as $^{123}I$ and $^{125}I$, of nitrogen, such as $^{13}N$ and $^{15}N$, of oxygen, such as $^{15}O$, $^{17}O$ and $^{18}O$, and of sulphur, such as 35S.

Certain isotopically-labelled compounds of formula (I), for example, those incorporating a radioactive isotope, are useful in drug and/or substrate tissue distribution studies. The radioactive isotopes deuterium, i.e. $^{2}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compound of formula (I) may exist in the form of a pharmaceutically acceptable salt, for example, an acid addition salt and/or a base addition salt of the compound of formula (I). Unless otherwise indicated, "a pharmaceutically acceptable salt" as used herein includes acid addition salts or base addition salts that may appear in the compound of formula (I).

The pharmaceutically acceptable salt of the compound of formula (I) include acid addition salts and base addition salts thereof. Suitable acid addition salts are formed from acids that form non-toxic salts. Examples include but are not limited to: acetate, adipate, aspartate, benzoate, benzenesulfonate, bicarbonate/carbonate, bisulfate/sulfate, borate, camphor sulfonate, citrate, cyclohexamine sulfonate, ethanedisulfonate, formate, fumarate, glucoheptonate, gluconate, glucuronate, hexafluorophosphate, 2-(4-hydroxybenzyl) benzoate, hydrochloride/chloride, hydrobromide/bromide, hydroiodide/iodide, 2-isethionate, lactate, malate, maleate, malonate, methanesulfonate, methyl sulfate, naphthalate, 2-naphthalenesulfonate, nicotinate, nitrate, orotate, oxalate, palmitate, phosphate/hydrogen phosphate/dihydrogen phosphate, pyroglutamate, glucarate, stearate, salicylate, tannate, tartrate, tosylate and trifluoroacetate. Suitable base addition salts are formed from bases that form non-toxic salts. Examples thereof include, but are not limited to: aluminum, arginine, calcium, choline, diethylamine, diethanolamine, glycine, lysine, magnesium, meglumine, ethanolamine, potassium, sodium, tromethamine, and zinc salts. It is also possible to form half salts of acids and bases, such as hemisulfate and hemicalcium salts. For a review of suitable salts, please refer to Handbook of Pharmaceutical Salts: Properties, Selection and Use by Stahl and Wermuth (Wiley-VCH, 2002). Methods for preparing pharmaceutically acceptable salts of the compounds described herein are known to those skilled in the art.

Certain compounds of the invention may exist in unsolvated form as well as solvated forms, including hydrated forms. In general, the compounds of formula (I), whether present in solvated form or in unsolvated form, are included within the scope of the invention.

Certain compounds of the invention may exist in different crystalline or amorphous forms, and the compounds of formula (I) present in any forms, are included within the scope of the invention.

To avoid ambiguity, the definitions of some terms used herein are given below. Unless otherwise stated, the meanings of the terms used herein are as follows.

The term "pharmaceutically acceptable" means that the corresponding compound, carrier or molecule is suitable for administration to humans. Preferably, the term refers to it is approved by regulatory agencies such as CFDA (China), EMEA (Europe), FDA (United States), and other national regulatory agencies to be suitable for mammals, preferably humans.

The "prodrug" refers to a derivative that is converted into a compound of the present disclosure by a reaction with enzymes, gastric acid, and the like in the living body under physiological conditions, for example, through oxidation, reduction, hydrolysis, and the like catalyzed by enzymes.

The "metabolite" refers to all molecules derived from any compound of the present disclosure in a cell or organism, preferably a human.

The term "hydroxy" refers to —OH.

The term "halogen" or "halo" refers to —F, —Cl, —Br, or —I.

The term "cyano" refers to —CN.

In the present disclosure, when there are multiple substituents of a certain type, each substituent is independently selected from each other, and these substituents may be the same or different. For example, when there are 2, 3, or 4 $R_1$s, these $R_1$s may be the same or different. For example, when there are 2, 3, or 4 $R_2$s, these $R_2$s may be the same or different. For example, when $R_1$ and $R_2$ are both $—N(R_9)(R_{10})$, $R_9$ and $R_{10}$ contained in $R_1$ and $R_2$ can be independently selected, that is, $R_9$ in $R_1$ and $R_9$ in $R_2$ can be the same or different, and $R_{10}$ in $R_1$ and $R_{10}$ in $R_2$ may be the same or different. For example, when there are two $R_1$s, and the two $R_1$s are both $—N(R_9)(R_{10})$, $R_9$ and $R_{10}$ in the two $R_1$s can be selected independently, that is, $R_9$ in the first $R_1$ and $R_9$ in the second $R_1$ may be the same or different, and $R_{10}$ in the first $R_1$ and $R_{10}$ in the second $R_1$ may be the same or different. The above statement applies to $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$.

As used herein, the term "substituted" means that one or more (preferably 1 to 5, more preferably 1 to 3) hydrogen atoms in a group are independently replaced by a corresponding number of substituents.

As used herein, the term "independently" means that when the number of substituents is more than one, these substituents may be the same or different.

As used herein, the term "optional" or "optionally" means that the event described therein may or may not occur. For example, an "optionally substituted" group means that the group may be unsubstituted or substituted.

As used herein, the term "heteroatom" as used herein refers to oxygen (O), nitrogen (N), or $S(O)_m$ in which m may be 0, 1 or 2, i.e. a sulfur atom S, or a sulfoxide group SO, or a sulfonyl group $S(O)_2$).

As used herein, the term "alkyl" refers to saturated aliphatic hydrocarbons, including straight and branched chains. In some embodiments, the alkyl group has 1-8, or 1-6, or 1-3 carbon atoms. For example, the term "$C_{1-8}$ alkyl" refers to a straight or branched chain group of atoms having 1-8 carbon atoms. The term "$C_{1-8}$ alkyl" includes the terms "$C_{1-6}$ alkyl", "$C_1$-$C_3$ alkyl" and "$C_1$-$C_4$ alkyl" in its definition. Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. The alkyl group may be optionally substituted with one or more (for example, 1 to 5) suitable substituent(s).

As used herein, the term "alkenyl" refers to an aliphatic hydrocarbon having at least one carbon-carbon double bond, including straight and branched chains having at least one carbon-carbon double bond. In some embodiments, alkenyl groups have 2-8 carbon atoms, 2-6 carbon atoms, 3-6 carbon atoms, or 2-4 carbon atoms. For example, the term "$C_{2-8}$ alkenyl" refers to a linear or branched unsaturated atomic group (having at least one carbon-carbon double bond) having 2-8 carbon atoms. The double bond may or may not be the point of attachment of another group. Alkenyl groups include, but are not limited to, vinyl, 1-propenyl, 2-propenyl, 2-methyl-2-propenyl, butenyl, pentenyl, 3-hexenyl, and the like. Alkenyl groups may be optionally substituted with one or more (for example, 1 to 5) suitable substituent(s). When the compound of formula (I) contains an alkenyl group, the alkenyl group may be present in the pure E form, the pure Z form, or any mixture thereof.

As used herein, the term "alkynyl" refers to an aliphatic hydrocarbon having at least one carbon-carbon triple bond, including straight and branched chains having at least one carbon-carbon triple bond. In some embodiments, an alkynyl group has 2-8 carbon atoms, 2-6 carbon atoms, 3-6 carbon atoms, or 2-4 carbon atoms. For example, the term "$C_{2-8}$ alkynyl" refers to a linear or branched unsaturated atomic group (having at least one carbon-carbon triple bond) having 2-8 carbon atoms. The triple bond may or may not be the point of attachment of another group. Alkynyl groups include, but are not limited to, ethynyl, 1-propynyl, 2-propynyl, 2-methyl-2-propynyl, butynyl, pentynyl, 3-hexynyl, and the like. The alkynyl group may be optionally substituted with one or more (for example, 1 to 5) suitable substituent(s).

As used herein, the term "$C_{3-7}$ cycloalkyl" refers to a cycloalkyl group having 3-7 carbon atoms forming a ring, such as cyclopropyl, cyclobutyl, cyclopentyl, cyclohexyl, cyclohexenyl, cycloheptyl. The cycloalkyl may be optionally substituted with one or more suitable substituent(s).

As used herein, the term "n-membered heterocycloalkyl" refers to a cycloalkyl group having m ring-forming carbon atoms and (n-m) ring-forming heteroatoms, the heteroatoms being selected from O, S and N. For example, 3-7 membered heterocycloalkyl includes, but not limited to, oxetane, thietane, azetidine, tetrahydrofuran, tetrahydrothiophene, pyrrolidine, tetrahydropyran, tetrahydrothiopyran, piperidine, morpholine, piperazine, oxepane, thiepane, and azepine. The heterocycloalkyl may be optionally substituted with one or more suitable substituent(s).

As used herein, the term "$C_{5-7}$ aryl" refers to an aryl group having an aromatic ring containing 5-7 carbon atoms, preferably phenyl.

As used herein, the term "n-membered heteroaryl" refers to a heteroaryl group having m carbon atoms forming an aromatic ring and (n-m) heteroatoms forming an aromatic ring, the heteroatoms being selected from O, S and N. For example, 5-7 membered heteroaryl includes but not limited to pyrazine, pyrazole, pyrrole, furan, thiophene, thiazole, and pyridine. The heteroaryl may be optionally substituted with one or more suitable substituent(s).

As used herein, the term "$C_{7-11}$ bicyclic aryl" refers to a bicyclic aryl group having 7-11 carbon atoms, such as naphthalene, indene and the like. The bicyclic aryl may be optionally substituted with one or more suitable substituent(s).

As used herein, the term "n-membered bicyclic heteroaryl" refers to a bicyclic heteroaryl group having m carbon atoms forming an aromatic bicyclic ring and (n-m) heteroatoms forming an aromatic bicyclic ring, and the heteroatoms are selected from O, S and N. For example, 7-11 membered bicyclic heteroaryl includes, but not limited to, quinoline, isoquinoline, benzothiazole, and the like. The bicyclic heteroaryl may be optionally substituted with one or more suitable substituent(s).

As used herein, the term "11-15 membered tricyclyl" includes but not limited to acridine and the like. The 11-15 membered tricyclyl may be optionally substituted with one or more suitable substituent(s).

As used herein, the term "haloalkyl" refers to an alkyl group having one or more halogen substituent(s) (up to perhaloalkyl, that is, each hydrogen atom of the alkyl is replaced by a halogen atom). For example, the term "$C_{1-6}$ haloalkyl" refers to a $C_{1-6}$ alkyl group with one or more halogen substituent(s) (up to perhaloalkyl, that is, each hydrogen atom of the alkyl group is replaced by a halogen atom). As another example, the term "$C_{1-4}$ haloalkyl" refers to a $C_{1-4}$ alkyl group with one or more halogen substituent(s) (up to perhaloalkyl, that is, each hydrogen atom of the alkyl group is replaced by a halogen atom); the term "$C_{1-3}$ haloalkyl" refers to a $C_{1-3}$ alkyl group with one or more halogen substituent(s) (up to perhaloalkyl, that is, each hydrogen atom of the alkyl group is replaced by a halogen atom); and the term "$C_{1-2}$ haloalkyl" refers to a $C_{1-2}$ alkyl group (i.e. methyl or ethyl) with one or more halogen substituent(s) (up to perhaloalkyl, that is, each hydrogen atom of the alkyl group is replaced by a halogen atom). As another example, the term "$C_1$ haloalkyl" refers to a methyl group with 1, 2, or 3 halogen substituent(s). Examples of haloalkyl groups include: $CF_3$, $C_2F_5$, $CHF_2$, $CH_2F$, $CH_2CF_3$, $CH_2Cl$, and the like.

As used herein, the term "alkoxy" refers to alkyl with a single bond attached to an oxygen atom. The point of attachment of the alkoxy group to a molecule is through the oxygen atom. Alkoxy can be described as alkyl-O—. The term "$C_{1-6}$ alkoxy" refers to a linear or branched alkoxy group containing 1 to 6 carbon atoms. The term "$C_{1-6}$ alkoxy" includes the term "$C_{1-3}$ alkoxy" in its definition. Alkoxy includes, but not limited to, methoxy, ethoxy, propoxy, isopropoxy, butoxy, hexoxy, and the like. The alkoxy group may be optionally substituted with one or more suitable substituent(s).

Herein, a numerical range relating to the number of substituents, the number of carbon atoms, or the number of ring members represents an enumeration of all integers in the range, and the range is only a simplified representation thereof. For example:

"1-4 substituent(s)" means 1, 2, 3 or 4 substituent(s);

"1-3 substituent(s)" means a 1, 2 or 3 substituent(s);

"3 to 12-membered ring" means a 3, 4, 5, 6, 7, 8, 9, 10, 11 or 12-membered ring;

"3 to 8 membered ring" means a 3, 4, 5, 6, 7, or 8 membered ring;

"1-12 carbon atoms" or "$C_{1-12}$" means 1 ($C_1$), 2 ($C_2$), 3 ($C_3$), 4 ($C_4$), 5 ($C_5$), 6 ($C_6$), 7 ($C_7$), 8 ($C_8$), 9 ($C_9$), 10 ($C_{10}$), 11 ($C_{11}$) or 12 ($C_{12}$) carbon atoms;

"1-6 carbon atoms" or "$C_{1-6}$" means 1 ($C_1$), 2 ($C_2$), 3 ($C_3$), 4 ($C_4$), 5 ($C_5$) or 6 ($C_6$) carbon atoms;

"1-4 carbon atoms" or "$C_{1-4}$" means 1 ($C_1$), 2 ($C_2$), 3 ($C_3$), 4 ($C_4$) carbon atoms;

"2-6 carbon atoms" or "$C_{2-6}$" means 2 ($C_2$), 3 ($C_3$), 4 ($C_4$), 5 ($C_5$) or 6 ($C_6$) carbon atoms;

"$C_{3-8}$" means 3 ($C_3$), 4 ($C_4$), 5 ($C_5$), 6 ($C_6$), 7 ($C_7$), 8 ($C_8$) carbon atoms; and "3 to 8 ring members" means 3, 4, 5, 6, 7, or 8 ring members.

Thus, a numerical range associated with the number of substituents, the number of carbon atoms, or the number of ring members also encompasses any one of its subranges, and each subrange is also considered to be disclosed herein.

In a second aspect, the present disclosure provides a pharmaceutical composition comprising the above mentioned compounds, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, and one or more pharmaceutically acceptable carriers, adjuvants or excipients.

The pharmaceutical compositions of the invention may be formulated as suitable dosage forms for oral, external (including not limited to external application, spraying, and the like), parenteral (including subcutaneous, intramuscular, intradermal and intravenous), bronchial or nasal administration as desire. Preferably, the pharmaceutical compositions of the invention may be formulated as suitable dosage forms for oral or external administration. More preferably, the pharmaceutical compositions of the invention may be formulated as suitable dosage forms for oral administration.

If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, paste, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula (I) according to the present disclosure.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

These compositions may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylatedisostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of the invention include paste, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The external dosage form of the compound of the present disclosure may be in the form of a water-in-oil (W/O) or oil-in-water (O/W) emulsion, a multi-emulsion form, such as a water-in-oil-in-water (W/O/W) form or an oil-in-water-oil (O/W/O) emulsion, or in the form of water dispersion or lipid dispersion, gel or aerosol.

The external dosage form of the compound of the present disclosure may contain additives and aids, such as emulsifiers, thickeners, gelling agents, water fixatives, spreading agents, stabilizers, dyes, fragrances, and preservatives. Suitable emulsifiers include stearic acid, triethanolamine and PEG-40-stearate. Suitable thickeners include glyceryl monostearate and PEG600. Suitable preservatives include propyl paraben and chlorocresol. Suitable spreading agents include dimethicone and polydimethylcyclosiloxane. Suitable water fixatives include polyethylene glycol, preferably polyethylene glycol 600.

The external dosage form of the compound of the present disclosure may include pastes, lotions, gels, emulsions, microemulsions, sprays, skin patches, and the like, which can be applied topically to treat atopic dermatitis, eczema, psoriasis, and scleroderma, itching, vitiligo, hair loss and other skin diseases. In particular, the external dosage form of the compound of the present disclosure is pastes, which can be applied topically to treat skin diseases such as atopic dermatitis, eczema, psoriasis, scleroderma, itching, vitiligo, and hair loss and other skin diseases.

The amount of the compound of formula (I) in the pharmaceutical composition and dosage form can be appropriately determined by those skilled in the art as needed. For example, the compound of formula (I) can be present in the pharmaceutical composition or dosage form in a therapeutically effective amount.

In a third aspect, the present disclosure provides use of the compound as described above, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, or the composition as described above in the preparation of a medicament for the treatment and/or prevention of JAK-related diseases or disorders.

"Diseases or disorders related to JAK" include but not limited to:

Arthritis, including rheumatoid arthritis, juvenile arthritis and psoriatic arthritis;

Autoimmune diseases or disorders, including single organ or single cell type autoimmune disorders, such as Hashimoto's thyroiditis, autoimmune hemolytic anemia, pernicious anemia of autoimmune atrophic gastritis, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those involving systemic autoimmune disorders (e.g. systemic lupus erythematosus, rheumatoid arthritis, Sjogren's syndrome, Reiter's syndrome, polymyositis-dermatomyositis, systemic sclerosis, polyarteritis nodosa, multiple sclerosis and bullous pemphigoid) and other O-cell (humoral) or T-cell autoimmune diseases (including Kogan syndrome), ankylosing spondylitis, Wegener's Granuloma, autoimmune alopecia, type I diabetes or juvenile-onset diabetes or thyroiditis;

Cancer or tumor, including digestive/gastrointestinal cancer, colorectal cancer, liver cancer, skin cancer (including mast cell tumor and squamous cell carcinoma), breast cancer, ovarian cancer, prostate cancer, lymphoma, leukemia (including acute myeloid leukemia and chronic myeloid leukemia), kidney cancer, lung cancer, muscle cancer, bone cancer, bladder cancer, brain cancer, melanoma (including oral and metastatic melanoma), Kaposi's sarcoma, myeloma (including multiple myeloma), myeloproliferative disorders, proliferative diabetic retinopathy or disorders related to angiogenesis (including solid tumors);

Diabetes, including type I diabetes or diabetic complications;

Eye diseases, disorders or conditions, including autoimmune diseases of eyes, keratoconjunctivitis, vernal conjunctivitis, uveitis (including uveitis and lens uveitis related to Behcet's disease), keratitis, herpetic keratitis, keratitis conus, corneal epithelial dystrophy, leukoplakia, ocular pemphigus, Moran ulcer, scleritis, Grave's eye disease, Vogt-Koyanagi-Harada syndrome, keratoconjunctivitis sicca (dry eye), blisters, iridocyclitis, sarcoidosis, endocrine ophthalmopathy, sympathetic ophthalmia, allergic conjunctivitis, or ocular neovascularization;

Intestinal inflammation, allergies or conditions, including Crohn's disease and/or ulcerative colitis, inflammatory bowel disease, celiac disease, proctitis, eosinophilic gastroenteritis or mastocytosis;

Neurodegenerative diseases, including motor neuron disease, Alzheimer's disease, Parkinson's disease, amyotrophic lateral sclerosis, Huntington's disease, neurodegenerative disease caused by cerebral ischemia or traumatic injury, stroke, glutamate neurotoxicity or hypoxia; stroke ischemia/reperfusion injury, myocardial ischemia, renal ischemia, heart attack, cardiac hypertrophy, atherosclerosis and arteriosclerosis, organ hypoxia or platelet aggregation;

Skin diseases, conditions or disorders, including atopic dermatitis, eczema, psoriasis, scleroderma, itching or other pruritic conditions, vitiligo, hair loss;

Allergies, including mammalian allergic dermatitis (including equine allergic diseases, such as bite allergies), summer eczema, Culex mosquito itch syndrome (sweet itch), emphysema, inflammatory airway disease, recurrent airway obstruction, airway overreaction, or chronic obstructive pulmonary disease;

Asthma and other obstructive airway diseases, including chronic or refractory asthma, advanced asthma, bronchitis, bronchial asthma, allergic asthma, endogenous asthma, exogenous asthma or dusty asthma; and Transplant rejection, including islet transplant rejection, bone marrow transplant rejection, graft versus host disease, organ and cell transplant rejection (for example bone marrow, cartilage, cornea, heart, intervertebral disc, pancreatic islets, kidney, limbs, liver, lung, muscle, myoblasts, nerve, pancreas, skin, small intestine or trachea) or xenotransplantation.

In a fourth aspect, the present disclosure provides a method for treating JAK-related diseases or disorders, the method comprising administrating a therapeutically effective amount of the compound as described above or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, or the composition as described above to patients in need. Among them, the patient is preferably a mammal, and more preferably a human patient. The route of administration can be oral, topical (including but not limited to external application, spraying, and the like), parenteral (including subcutaneous, intramuscular, cortical, and intravenous) administration, bronchial administration, or nasal administration. Among them, it is preferably administered orally or topically. It is more preferably administered orally.

Unexpectedly, the compound of the present disclosure demonstrated excellent efficacy as a JAK kinase inhibitor in experiments that is superior to existing JAK kinase inhibitors, such as Filgotinib, and had good safety potentially.

The present invention will be further illustrated and described below in conjunction with the drawings and specific examples.

EXAMPLES

The compounds of formula (I) of the present disclosure can be synthesized by various methods familiar to those skilled in the art of organic synthesis. The following specific examples give some exemplary synthesis methods of the compounds of formula (I), and these methods are well-known in the field of synthetic chemistry. Obviously, referring to the exemplary embodiments of the present application, those skilled in the art can appropriately adjust reactants, reaction conditions, and protective groups to easily design other synthetic routes for compounds of formula (I).

The following further describes the present disclosure in conjunction with examples. Nevertheless, these examples do not limit the scope of the present disclosure.

Example 1: N-((2-(6-(2-ethyl-5-fluoro-4-hydroxyphenyl)-1H-indazol-3-yl)-1H-imidazol-4-yl)methyl)-5-(piperidin-1-yl)pyrazine-2-carboxamide (MDI-3)

MDI 3

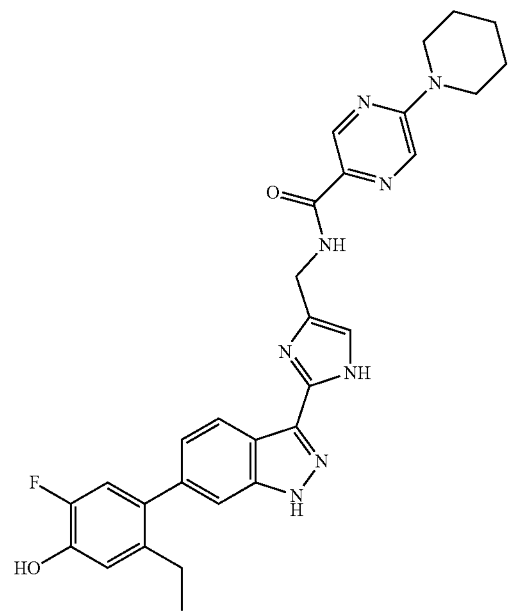

Synthetic Route of Target Compound 16 (i.e., MDI-3)

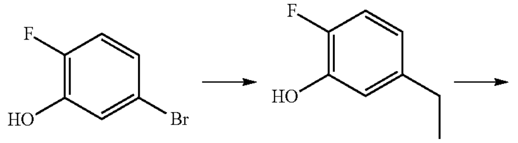

1

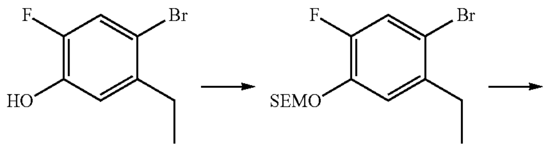

2 3

-continued
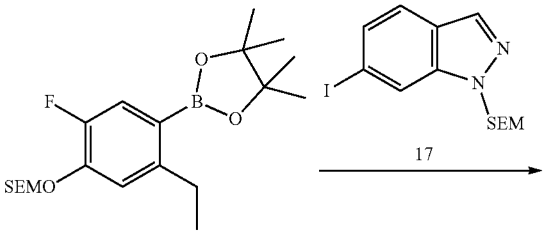
4
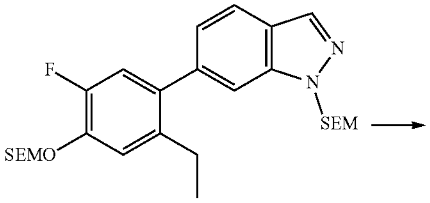
5
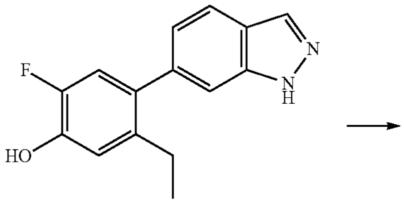
6
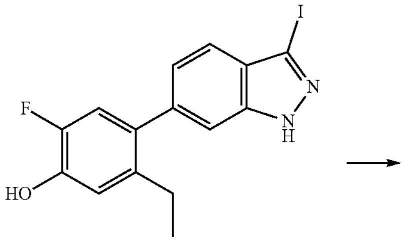
7
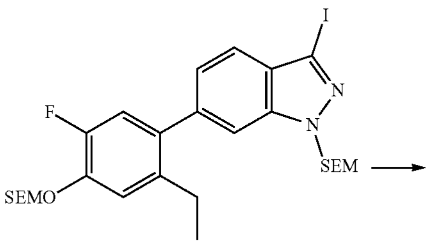
8
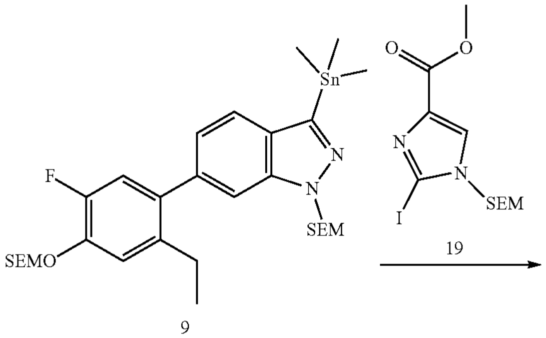
9
-continued
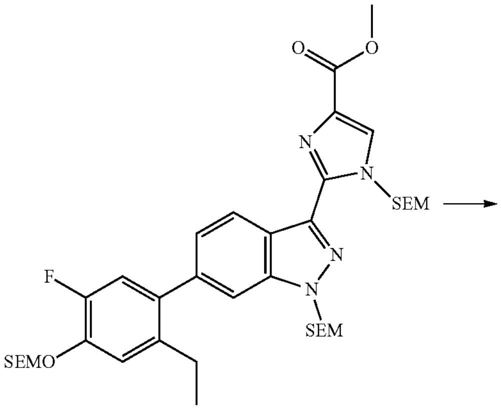
10
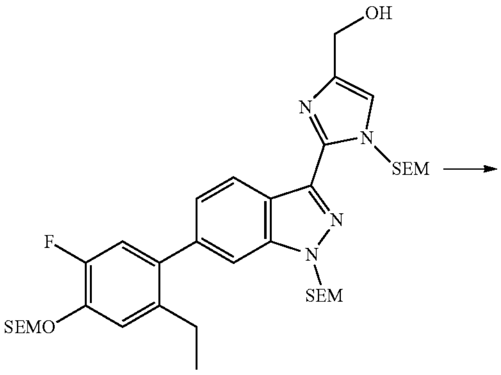
11
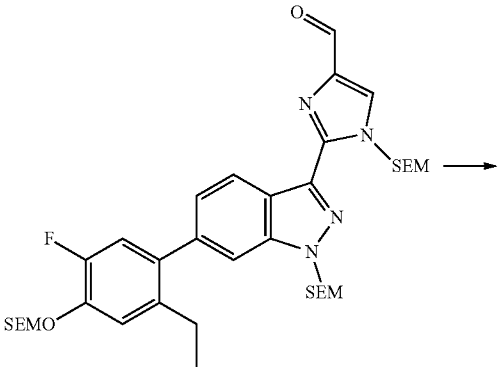
12
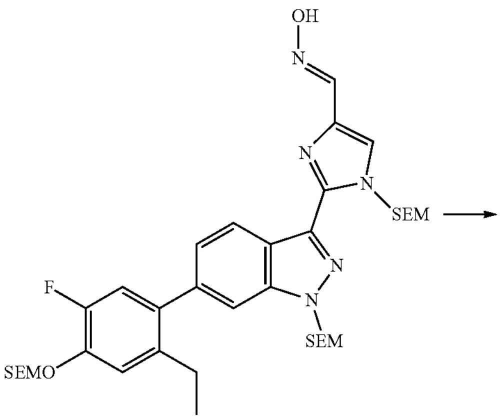
13

-continued

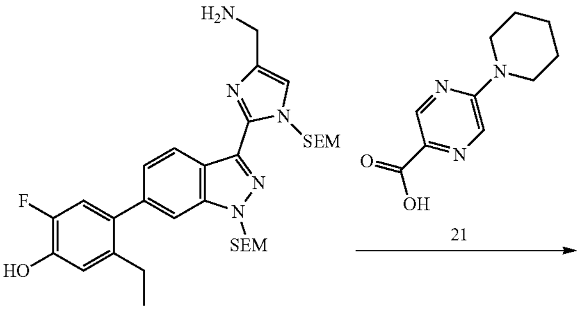

14

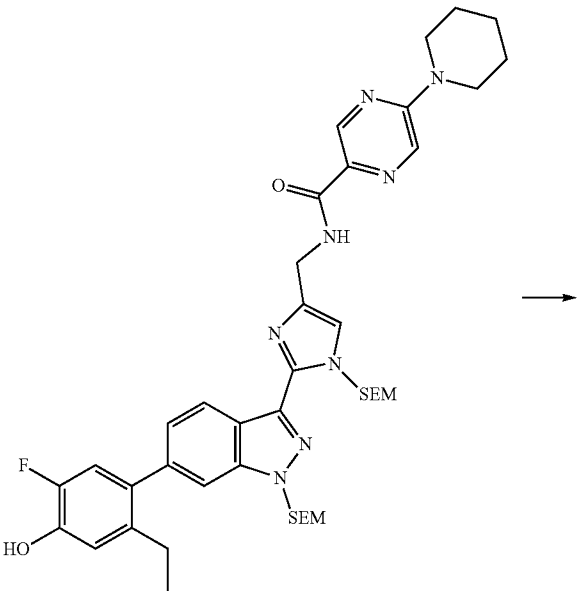

15

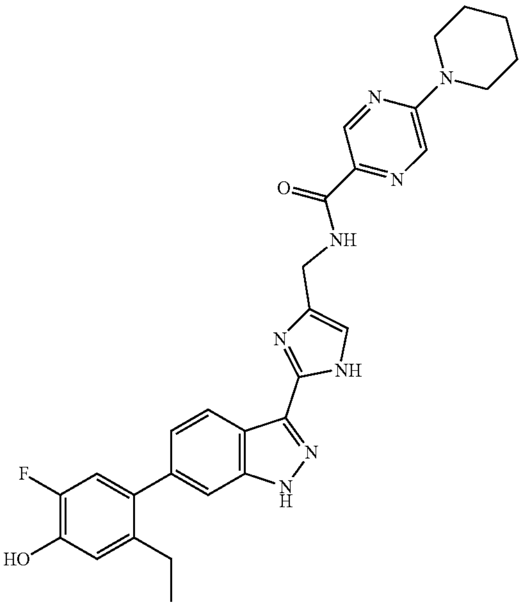

16
MDI 3

Synthetic Route of Intermediate 17

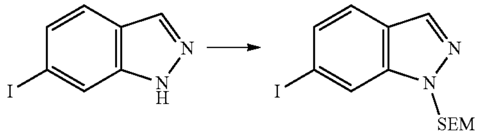

17

Synthetic Route of Intermediate 19

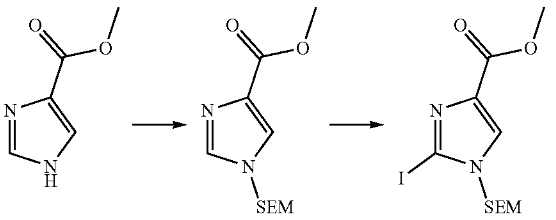

18 19

Synthetic Route of Intermediate 21

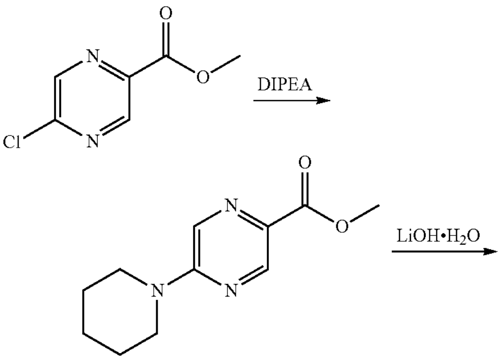

20

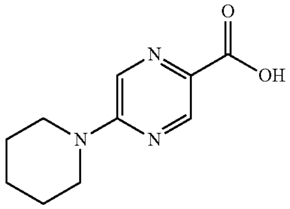

21

Synthesis Method

Synthesis of Intermediate 1: 5-ethyl-2-fluorophenol 5-bromo-2-fluorophenol (200.0 mg, 1.05 mmol) and bis (tri-tert-butylphosphorus) palladium (10.7 mg, 0.02 mmol) was dissolved in 10 ml THF. The atmosphere was replaced with nitrogen, which was repeated 3 times. The temperature was lowered to 10-20° C. 1 mol/L diethyl zinc solution (2.3 ml, 2.30 mmol) was added dropwise. After the addition was completed, the temperature was heated up to 50° C. It was allowed to react overnight, and the temperature was cooled to 0° C. The reaction was quenched with water, and filtered with celite. The celite pad was washed with ethyl acetate. The resulting filtrate was extracted with ethyl acetate, and the organic phases were combined, washed with saturated sodium chloride solution, and dried over anhydrous sodium sulfate. After drying, it was concentrated and separated by column chromatography to afford an oily liquid with a yield of 65.1%.

$^1$H NMR (400 MHz, $CDCl_3$) δ6.97 (d, J=8.0 Hz, 1H), 6.85 (d, J=12.0 Hz, 1H), 6.69-6.65 (m, 1H), 2.61-2.55 (m, 2H), 1.21 (t, J=8.0 Hz, 3H).

Synthesis of Intermediate 2: 4-bromo-5-ethyl-2-fluorophenol

Intermediate 1 (200.1 mg, 1.43 mmol) was dissolved in 6 ml of acetonitrile, to which $CuBr_2$ (957.5 mg, 4.29 mmol) was added. The mixture was stirred at room temperature for 3 hours. The reaction was quenched with water, extracted with ethyl acetate, and the organic phase was washed with saturated sodium chloride solution and dried over anhydrous sodium sulfate. It was concentrated and separated by column chromatography to afford a colorless oil, yield: 78.1%.

$^1$H NMR (400 MHz, CDCl3) δ7.25 (d, J=12.0 Hz, 1H), 6.89 (d, J=12.0 Hz, 1H), 2.69-2.63 (m, 2H), 1.19 (t, J=12.0 Hz, 3H).

Synthesis of Intermediate 3: 2-((4-bromo-5-ethyl-2-fluorophenoxy) methoxy)ethyl)trimethylsilane Intermediate 2 (220.0 mg, 1.00 mmol) was dissolved in 6 ml DCM, DIPEA (130.5 mg, 1.10 mmol) was added, and the temperature was reduced to 0° C. SEMCl (168.2 mg, 1.10 mmol) was added dropwise at 0° C. After the addition, the temperature was raised to room temperature, and it was allowed to react for 8 hours. The reaction was quenched with water, and extracted with DCM. The organic phase was washed with saturated sodium chloride solution, and dried over anhydrous sodium sulfate. It was concentrated to afford a colorless oil, the crude yield: 99.1%.

$^1$H NMR (400 MHz, CDCl3) δ7.26 (d, J=12.0 Hz, 1H), 6.89 (d, J=12.0 Hz, 1H), 5.24 (s, 2H) 3.82-3.78 (m, 2H) 2.67-2.62 (m, 2H), 1.19 (t, J=12.0 Hz, 3H), 0.98-0.94 (m, 2H), 0.01 (s, 9H).

Synthesis of Intermediate 4: (2-((5-ethyl-2-fluoro-4-(4,4,5,5-tetramethyl-1,3,2-dioxaboran-2-yl)phenoxy) methoxy)ethyl)trimethylsilane Intermediate 3 (280.0 mg, 0.80 mmol), pinacol borate (206.1 mg, 0.80 mmol), $Pd(dppf)Cl_2$ (59.2 mg, 0.08 mmol) and KOAc (237.5 mg, 2.40 mmol) were dissolved in 1,4-dioxane (6 ml). The atmosphere was replaced with nitrogen, which was repeated 3 times. The mixture was heated to 100° C. and it was allowed to react overnight. After the reaction was completed, it was quenched with water, extracted with ethyl acetate, and the organic phase was washed with saturated sodium chloride solution, and dried over anhydrous sodium sulfate. It was concentrated and separated by column chromatography to afford a colorless oil, yield: 56.2%.

$^1$H NMR (400 MHz, CDCl3) δ7.48 (d, J=12.0 Hz, 1H), 7.02 (d, J=8.0 Hz, 1H), 5.28 (s, 2H), 3.82-3.78 (m, 2H) 2.89-2.83 (m, 2H), 1.35 (s, 12H), 1.17 (t, J=8.0 Hz, 3H), 0.98-0.94 (m, 2H), 0.01 (s, 9H).

Synthesis of Intermediate 17: 6-iodo-1-((2-(trimethylsilyl)ethoxy)methyl)-1H-indazole The compound 6-iodoindazole (200 mg, 0.82 mmol) and 5 ml of THF were added and the resulting mixture was cooled to 0° C. At 0° C., NaH (32.8 mg (60%), 0.82 mmol) was added to the resulting mixture in batches. After the addition was complete, it was allowed to react at 0° C. for 1 h. Then SEMCl (143.5 mg, 0.86 mmol) was added dropwise. After the addition was complete, the reaction mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a product, yield: 82.2%.

$^1$H NMR (400 MHz, $CDCl_3$) δ8.16 (s, 1H), 8.07 (s, 1H), 8.21 (d, J=1.4 Hz, 1H), 7.47-7.43 (m, 1H), 5.69 (s, 2H), 3.63-3.58 (m, 2H), 0.96-0.91 (m, 2H), −0.04 (s, 9H).

Synthesis of Intermediate 5: 6-(2-ethyl-5-fluoro-4-((2-(trimethylsilyl) ethoxy)methoxy)phenyl)-1-((2-(trimethylsilyl)ethoxy)methyl)-1H-indazole Under $N_2$ protection, intermediate 4 (85 mg, 0.21 mmol), intermediate 17 (80 mg, 0.21 mmol), Pd(dppf)Cl (15.6 mg, 0.021 mmol), $K_3PO_4$ (136.3 mg, 0.64 mmol), and 1,4-dioxane (2 ml) were added. After the addition was complete, the mixture was heated to 100° C. and it was allowed to react overnight. After the reaction was completed, it was quenched with water, extracted with EA, and the organic phase was washed with saturated sodium chloride solution, and dried over anhydrous sodium sulfate. It was concentrated and separated by column chromatography to afford a colorless oil 66.9 mg, yield: 60.6%.

$^1$H NMR (400 MHz, $CDCl_3$) δ8.14 (s, 1H), 7.69 (d, J=8.0 Hz, 1H), 7.61 (s, 1H), 7.15 (d, J=8.0 Hz, 1H), 7.05-7.01 (m, 2H), 5.74 (s, 2H), 5.31 (s, 2H), 3.88-3.84 (m, 2H), 3.70-3.65 (m, 2H), 2.61-2.52 (m, 2H), 1.09 (t, J=8.0 Hz, 3H), 1.03-0.96 (m, 4H), 0.01 (s, 9H), −0.03 (s, 9H).

Synthesis of Intermediate 6: 5-ethyl-2-fluoro-4-(1H-indazol-6-yl)phenol

Intermediate 5 (30 mg, 0.12 mmol), 2 ml of methanol, and 1 ml of concentrated hydrochloric acid were added. After the addition was complete, the reaction mixture was heated to 60° C. and it was allowed to react. After the reaction was completed, saturated $NaHCO_3$ solution was added to adjust pH=7, and the resulting mixture was extracted with EA, and the organic phase was washed with saturated sodium chloride solution, and dried over anhydrous sodium sulfate. It was concentrated and separated by column chromatography to afford a white solid 12 mg, yield: 80.6%.

$^1$H NMR (400 MHz, MeOD) δ8.08 (d, J=1.1 Hz, 1H), 7.79 (dd, J=0.8 Hz, J=8.3 Hz, 1H), 7.42-7.40 (m, 1H), 7.08 (dd, J=1.4 Hz, J=8.3 Hz, 1H), 6.95-6.88 (m, 2H), 2.58-2.51 (m, 2H), 1.06 (t, J=8.0 Hz 3H).

Synthesis of Intermediate 7: 5-ethyl-2-fluoro-4-(3-iodo-1H-indazol-6-yl)phenol Intermediate 6 (134 mg, 0.52 mmol), 2 ml DMF, and KOH (117 mg, 2.08 mmol) were added. After the addition was complete, it was allowed to cool to 0° C. At 0° C., $I_2$ (132 mg, 0.52 mmol) in DMF (2 ml) was added dropwise. After the dropwise addition was completed, the reaction mixture was raised to room temperature and it was allowed to react. After the reaction was completed, 1M HCl was added to adjust pH=7, and the resulting mixture was extracted with EA, and the organic phase was washed with saturated sodium chloride solution, and dried over anhydrous sodium sulfate. It was concentrated and separated by column chromatography to afford a white solid 150 mg, yield: 75.5%.

$^1$H NMR (400 MHz, $CDCl_3$) δ7.52 (dd, J=0.8 Hz, J=8.3 Hz, 1H), 7.35 (t, J=1.1 Hz, 1H), 7.15 (dd, J=1.3 Hz, J=8.4 Hz, 1H), 6.98-6.94 (m, 2H), 2.50 (q, J=7.6 Hz, 2H), 1.06 (t, J=7.6 Hz, 3H).

Synthesis of Intermediate 8: 6-(2-ethyl-5-fluoro-4-((2-(trimethylsilyl) ethoxy)methoxy)phenyl)-3-iodo-1-((2-(trimethylsilyl)ethoxy)methyl)-1H-indazole The intermediate 7 (180 mg, 0.47 mmol) and 4 ml of DMF were added and the resulting mixture was cooled to 0° C. At 0° C., NaH (37.6 mg (60%), 0.94 mmol) was added to the resulting mixture in batches. After the addition was complete, it was stirred for 1 hour. Then at 0° C., SEMCl (143.5 mg, 0.86 mmol) was added dropwise. After the addition was complete, the reaction mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 220 mg, yield: 72.9%.

$^1$H NMR (400 MHz, $CDCl_3$) δ7.52-7.41 (m, 2H), 7.23-7.12 (m, 2H), 7.02-6.97 (m, 1H), 5.73 (s, 2H), 5.30 (s, 2H), 3.88-3.81 (m, 2H), 3.67-3.55 (m, 2H), 2.56-2.48 (m, 2H), 1.06 (t, J=8.0 Hz, 3H), 1.03-0.96 (m, 4H), 0.03 (s, 9H), −0.07 (s, 9H).

Synthesis of Intermediate 9: 6-(2-ethyl-5-fluoro-4-((2-(trimethylsilyl) ethoxy)methoxy)phenyl)-1-((2-(trimethylsilyl)ethoxy)methyl)-3-(trimethylstannyl)-1H-indazole Under the protection of $N_2$, intermediate 8 (20 mg, 0.031 mmol), $Sn_2Me_6$ (20.3 mg, 0.062 mmol), $Pd(PPh_3)_4$ (3.6 mg, 0.0031 mmol), and 5 ml of anhydrous toluene were added. After the addition was completed, the reaction mixture was raised to 80° C. and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 14.8 mg, yield: 70.2%.

$^1$H NMR (400 MHz, $CDCl_3$) δ7.72 (d, J=8.0 Hz, 1H), 7.45 (s, 2H), 7.15 (d, J=8.0 Hz, 1H), 7.08 (dd, J=4.0 Hz, J=8.0 Hz, 1H), 6.99 (d, J=12.0 Hz, 1H), 5.77 (s, 2H), 5.31 (s, 2H), 3.88-3.84 (m, 2H), 3.60-3.56 (m, 2H), 2.55 (q, J=8.0 Hz, 2H), 1.07 (t, J=8.0 Hz, 3H), 1.02-0.98 (m, 2H), 0.90-0.85 (m, 2H), 0.48 (s, 9H), 0.03 (s, 9H), −0.07 (s, 9H).

Synthesis of Intermediate 19: Methyl 2-iodo-1-((2-(trimethylsilyl)ethoxy methyl)-1H-imidazole-4-carboxylate

1. Synthesis of Intermediate 18: Methyl 1-((2-(trimethylsilyl)ethoxy) methyl)-1H-imidazole-4-carboxylate Compound methyl 1H-imidazole-4-carboxylate (Ig, 7.9 mmol), $K_2CO3$ (2.74 g, 19.8 mmol), and 20 ml DMF were added and then SEMCl (1.71 g, 10.2 mmol) was added dropwise. After the dropwise addition was complete, the reaction mixture was heated to 80° C. After the reaction was completed, it was quenched with water, extracted with EA, and the resulting organic phase was washed with saturated sodium chloride solution, and dried over anhydrous sodium sulfate. It was concentrated and separated by column chromatography to afford a product 750 mg, yield: 37.1%.

$^1$H NMR (400 MHz, $CDCl_3$) δ7.68 (s, 1H), 7.58 (s, 1H), 5.26 (s, 2H), 3.84 (s, 3H), 3.48-3.43 (m, 2H), 0.88-0.83 (m, 2H), −0.05 (s, 9H).

2. Synthesis of Intermediate 19: methyl 2-iodo-1-((2-(trimethylsilyl)ethoxy) methyl)-1H-imidazole-4-carboxylate Intermediate 18 (4 g, 15.6 mmol), NIS (7 g, 31.1 mmol), AIBN (0.26 g, 1.58 mmol), 20 ml $CHCl_3$ were added and the reaction mixture was warmed to 65° C. After the reaction was complete, it was allowed to cool to room temperature. The reaction was quenched with 5% aqueous solution of sodium thiosulfate, extracted with DCM, and the resulting organic phase was washed with saturated sodium chloride solution, and dried over anhydrous sodium sulfate. It was concentrated and separated by column chromatography to afford a product 3 g, yield: 50.2%.

$^1$H NMR (400 MHz, $CDCl_3$) δ7.80 (s, 1H), 5.26 (s, 2H), 3.89 (s, 3H), 3.58-3.52 (m, 2H), 0.95-0.85 (m, 2H), −0.01 (s, 9H).

Synthesis of Intermediate 10: Methyl 2-(6-(2-ethyl-5-fluoro-4-((2-(trimethylsilyl)ethoxy)methoxy)phenyl)-1-((2-(trimethylsilyl)ethoxy)methyl)-1H-indazol-3-methyl)-1-((2-(trimethylsilyl)ethoxy) Methyl)-1H-imidazole-4-carboxylic acid Under the protection of $N_2$, Intermediate 9 (40 mg, 0.059 mmol), Intermediate 19 (22.4 mg, 0.059 mmol), CuI (2.23 mg, 0.012 mmol), $Pd(PPh_3)_4$ (6.8 mg, 0.0059 mmol), and 4 ml THF were added. After the addition was completed, the reaction mixture was heated to 65° C. and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 14 mg, yield: 30.8%.

$^1$H NMR (400 MHz, $CDCl_3$) δ8.57 (d, J=8.0 Hz, 1H), 7.92 (s, 1H), 7.45 (s, 1H), 7.25 (dd, J=1.2 Hz, J=8.4 Hz, 1H), 7.16 (d, J=8.0 Hz, 1H), 7.02 (d, J=12.0 Hz, 1H), 5.96 (s, 2H), 5.76 (s, 2H), 5.31 (s, 2H), 3.96 (s, 3H), 3.88-3.84 (m, 2H), 3.61-3.57 (m, 4H), 2.53 (q, J=8.0 Hz, 2H), 1.05 (t, J=8.0 Hz, 3H), 1.03-0.98 (m, 2H), 0.92-0.87 (m, 4H), 0.03 (s, 9H), −0.07 (s, 9H), −0.08 (s, 9H).

Synthesis of Intermediate 11: (2-(6-(2-ethyl-5-fluoro-4-((2-(trimethylsilyl) ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl) methanol Under the protection of $N_2$, intermediate 10 (22 mg, 0.028 mmol) and 4 ml of THF were added, and the resulting mixture was lowered to −78° C. At −78° C., DIBAL-H (0.038 ml, 1.5 Mol/L, 0.057 mmol) was added. After the addition was completed, the reaction mixture was heated to room temperature and it was allowed to react. After the reaction was completed, it was cooled to 0° C. and quenched with water, passed through diatomaceous earth, and rinsed with EA. The filtrate was extracted with EA, and the organic phase was washed with saturated sodium chloride solution and dried over anhydrous sodium sulfate. It was concentrated and separated by column chromatography to afford a colorless oil 17 mg, yield: 81.8%.

$^1$H NMR (400 MHz, $CDCl_3$) δ8.48 (d, J=8.0 Hz, 1H), 7.46 (s, 1H), 7.23 (d, J=8.0 Hz, 1H), 7.18-7.15 (m, 2H), 7.02 (d, J=12.0 Hz, 1H), 5.92 (s, 2H), 5.76 (s, 2H), 5.32 (s, 2H), 4.75 (s, 2H), 3.88-3.84 (m, 2H), 3.62-3.55 (m, 4H), 2.54 (q, J=8.0 Hz, 2H), 1.06 (t, J=8.0 Hz, 3H), 1.04-0.98 (m, 2H), 0.92-0.86 (m, 4H), 0.04 (s, 9H), −0.07 (s, 9H), −0.08 (s, 9H).

Synthesis of Intermediate 12: 2-(6-(2-ethyl-5-fluoro-4-((2-(trimethylsilyl) ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde Intermediate 11 (12 mg, 0.016 mmol), 4 ml of $CHCl_3$, and $MnO_2$ (57.4 mg, 0.66 mmol) were added, and the resulting mixture was heated to 60° C. and it was allowed to react. After the reaction was completed, the reaction mixture was then lowered to room temperature, passed through celite, and washed with DCM. The filtrate was washed with saturated sodium chloride solution and dried over anhydrous sodium sulfate. It was concentrated and separated by column chromatography to afford a colorless oil 10 mg, yield: 84.4%.

$^1$H NMR (400 MHz, $CDCl_3$) δ10.04 (s, 1H), 8.59 (d, J=8.0 Hz, 1H), 7.95 (s, 1H), 7.48 (s, 1H), 7.29 (dd, J=4.0 Hz, J=8.0 Hz, 1H), 7.17 (d, J=8.0 Hz, 1H), 7.02 (d, J=12.0 Hz, 1H), 6.03 (s, 2H), 5.77 (s, 2H), 5.32 (s, 2H), 3.88-3.84 (m, 2H), 3.64-3.59 (m, 4H), 2.55 (q, J=8.0 Hz, 2H), 1.06 (t, J=8.0 Hz, 3H), 1.04-0.99 (m, 2H), 0.93-0.88 (m, 4H), 0.04 (s, 9H), −0.06 (s, 9H), −0.07 (s, 9H).

Synthesis of Intermediate 13: 2-(6-(2-ethyl-5-fluoro-4-((2-(trimethylsilyl) ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde oxime Intermediate 12 (10 mg, 0.016 mmol), TEA (1.68 mg, 0.017 mmol), 2 ml of DCM were added and the resulting mixture was cooled to 0° C., to which hydroxylamine hydrochloride (1.15 mg, 0.017 mmol) were added in batches. After the addition was complete, the reaction mixture was raised to room temperature and it was allowed to react. After the reaction was completed, the reaction mixture was quenched with water, and extracted with DCM. The layers were separated and the organic phase was washed with saturated sodium chloride solution and dried over anhydrous sodium sulfate. It was concentrated to obtain 7 mg of colorless oil, which was directly used in the next reaction, yield: 68.4%.

Synthesis of Intermediate 14: 4-(3-(4-(aminomethyl)-1-((2-(trimethylsilyl) ethoxy)methyl)-1H-imidazol-2-yl)-1-((2-(trimethylsilyl)ethoxy)methyl)-1H-indazol-6-yl)-5-ethyl-2-fluorophenol Intermediate 13 (10 mg, 0.013 mmol), Pd/C (2 mg), 2 ml of MeOH, and catalytic amount of HCl were added, and the atmosphere was replaced with $H_2$ three times. The reaction was carried out at room temperature (H2 pressure 1 atm). After the reaction was completed, the system was passed through diatomaceous earth. It was concentrated and separated by column chromatography to afford a colorless oil 5 mg, yield: 63.0%.

$^1$H NMR (400 MHz, $CDCl_3$) δ 8.39 (d, J=8.0 Hz, 1H), 7.42 (s, 1H), 7.13-7.10 (m, 2H), 6.96-6.91 (m, 2H), 5.89 (s, 2H), 5.74 (s, 2H), 4.01 (s, 2H), 3.61-3.55 (m, 4H), 2.46 (q, J=8.0 Hz, 2H), 1.00 (t, J=8.0 Hz, 3H), 0.91-0.86 (m, 4H), −0.08 (s, 9H), −0.09 (s, 9H).

Synthesis of Intermediate 21: 5-(piperidin-1-yl)pyrazine-2-carboxylic acid

1. Synthesis of Intermediate 20: methyl 5-(piperidin-1-yl)pyrazine-2-carboxylate Methyl 5-chloro-pyrazine-2-carboxylate (1.72 g, 10 mmol) was dissolved in 10 ml of DMF, and then N,N-diisopropylethylamine (4.3 ml, 25.0 mmol) and piperidine hydrochloride were added (1.45 g, 12.0 mmol). The resulting mixture was stirred overnight at room temperature, to which water was added under vigorous stirring. A solid was precipitated and filtered. The filter cake was washed with water, and dried to obtain Intermediate 20 with a yield of 80.0%.

2. Synthesis of Intermediate 21: 5-(piperidin-1-yl)pyrazine-2-carboxylic acid Intermediate 20 (430 mg, 1.95 mmol) was dissolved in 20 ml of tetrahydrofuran and 20 ml of water, and then lithium hydroxide (163 mg, 3.88 mmol) was added. The reaction was carried out at room temperature for 4 hours. The tetrahydrofuran was distilled off under reduced pressure, and the resulting mixture was adjusted with iN HCl to pH 4. A solid was precipitated and filtered. The filter cake was washed with water and dried to obtain Intermediate 21 with a yield of 91.5%.

$^1$H NMR (400 MHz, $CDCl_3$) δ 8.84 (s, 1H), 8.02 (s, 1H), 3.76-3.73 (m, 4H), 1.78-1.65 (m, 6H).

Synthesis of Intermediate 15: N-((2-(6-(2-ethyl-5-fluoro-4-hydroxyphenyl)-1-((2-(trimethylsilyl) ethoxy)methyl)-1H-indazol-3-yl)-1-((2-(trimethylsilyl)ethoxy) methyl)-1H-imidazol-4-yl)methyl)-5-(piperidin-1-yl)pyrazine-2-carboxamide Intermediate 21 (10.4 mg, 0.050 mmol), HATU (22.9 mg, 0.060 mmol), DIPEA (12.9 mg, 0.10 mmol), and 2 ml DMF were added, and it was allowed to react at room temperature for 1 h. The reaction mixture was lowered to 0° C., to which compound 14 (30 mg, 0.049 mmol) in DMF (0.5 ml) was added dropwise. After the dropwise addition was complete, the resulting mixture was warmed to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 127 mg, yield: 67.2%.

$^1$H NMR (400 MHz, $CDCl_3$) δ8.86 (d, J=1.3 Hz, 1H), 8.50 (d, J=8.0 Hz, 1H), 7.95 (d, J=1.4 Hz, 1H), 7.44 (s, 1H), 7.22-7.20 (m, 2H), 7.00-6.94 (m, 2H), 5.89 (s, 2H), 5.75 (s, 2H), 4.71 (d, J=5.7 Hz, 2H), 3.69-3.66 (m, 4H), 3.61-3.55 (m, 4H), 2.51 (q, J=8.0 Hz, 2H), 1.71-1.65 (m, 6H), 1.04 (t, J=8.0 Hz, 3H), 0.91-0.86 (m, 4H), −0.08 (s, 9H), −0.09 (s, 9H).

Synthesis of Compound 16 (MDI-3): N-((2-(6-(2-ethyl-5-fluoro-4-hydroxyphenyl)-1H-indazol-3-yl)-1H-imidazole-4-yl)methyl)-5-(piperidin-1-yl) pyrazine-2-carboxamide Compound 15 (30 mg, 0.037 mmol), 4 ml of MeOH, and 2 ml of concentrated hydrochloric acid were added. After the addition was completed, the resulting mixture was heated to 60° C. and it was allowed to react. After the reaction was completed, the reaction mixture was adjusted with saturated $NaHCO_3$ to pH=7, and extracted with EA. The layers were separated, and resulting organic phase was washed with saturated sodium chloride solution, and dried over anhydrous sodium sulfate. It was concentrated by thin chromatography to afford 14 mg of white solid, yield: 69.2%.

$^1$H NMR (400 MHz, MeOD) δ8.70 (d, J=1.4 Hz, 1H), 8.30 (d, J=8.0 Hz, 1H), 8.21 (d, J=1.4 Hz, 1H), 7.43 (s, 1H), 7.19-7.17 (m, 2H), 6.98-6.90 (m, 2H), 4.67 (s, 2H), 3.78-3.75 (m, 4H), 2.56 (q, J=8.0 Hz, 2H), 1.79-1.67 (m, 6H), 1.08 (t, J=8.0 Hz, 3H).

Example 2: N-((2-(6-(2-ethyl-5-fluoro-4-hydroxyphenyl)-1H-indazol-3-yl)-1H-imidazol-4-yl)methyl) propionamide (MDI-301)

MDI-301

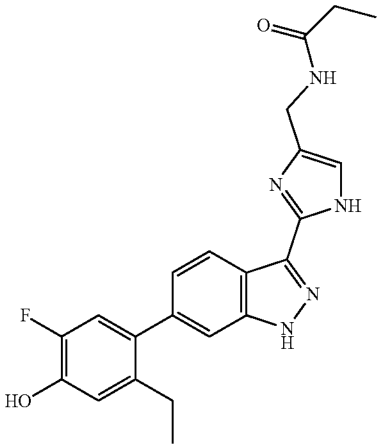

Synthetic Route of MDI-301

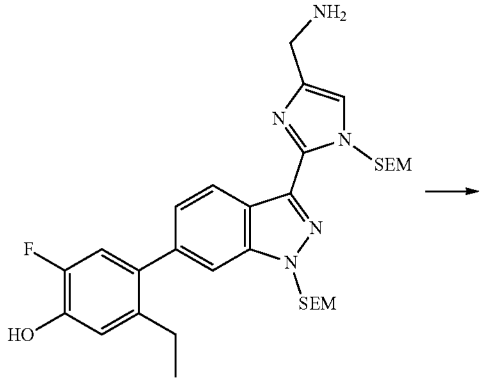

14

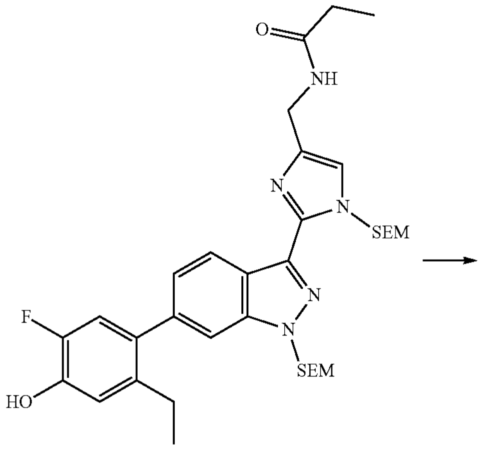

MDI-301-1

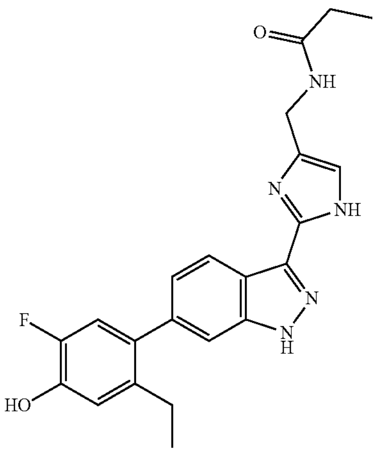

MDI-301

Synthesis Method

Synthesis of Intermediate MDI-301-1: N-((2-(6-(2-ethyl-5-fluoro-4-hydroxyphenyl)-1-((2-(trimethylsilyl)ethoxy)methyl)-1H-indazol-3-yl)-1-((2-(trimethylsilyl)ethoxy)methyl)-1H-imidazol-4-yl)methyl) propionamide Intermediate 14 (30 mg, 0.049 mmol), DIPEA (7.6 mg, 0.059 mmol), and 5 ml DCM were added. The resulting mixture was lowered to 0° C., and propionyl chloride (4.5 mg, 0.049 mmol) was added dropwise. After the dropwise addition was completed, the resulting mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 18 mg, yield: 55.0%.

$^1$H NMR (400 MHz, $CDCl_3$) δ8.41 (d, J=8.0 Hz, 1H), 7.45 (s, 1H), 7.21 (d, J=8.0 Hz, 1H), 7.15 (s, 1H), 6.96 (t, J=10.0 Hz, 2H), 5.88 (s, 2H), 5.75 (s, 2H), 4.50 (d, J=8.0 Hz, 2H), 3.62-3.54 (m, 4H), 2.54-2.48 (m, 2H), 2.30-2.20 (m, 2H), 1.20 (t, J=8.0 Hz, 3H), 1.05 (t, J=8.0 Hz, 3H), 0.92-0.86 (m, 4H), −0.07 (s, 9H), −0.09 (s, 9H).

Synthesis of Compound MDI-301: N-((2-(6-(2-ethyl-5-fluoro-4-hydroxyphenyl)-1H-indazol-3-yl)-1H-imidazol-4-yl)methyl)propionamide Intermediate MDI-301-1 (18 mg, 0.027 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 3 mg of white solid, yield: 27.3%.

$^1$H NMR (400 MHz, MeOD) δ8.27 (d, J=8.0 Hz, 1H), 7.40 (s, 1H), 7.15 (d, J=8.0 Hz, 1H), 7.10 (s, 1H), 6.91 (dd, J=12.0 Hz, J=20.0 Hz, 2H), 4.44 (s, 2H), 2.53 (q, J=8.0 Hz, 2H), 2.87 (q, J=8.0 Hz, 2H), 1.16 (t, J=8.0 Hz, 3H), 1.06 (t, J=8.0 Hz, 3H).

Example 3: N-((2-(6-(2-ethyl-5-fluoro-4-hydroxyphenyl)-1H-indazol-3-yl)-1H-imidazol-4-yl)methyl) cyclopropanecarboxamide (MDI-302)

MDI-302

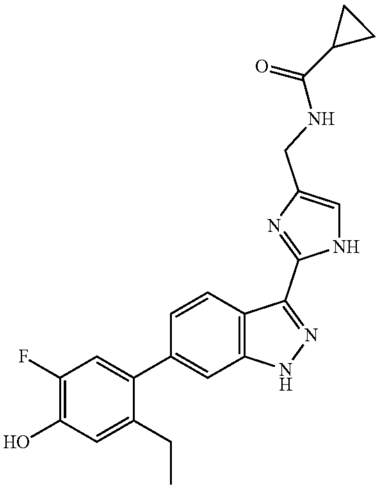

Synthetic Route of MDI-302

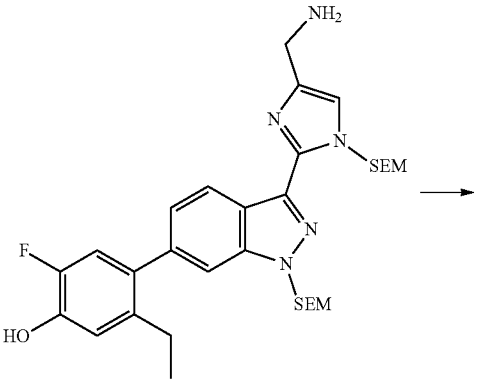

14

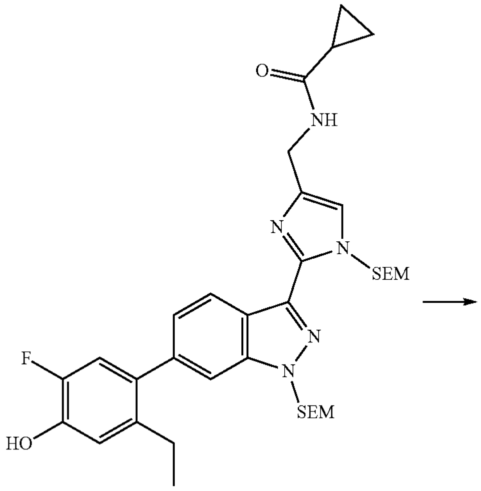

MDI-302-1

-continued

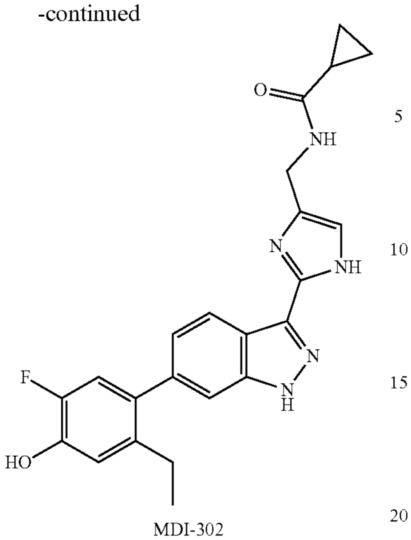

MDI-302

Synthesis Method

Synthesis of Intermediate MDI-302-1: N-((2-(6-(2-ethyl-5-fluoro-4-hydroxyphenyl)-1-((2-(trimethylsilyl)ethoxy)methyl)-1H-indazol-3-yl)-1-((2-(trimethylsilyl) ethoxy)methyl)-1H-imidazol-4-yl)methyl) cyclopropanecarboxamide Intermediate 14 (30 mg, 0.049 mmol), DIPEA (7.6 mg, 0.059 mmol), and 5 ml DCM were added. The resulting mixture was lowered to 0° C., and cyclopropionyl chloride (5.1 mg, 0.049 mmol) was added dropwise. After the dropwise addition was completed, the resulting mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 22 mg, yield: 66.1%.

$^1H$ NMR (400 MHz, $CDCl_3$) δ8.42 (d, J=8.0 Hz, 1H), 7.44 (s, 1H), 7.20 (d, J=8.0 Hz, 1H), 7.15 (s, 1H), 6.9 (t, J=12.0 Hz, 2H), 5.88 (s, 2H), 5.75 (s, 2H), 4.52 (d, J=8.0 Hz, 2H), 3.62-3.54 (m, 4H), 2.53-2.47 (m, 2H), 1.75-1.68 (m, 1H), 1.06 (t, J=8.0 Hz, 3H), 1.02-1.00 (m, 2H), 0.91-0.87 (m, 4H), 0.76-0.72 (m, 2H), −0.07 (s, 9H), −0.09 (s, 9H).

Synthesis of Compound MDI-302: N-((2-(6-(2-ethyl-5-fluoro-4-hydroxyphenyl)-1H-indazol-3-yl)-1H-imidazol-4-yl)methyl)cyclopropanecarboxamide Intermediate MDI-302-1 (20 mg, 0.029 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 8.5 mg of white solid, yield: 69.9%.

$^1H$ NMR (400 MHz, MeOD) δ8.28 (d, J=8.0 Hz 1H), 7.40 (s, 1H), 7.15 (d, J=8.0 Hz, 1H), 7.10 (s, 1H), 6.91 (dd, J=12.0

Hz, J=20.0 Hz, 2H), 4.45 (s, 2H), 2.54 (q, J=8.0 Hz, 2H), 1.67-1.61 (m, 1H), 1.06 (t, J=8.0 Hz, 3H), 0.92-0.85 (m, 2H), 0.79-0.75 (m, 2H).

Example 4: N-((2-(6-(2-ethyl-5-fluoro-4-hydroxyphenyl)-1H-indazol-3-yl)-1H-imidazol-4-yl)methyl) isobutyramide (MDI-303)

MDI-303

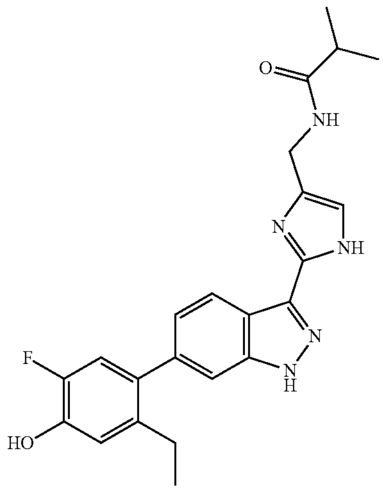

Synthetic Route of MDI-303

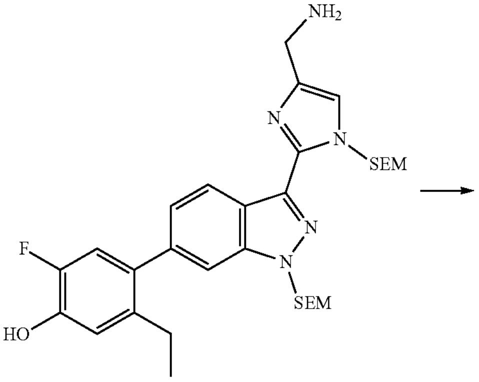

14

-continued

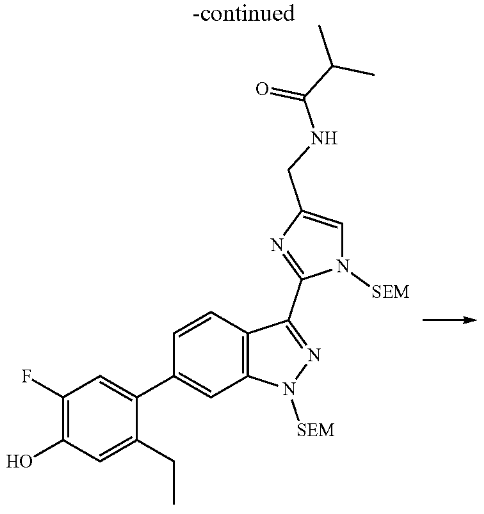

MDI-303-1

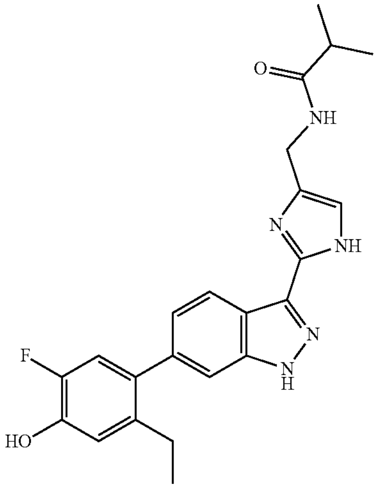

MDI-303

Synthesis Method

Synthesis of Intermediate MDI-303-1: N-((2-(6-(2-ethyl-5-fluoro-4-hydroxyphenyl)-1-((2-(trimethylsilyl)ethoxy)methyl)-1H-indazol-3-yl)-1-((2-(trimethylsilyl)ethoxy)methyl)-1H-imidazol-4-yl)methyl) isobutyramide Intermediate 14 (20 mg, 0.033 mmol), DIPEA (5.1 mg, 0.039 mmol), and 5 ml DCM were added. The resulting mixture was lowered to 0° C., and isobutyryl chloride (3.48 mg, 0.033 mmol) was added dropwise. After the dropwise addition was completed, the resulting mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 14 mg, yield: 62.3%.

$^1$H NMR (400 MHz, $CDCl_3$) δ8.38 (d, J=8.0 Hz, 1H), 7.44 (s, 1H), 7.18 (d, J=8.0 Hz, 1H), 7.15 (s, 1H), 6.96-6.92 (m, 2H), 5.87 (s, 2H), 5.75 (s, 2H), 4.50 (d, J=8.0 Hz, 2H), 3.62-3.54 (m, 4H), 2.52-2.46 (m, 2H), 2.44-2.39 (m, 1H), 1.19 (d, J=4.0 Hz, 6H), 1.03 (t, J=8.0 Hz, 3H), 0.92-0.86 (m, 4.0H), −0.07 (s, 9H), −0.09 (s, 9H).

Synthesis of Compound MDI-303: N-((2-(6-(2-ethyl-5-fluoro-4-hydroxyphenyl)-1H-indazol-3-yl)-1H-imidazol-4-yl)methyl)isobutyramide (MDI-303)

Intermediate MDI-303-1 (14 mg, 0.021 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 4.9 mg of white solid, yield: 56.6%.

$^1$H NMR (400 MHz, MeOD) δ8.29 (d, J=8.0 Hz, 1H), 7.43 (s, 1H), 7.17 (dd, J=4.0 Hz, J=8.0 Hz, 1H), 7.11 (s, 1H), 6.93 (dd, J=12.0 Hz, J=20.0 Hz, 2H), 4.46 (s, 2H), 2.68-2.50 (m, 3H), 1.17 (d, J=4.0 Hz, 6H), 1.08 (t, J=8.0 Hz, 3H).

Example 5: N-((2-(6-(2-ethyl-5-fluoro-4-hydroxyphenyl)-1H-indazol-3-yl)-1H-imidazol-4-yl)methyl) methanesulfonamide (MDI-304)

MDI-304

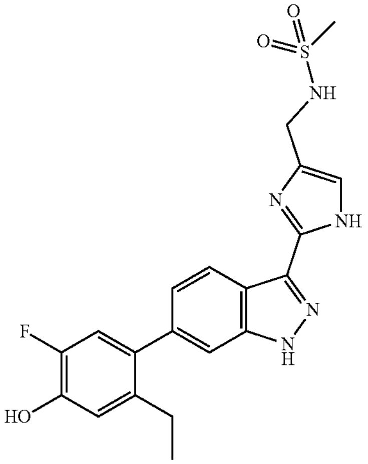

Synthetic Route of MDI-304

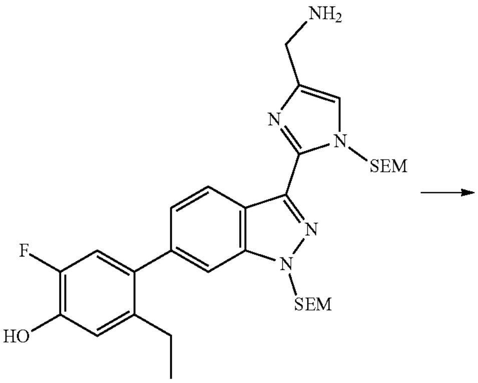

14

-continued

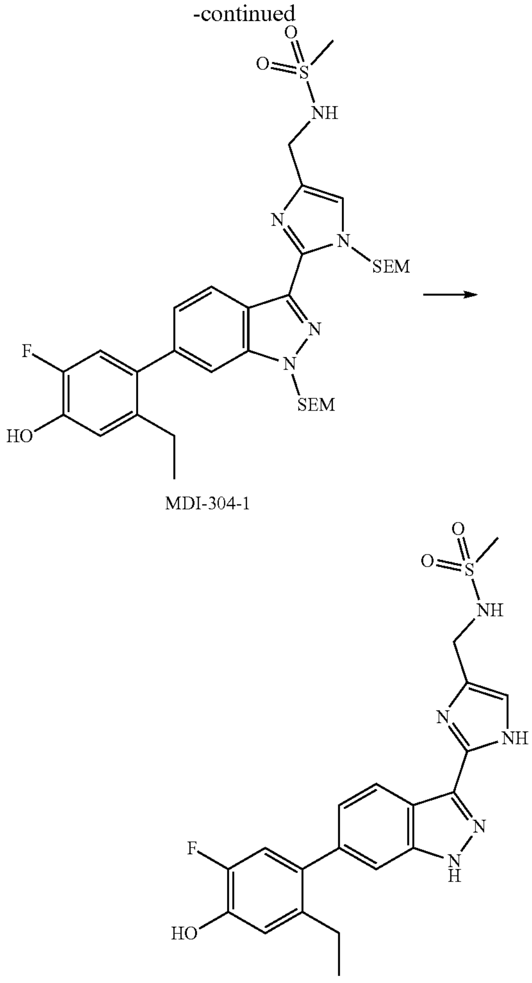

MDI-304-1

MDI-304

Synthesis Method

Synthesis of Intermediate MDI-304-1: N-((2-(6-(2-ethyl-5-fluoro-4-hydroxyphenyl)-1-((2-(trimethylsilyl)ethoxy)methyl)-1H-indazol-3-yl)-1-((2-(trimethylsilyl) ethoxy)methyl)-1H-imidazol-4-yl)methyl) methanesulfonamide Intermediate 14 (30 mg, 0.049 mmol), DIPEA (7.6 mg, 0.059 mmol), and 5 ml DCM were added. The resulting mixture was lowered to 0° C., and methanesulfonyl chloride (5.61 mg, 0.049 mmol) was added dropwise. After the dropwise addition was completed, the resulting mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 12 mg, yield: 35.5%.

$^1$H NMR (400 MHz, $CDCl_3$) δ8.40 (d, J=8.0 Hz, 1H), 7.46 (s, 1H), 7.23 (d, J=8.0 Hz, 1H), 7.19 (s, 1H), 7.00-6.95 (m, 2H), 5.91 (s, 2H), 5.75 (s, 2H), 4.41 (d, J=4.0 Hz, 2H), 2.97 (s, 3H), 2.55-2.49 (m, 2H), 1.06 (t, J=8.0 Hz, 3H), 0.92-0.86 (m, 4H), −0.07 (s, 9H), −0.09 (s, 9H).

Synthesis of Compound MDI-304: N-((2-(6-(2-ethyl-5-fluoro-4-hydroxyphenyl)-1H-indazol-3-yl)-1H-imidazol-4-yl)methyl)methanesulfonamide (MDI-304)

Intermediate MDI-304-1 (12 mg, 0.017 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 3.0 mg of white solid, yield: 40.2%.

$^1$H NMR (400 MHz, MeOD) δ8.21 (d, J=8.0 Hz, 1H), 7.43 (s, 1H), 7.21-7.17 (m, 2H), 6.93 (dd, J=12.0 Hz, J=20.0 Hz, 2H), 4.37 (s, 2H), 2.97 (s, 3H), 2.56 (q, J=8.0 Hz, 2H), 1.08 (t, J=8.0 Hz, 3H).

Example 6: N-((2-(6-(2-ethyl-5-fluoro-4-hydroxyphenyl)-1H-indazol-3-yl)-1H-imidazol-4-yl)methyl)-5-morpholinopyrazine-2-carboxamide (MDI-305)

MDI-305

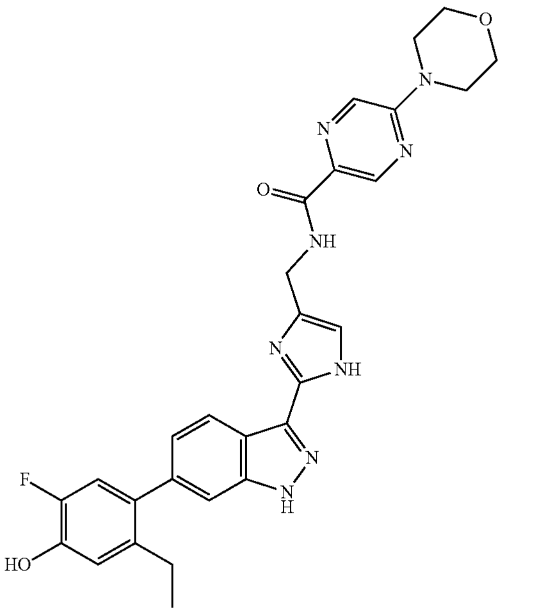

Synthetic Route of MDI-305

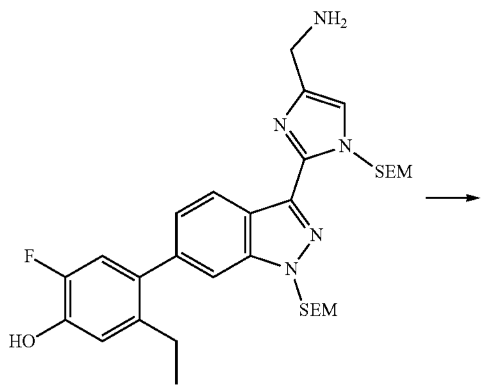

14

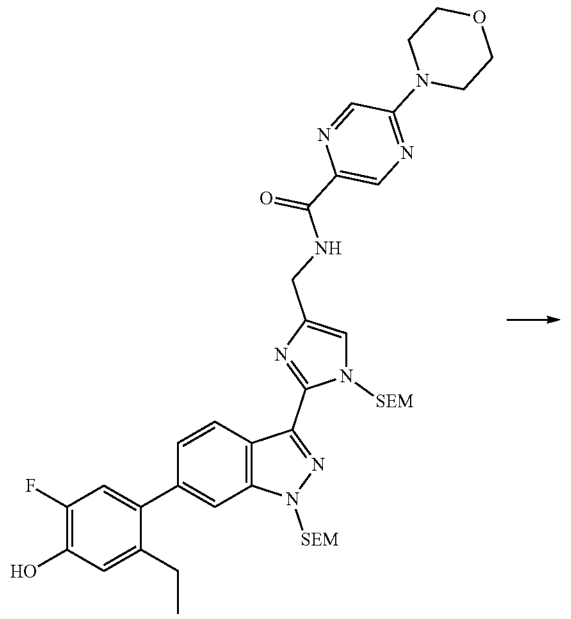

MDI-305-1

-continued

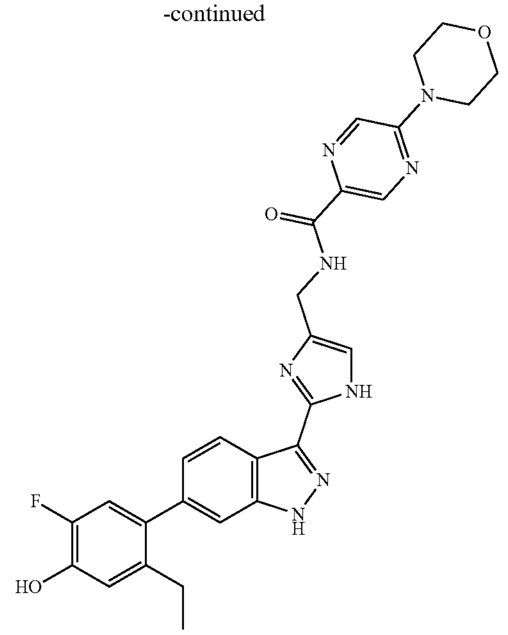

MDI-305

Synthesis Method

Synthesis of Intermediate MDI-305-1: N-((2-(6-(2-ethyl-5-fluoro-4-hydroxyphenyl)-1-((2-(trimethylsilyl)ethoxy)methyl)-1H-indazol-3-yl)-1-((2-(trimethyl silyl)ethoxy)methyl)-1H-imidazol-4-yl)methyl)-5-morpholinopyrazine-2-carboxamide Compound 5-(4-morpholinyl)-2-pyrazinecarboxylic acid (6.84 mg, 0.033 mmol), HATU (13.05 mg, 0.034 mmol), DIPEA (5.06 mg, 0.039 mmol), and 5 ml of DMF were added and it was allowed to react at room temperature for 1 h. The resulting mixture was lowered to 0° C., and compound 14 (20 mg, 0.033 mmol) in DMF (2.0 ml) was added dropwise. After the dropwise addition was completed, the resulting mixture was heated to room temperature and it was allowed to react. After the reaction was completed, it was quenched with water, extracted with EA, and the resulting organic phase was washed with saturated sodium chloride solution, and dried over anhydrous sodium sulfate. It was concentrated and separated by column chromatography to afford a colorless oil 14 mg, yield: 52.9%.

$^1$H NMR (400 MHz, $CDCl_3$) δ8.91 (s, 1H), 8.50 (d, J=8.0 Hz, 1H), 7.95 (s, 1H), 7.44 (s, 1H), 7.22-7.20 (m, 2H), 7.00-6.95 (m, 2H), 5.90 (s, 2H), 5.75 (s, 2H), 4.71 (d, J=8.0 Hz, 2H), 3.83-3.81 (m, 4H), 3.68-3.66 (m, 4H), 3.62-3.55 (m, 4H), 2.51 (q, J=8.0 Hz, 2H), 1.05 (t, J=8.0 Hz, 3H), 0.91-0.86 (m, 4H), −0.07 (s, 9H), −0.09 (s, 9H).

Synthesis of Compound MDI-305: N-((2-(6-(2-ethyl-5-fluoro-4-hydroxyphenyl)-1H-indazol-3-yl)-1H-imidazol-4-yl) Methyl)-5-morpholinopyrazine-2-carboxamide Intermediate MDI-305-1 (14 mg, 0.017 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 3.9 mg of white solid, yield: 41.2%.

$^1$H NMR (400 MHz, MeOD) δ8.73 (s, 1H), 8.28 (d, J=8.0 Hz, 1H), 8.20 (s, 1H), 7.40 (s, 1H), 7.17-7.14 (m, 2H), 6.95-6.87 (m, 2H), 4.65 (s, 2H), 3.80-3.77 (m, 4H), 3.73-3.70 (m, 4H), 2.53 (q, J=8.0 Hz, 2H), 1.06 (t, J=8.0 Hz, 3H).

Example 7: (S)-1-((2-(6-(2-ethyl-5-fluoro-4-hydroxyphenyl)-1H-indazol-3-yl)-1H-imidazol-4-yl)methyl)pyrrolidin-3-ol (MDI-306)

MDI-306

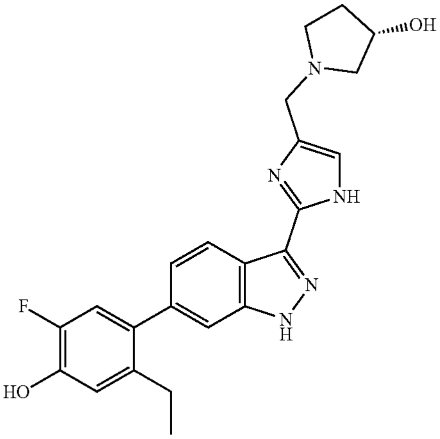

Synthetic Route of MDI-306

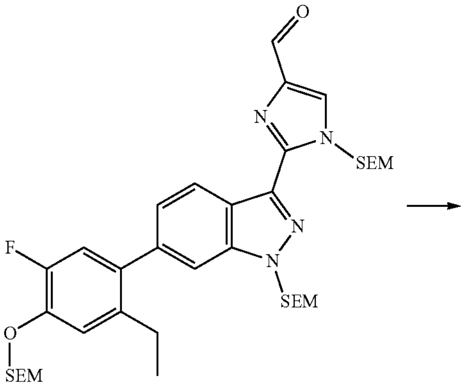

12

-continued

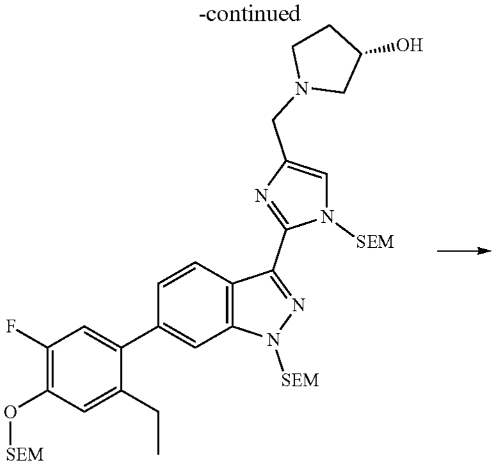

MDI-306-1

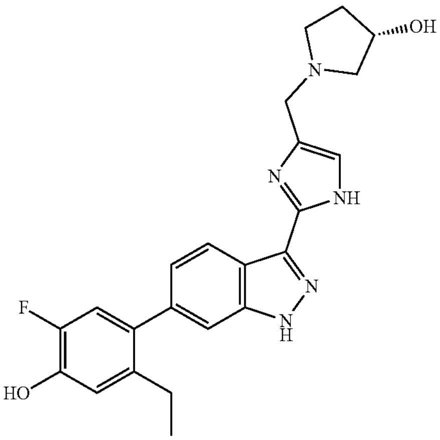

MDI-306

Synthesis Method

Synthesis of Intermediate MDI-306-1: (S)-1-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)pyrrolidin-3-ol (S)-1-N-tert-butoxycarbonyl-3-hydroxypyrrolidine (9.1 mg, 0.049 mmol), 2 ml of DCM, and 2 ml of trifluoroacetic acid were added. After the addition was complete, the resulting mixture was stirred at room temperature for 30 min. After the reaction was complete, the reaction mixture was concentrated, and 5 ml of 1,2-dichloroethane and intermediate 12 (30 mg, 0.041 mmol) were added. After the addition was complete, the resulting mixture was stirred at room temperature for 30 min. Then sodium triacetylborohydride (17.08 mg, 0.081 mmol) was added and it was allowed to react at room temperature. After the reaction was completed, it was quenched with water, extracted with DCM, and the resulting organic phase was washed with saturated sodium chloride solution, and dried over anhydrous sodium sulfate. It was concentrated and separated by thin chromatography to afford product 20 mg, yield: 60.8%.

$^1$H NMR (400 MHz, $CDCl_3$) δ 8.44 (d, J=8.0 Hz, 1H), 7.45 (s, 1H), 7.24-7.21 (m, 2H), 7.15 (d, J=8.0 Hz, 1H), 7.0

(d, J=12.0 Hz, 1H), 5.91 (s, 2H), 5.75 (s, 2H), 5.32 (s, 2H), 4.44-4.39 (m, 1H), 3.92-3.84 (m, 4H), 3.64-3.55 (m, 4H), 3.29-3.19 (m, 1H), 3.12-3.07 (m, 1H), 2.96-2.88 (m, 1H), 2.78-2.66 (m, 1H), 2.57-2.51 (m, 2H), 2.24-2.20 (m, 1H), 1.91-1.87 (m, 1H), 1.05 (t, J=8.0 Hz, 3H), 1.03-0.98 (m, 2H), 0.92-0.86 (m, 4H), 0.03 (s, 9H), −0.07 (s, 9H), −0.09 (s, 9H).

Synthesis of Compound MDI-306: (S)-1-((2-(6-(2-ethyl-5-fluoro-4-hydroxyphenyl)-1H-indazol-3-yl)-1H-imidazole-4-yl)methyl)pyrrolidin-3-ol Intermediate MDI-306-1 (20 mg, 0.025 mmol), 4 ml MeOH, and 2 ml concentrated hydrochloric acid were added. After the addition was completed, the reaction mixture was raised to 50° C. and it was allowed to react for 6 hours. The reaction mixture was lowered to room temperature, and the reaction solvent was distilled off under reduced pressure. And then 4 ml of methanol, and 0.5 ml of aqueous ammonia were added. After concentration, the residue was separated by thin chromatography to obtain 6.2 mg of white solid, yield: 59.7%.

$^1$H NMR (400 MHz, MeOD) δ8.31 (d, J=8.0 Hz, 1H), 7.43 (s, 1H), 7.18-7.16 (m, 2H), 6.97-6.89 (m, 2H), 4.44-4.39 (m, 1H), 3.90-3.82 (m, 2H), 3.01-2.95 (m, 2H), 2.77-2.74 (m, 2H), 2.58-2.53 (m, 2H), 2.25-2.16 (m, 1H), 1.84-1.78 (m, 1H), 1.08 (t, J=8.0 Hz, 3H).

Example 9:1-((2-(6-(2-ethyl-5-fluoro-4-hydroxyphenyl)-1H-indazol-3-yl)-1H-imidazol-4-yl)methyl)piperidin-4-ol (Ex-9)

Ex-9

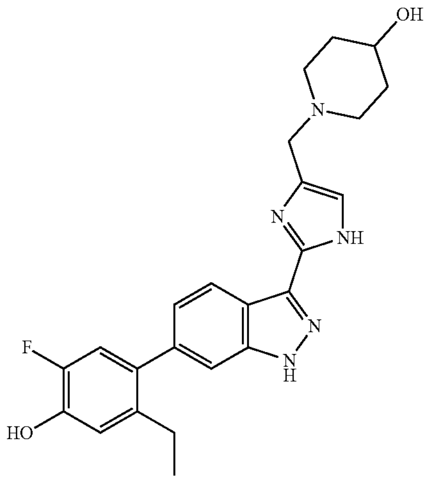

Synthetic Route of Ex-9

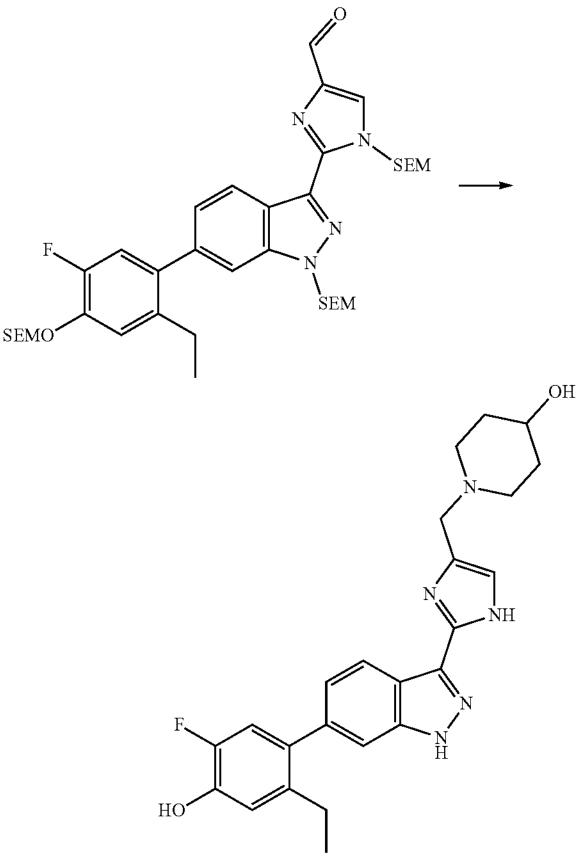

Ex-9

Synthesis Method

Synthesis of Compound Ex-9: 1-((2-(6-(2-ethyl-5-fluoro-4-hydroxyphenyl)-1H-indazol-3-yl)-1H-imidazol-4-yl)methyl)piperidin-4-ol 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (30 mg, 0.04 mmol) was dissolved in DCM, to which piperidin-4-ol (4.9 mg, 0.05 mmol) was added. The resulting mixture was reacted at room temperature for 0.5 hours. To the reaction mixture was added sodium triacetylborohydride (17.2 mg, 0.08 mmol). It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified on silica gel plate. The obtained product was dissolved in 2 ml of methanol and 1 ml of concentrated hydrochloric acid. It was allowed to react at 50° C. for 6 hours and concentrated. The resulting mixture was dissolved in 3 ml of methanol, to which 0.5 ml of aqueous ammonia was added, and then it was concentrated, and purified by preparative plate to obtain 6 mg of the final product with a yield of 32.8%.

$^1$H NMR (400 MHz, MeOD) δ 8.33 (d, J=12.0 Hz, 1H), 7.44 (s, 1H), 7.32 (s, 1H), 7.18 (d, J=8.0 Hz, 1H), 6.90-6.97 (m, 2H), 4.01-4.08 (m, 2H), 3.81-3.86 (m, 1H), 3.23-3.30 (m, 2H), 2.78-2.92 (m, 2H), 2.53-2.59 (m, 2H), 1.98-2.04 (m, 2H), 1.72-1.80 (m, 2H), 1.08 (t, J=8.0 Hz, 3H).

Example 10: N-((2-(6-(2-ethyl-5-fluoro-4-hydroxyphenyl)-1H-indazol-3-yl)-1H-imidazol-4-yl)methyl)-N-methylcyclopropanecarboxamide (Ex-10)

Ex-10

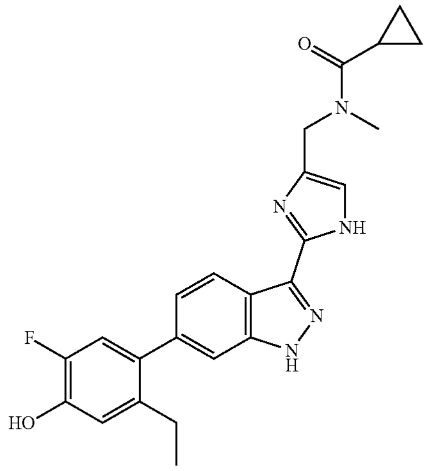

Synthetic Route of Ex-10

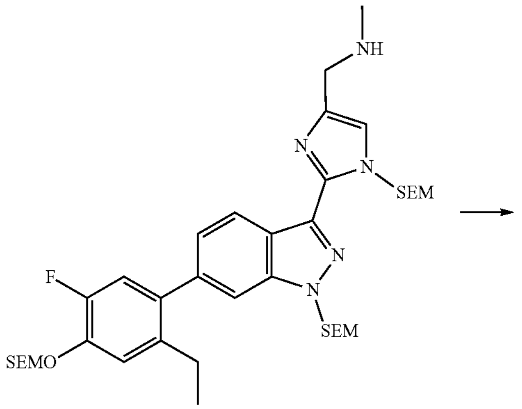

-continued

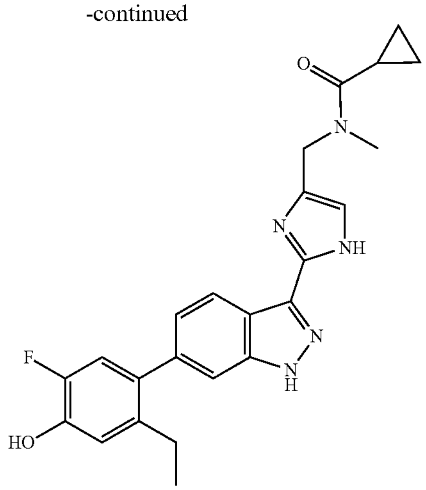

Ex-10

Synthesis Method

Synthesis of Compound Ex-10: N-((2-(6-(2-ethyl-5-fluoro-4-hydroxy phenyl)-1H-indazol-3-yl)-1H-imidazol-4-yl)methyl)-N-methylcyclopropane carboxamide 1-(2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-yl)-N-methylmethylamine (20 mg, 0.03 mmol) was dissolved in DCM, to which triethylamine (5.3 mg, 0.05 mmol) was added. The resulting mixture was cooled to zero, and cyclopropanecarbonyl chloride (3.3 mg, 0.03 mmol) was added dropwise. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified on silica gel plate. The obtained product was dissolved in 2 ml of methanol and 1 ml of concentrated hydrochloric acid. It was allowed to react at 50° C. for 6 hours and concentrated. The resulting mixture was dissolved in 3 ml of methanol, to which 0.5 ml of aqueous ammonia was added, and then it was concentrated, and purified by preparative plate to obtain 4 mg of the final product with a yield of 34.9%.

$^1$H NMR (400 MHz, DMSO) δ 13.29 (s, 1H), 12.62 (s, 1H), 9.86 (s, 1H), 8.34 (d, J=8.0 Hz, 1H), 7.40 (s, 1H), 7.13 (d, J=8.0 Hz, 2H), 7.04 (d, J=12.0 Hz, 1H), 6.92 (d, J=8.0 Hz, 1H), 4.51-4.67 (m, 2H), 3.17-3.23 (s, 3H), 2.46-2.48 (m, 2H), 1.99-2.01 (m, 1H), 1.02 (t, J=8.0 Hz, 3H), 0.76-0.87 (m, 4H). LC-MS m/z (ESI) [M+H]+ calculated for $C_{24}H_{25}FN_5O_2$: 434.2; Measured: 434.2.

Example 11: 1-((2-(6-(2-ethyl-5-fluoro-4-hydroxyphenyl)-1H-indazol-3-yl)-1H-imidazol-4-yl)methyl) piperidine-4-nitrile (Ex-11)

Ex-11

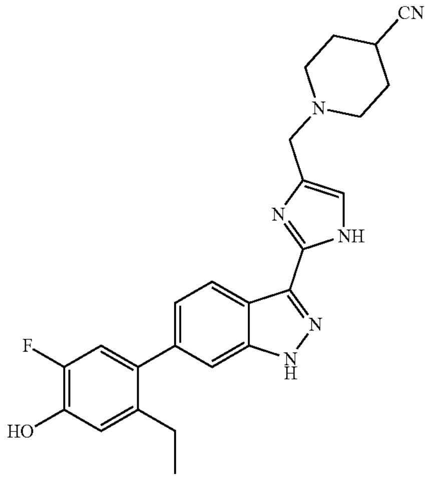

Synthetic Route of Ex-11

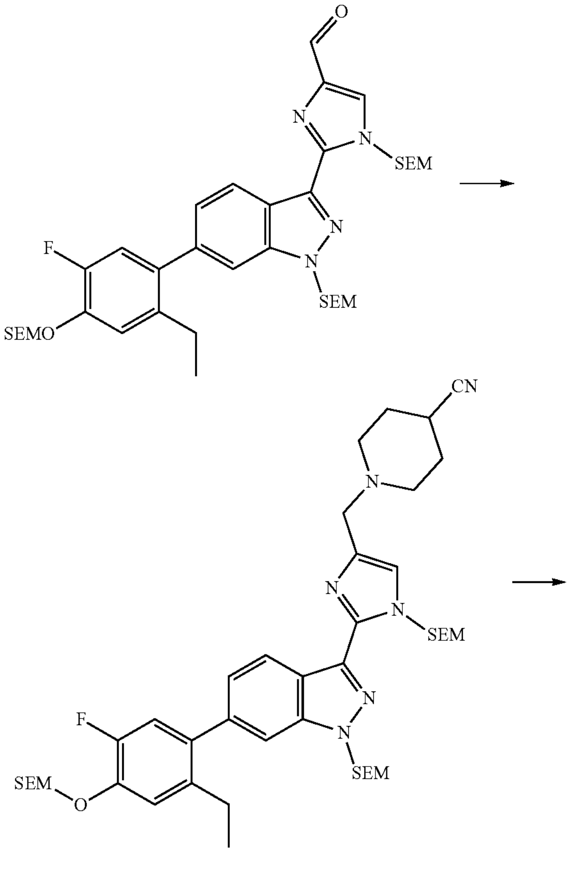

11-1

-continued

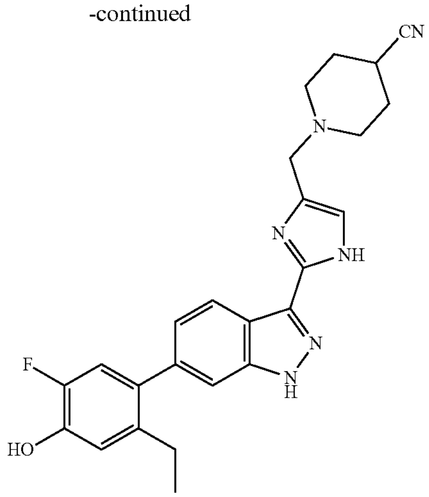

Ex-11

Synthesis Method

Synthesis of Intermediate 11-1: 1-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)piperidine-4-carbonitrile 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (25.0 mg, 0.03 mmol) was dissolved in 5 ml of anhydrous dichloromethane, to which 4-cyanopiperidine (5.6 mg, 0.05 mmol) was added, the resulting mixture was allowed to react at room temperature for 30 minutes and to the mixture was added sodium triacetylborohydride (10.7 mg, 0.05 mmol). It was allowed to react at room temperature for 1 hour, to which water was added, and then the reaction solution was extracted twice with dichloromethane. The resulting organic phases was combined, washed with saturated brine, and dried over anhydrous sodium sulfate. It was concentrated and purified to obtain 24.2 mg of Intermediate 11-1 with a yield of 86.0%.

Synthesis of Compound Ex-11: 1-((2-(6-(2-ethyl-5-fluoro-4-hydroxyphenyl)-1H-indazol-3-yl)-1H-imidazol-4-yl) methyl)piperidine-4-carbonitrile The intermediate 11-1 (24.2 mg, 0.03 mmol) was dissolved in 2 ml of methanol, to which 1 ml of concentrated hydrochloric acid was added. It was allowed to react at 50° C. for 6 hours and concentrated. The resulting mixture was dissolved in 2 ml of methanol, to which 0.5 ml of aqueous ammonia was added, and then it was concentrated, and purified by preparative plate to obtain 3.4 mg of the final product with a yield of 26.4%.

$^1$H NMR (400 MHz, MeOD) δ 8.30 (dd, J=4.0 Hz, J=8.0 Hz, 1H), 7.43 (d, J=4.0 Hz, 1H), 7.19-7.16 (m, 2H), 6.95 (dd, J=8.0 Hz, J=20.0 Hz, 2H), 3.75 (s, 2H), 2.89-2.86 (m, 3H), 2.59-2.53 (m, 4H), 2.06-2.03 (m, 2H), 1.97-1.86 (m, 2H), 1.08 (t, J=8.0 Hz, 3H).

Example 12: 1-((2-(6-(2-ethyl-5-fluoro-4-hydroxyphenyl)-1H-indazol-3-yl)-1H-imidazol-4-yl)methyl) pyrrolidine-3-carbonitrile (Ex-12)

Ex-12

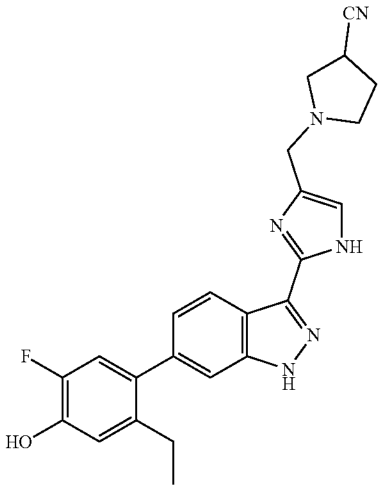

Synthetic Route of Ex-12

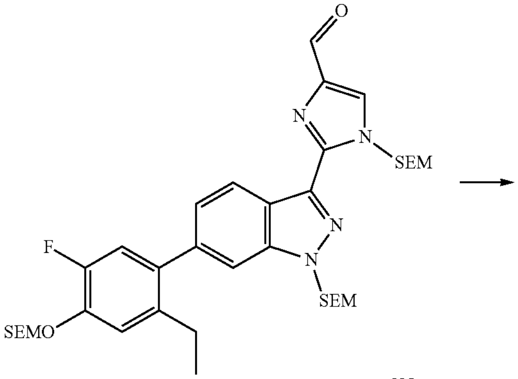

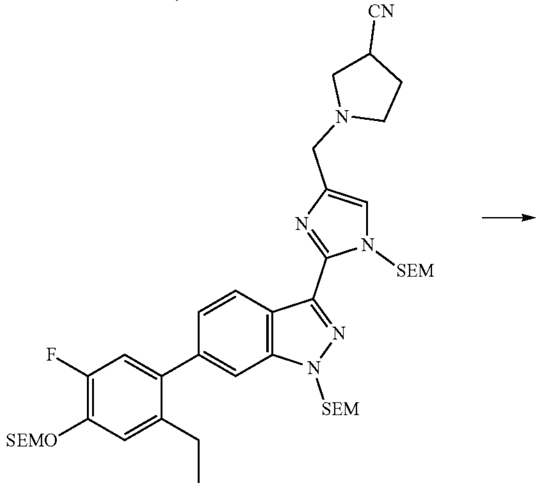

12-1

-continued

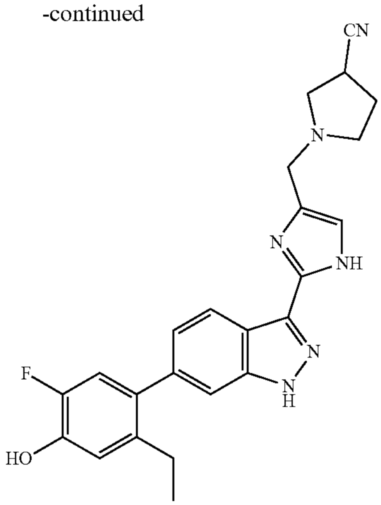

Ex-12

Synthesis Method

Synthesis of Intermediate 12-1: 1-((2-(6-(2-ethyl-5-fluoro-4-((2-(trimethyl silyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)pyrrolidine-3-carbonitrile The intermediate 2-(6-(2-ethyl-5-fluoro-4-((2-(trimethylsilyl) ethoxy) methoxy) phenyl)-1-((2-(trimethylsilyl) ethoxy)methyl)-1H-indol-3-yl)-1-(((2-(trimethylsilyl) ethoxy)methyl)-1H-imidazole-4-formaldehyde (30.0 mg, 0.04 mmol) was dissolved in 5 ml of dichloromethane, to which pyrrolidine-3-carbonitrile (5.1 mg, 0.05 mmol) was added. The resulting mixture was stirred at room temperature for 0.5 hours, and then sodium triacetyl borohydride (17.0 mg, 0.08 mmol) was added. It was allowed to further react at room temperature for 2 h. The reaction mixture was quenched with a small amount of water and the solvent was evacuated with a vacuum pump and then the resulting residue was purified on a silica gel plate to obtain 21 mg of intermediate 12-1 with a yield of 56.9%.

Synthesis of Compound Ex-12: 1-((2-(6-(2-ethyl-5-fluoro-4-hydroxyphenyl)-1H-indazol-3-yl)-1H-imidazol-4-yl) methyl)pyrrolidine-3-carbonitrile The intermediate 12-1 (20.0 mg, 0.02 mmol) was dissolved in 2 ml of methanol, to which 1 ml of concentrated hydrochloric acid was added. It was allowed to react at 50° C. for 6 hours and concentrated. The resulting residue was dissolved in 2 ml of methanol, to which 0.5 ml of aqueous ammonia was added, and then it was concentrated, and purified by preparative plate to obtain 3 mg of the final product with a yield of 28.6%.

$^1$H NMR (400 MHz, DMSO) δ 13.27 (s, 1H), 12.58 (s, 1H), 9.87 (s, 1H), 8.34 (d, J=8.4 Hz, 1H), 7.39 (s, 1H), 7.13 (d, J=7.5 Hz, 2H), 7.04 (d, J=11.9 Hz, 1H), 6.92 (d, J=9.1 Hz, 1H), 3.61 (s, 2H), 3.17-3.18 (m, 1H), 2.98-3.11 (m, 1H), 2.75-2.82 (m, 1H), 2.62-2.72 (m, 1H), 2.55-2.61 (m, 1H), 2.43-2.49 (m, 2H), 1.96-2.04 (m, 2H), 1.02 (t, J=7.5 Hz, 3H).

Example 13: 5-ethyl-2-fluoro-4-(3-(4-(morpholinomethyl)-1H-imidazol-2-yl)-1H-indazol-6-yl)phenol (Ex-13)

Ex-13

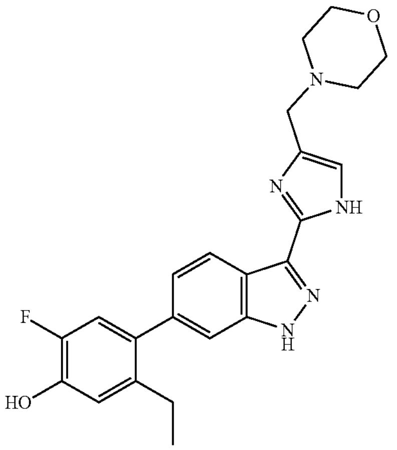

Synthetic Route of Ex-13

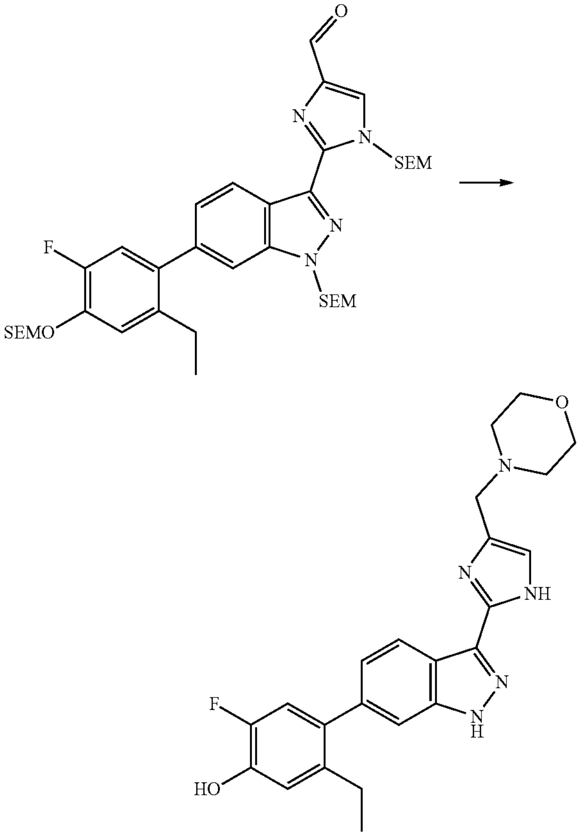

Ex-13

Synthesis Method

Synthesis of Compound Ex-13: 5-ethyl-2-fluoro-4-(3-(4-(morpholinomethyl)-1H-imidazol-2-yl)-1H-indazol-6-yl)phenol 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (30.0 mg, 0.04 mmol) was dissolved in DCM, to which morpholine (4.4 mg, 0.05 mmol) was added. It was allowed to react at room temperature for 0.5 hours. To the reaction mixture was added sodium triacetylborohydride (17.2 mg, 0.08 mmol). It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified. The obtained product was dissolved in 2 ml of methanol and 1 ml of concentrated hydrochloric acid. It was allowed to react at 50° C. for 6 hours and concentrated. The resulting residue was dissolved in 3 ml of methanol, to which 0.5 ml of aqueous ammonia was added, and then it was concentrated and purified by preparative plate to obtain 8 mg of the final product with a yield of 46.9%.

$^1$H NMR (400 MHz, DMSO) δ 13.23 (s, 1H), 12.55 (d, J=20.0 Hz, 1H), 9.85 (s, 1H), 8.34 (d, J=8.0 Hz, 1H), 7.39 (s, 1H), 7.10-7.14 (m, 1H), 6.95-7.05 (m, 2H), 6.92 (t, J=8.0 Hz, 1H), 3.59 (t, J=4 Hz, 4H), 3.49-3.55 (m, 2H), 2.49-2.50 (m, 2H), 2.42-2.48 (m, 4H), 1.02 (t, J=8 Hz, 3H).

Example 14: 5-ethyl-2-fluoro-4-(3-(4-((pyridin-3-ylamino)methyl)-1H-imidazol-2-yl)-1H-indazol-6-yl)phenol (Ex-14)

Ex-14

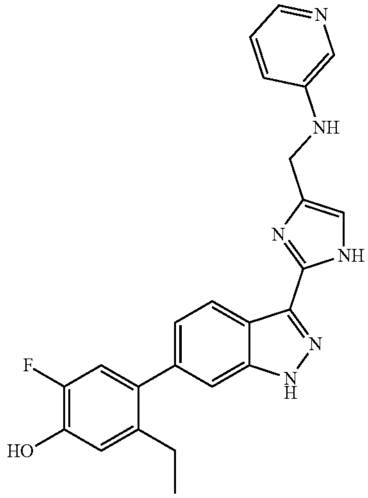

Synthetic Route of Ex-14

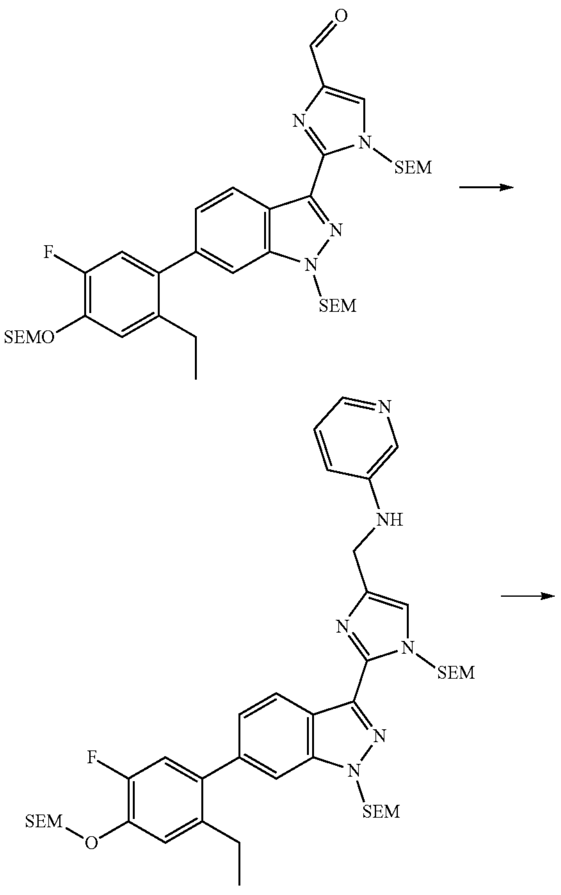

14-1

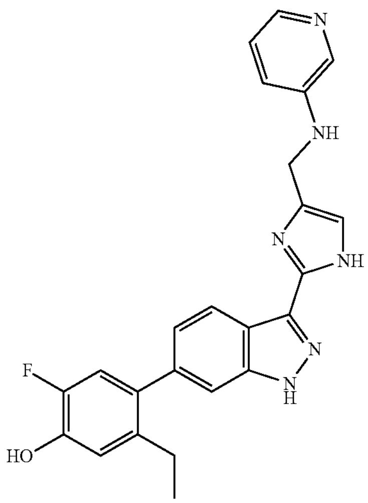

Ex-14

Synthesis Method

Synthesis of Intermediate 14-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)pyridin-3-amine 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (30.0 mg, 0.04 mmol) was dissolved in 5 ml of toluene, to which 3-aminopyridine (5.6 mg, 0.06 mmol) and 1 drop of glacial acetic acid were added. The resulting mixture was heated to 90° C. and it was allowed to react for 24 hours. The reaction mixture was cooled to room temperature, and sodium triacetylborohydride (12.7 mg, 0.06 mmol) was added. It was allowed to react at room temperature for 1 hour, to which water was added, and then the reaction solution was extracted twice with ethyl acetate. The resulting organic phases was combined, washed with saturated brine, and dried over anhydrous sodium sulfate. It was concentrated and purified to obtain 23 mg of intermediate 14-1 with a yield of 69.3%.

Synthesis of Compound Ex-14: 5-ethyl-2-fluoro-4-(3-(4-((pyridin-3-ylamino)methyl)-1H-imidazol-2-yl)-1H-indazole-6-yl)phenol The intermediate 14-1 (23.0 mg, 0.03 mmol) was dissolved in 2 ml methanol, to which 1 ml concentrated hydrochloric acid was added. It was allowed to react at 50° C. for 6 hours and concentrated. The resulting residue was dissolved in 2 ml methanol, to which 0.5 ml of aqueous ammonia was added. It was concentrated and purified by a preparative silica gel plate, to obtain 7.1 mg of final product with a yield of 59.0%.

$^{1}$H NMR (400 MHz, MeOD) δ 8.29 (dd, J=4.0 Hz, J=12.0 Hz, 1H), 8.05 (d, J=4.0 Hz, 1H), 7.80 (d, J=4.0 Hz, 1H), 7.42 (d, J=4.0 Hz, 1H), 7.20-7.14 (m, 4H), 6.95 (dd, J=12.0 Hz, J=20.0 Hz, 2H), 4.44 (s, 2H), 2.59-2.53 (m, 2H), 1.08 (t, J=8.0 Hz, 3H).

Example 15: 5-ethyl-2-fluoro-4-(3-(4-(((1-methyl-1H-pyrazol-4-yl)amino)methyl)-1H-imidazol-2-yl)-1H-indazol-6-yl)phenol (Ex-15)

Ex-15

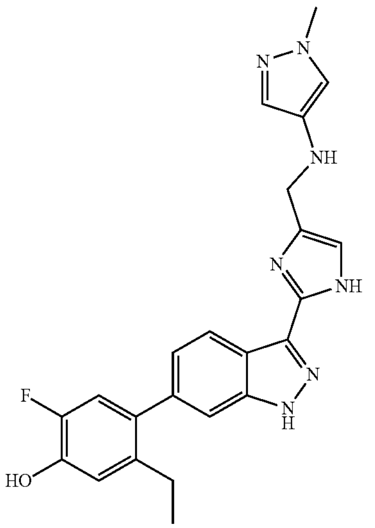

Synthetic Route of Ex-15

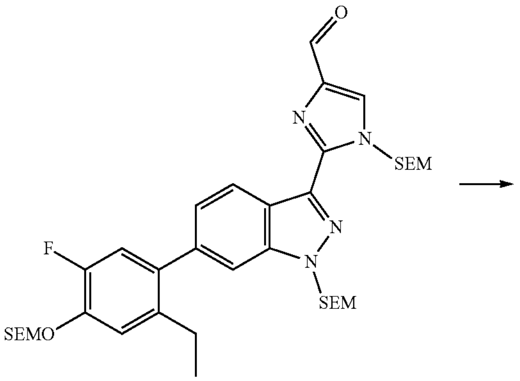

-continued

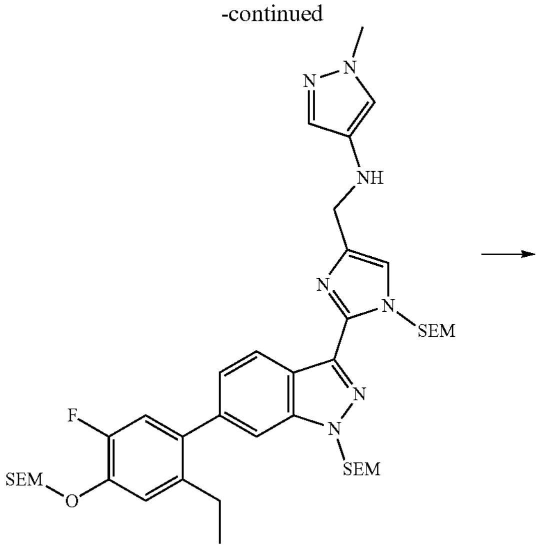

15-1

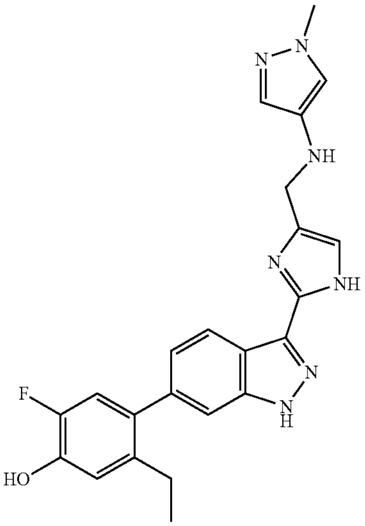

Ex-15

Synthesis Method

Synthesis of Intermediate 15-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-1-methyl-1H-pyrazol-4-amine 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (30.0 mg, 0.04 mmol) was dissolved in 5 ml of toluene, to which 1-methyl-1H-pyrazol-4-amine (5.9 mg, 0.06 mmol) and 1 drop of glacial acetic acid were added. The resulting mixture was heated to 90° C. and it was allowed to react for 24 hours. The reaction mixture was cooled to room temperature, and sodium triacetylborohydride (12.7 mg, 0.06 mmol) was added. It was allowed to react at room temperature for 1 hour, to which water was added, and then the reaction solution was extracted twice with ethyl acetate. The resulting organic phases was combined, washed with saturated brine, and dried over anhydrous sodium sulfate. It was concentrated and purified to obtain 22.9 mg of intermediate 15-1 with a yield of 68.8%.

Synthesis of Compound Ex-15: 5-ethyl-2-fluoro-4-(3-(4-(((1-methyl-1H-pyrazol-4-yl)amino)methyl)-1H-imidazole-2-yl)-1H-indazol-6-yl)phenol The intermediate 15-1 (22.9 mg, 0.03 mmol) was dissolved in 2 ml methanol, to which 1 ml concentrated hydrochloric acid was added. It was allowed to react at 50° C. for 6 hours and concentrated. The resulting residue was dissolved in 2 ml methanol, to which 0.5 ml of aqueous ammonia was added. It was concentrated and purified by a preparative silica gel plate, to obtain 5.4 mg of final product with a yield of 45.0%.

$^1$H NMR (400 MHz, MeOD) δ 8.29 (dd, J=4.0 Hz, J=12.0 Hz, 1H), 7.42 (d, J=4.0 Hz, 1H), 7.25 (d, J=4.0 Hz, 1H), 7.21 (d, J=4.0 Hz, 1H), 7.17 (dd, J=4.0 Hz, J=8.0 Hz, 1H), 7.13 (s, 1H), 6.94 (dd, J=12.0 Hz, J=20.0 Hz, 2H), 4.21 (s, 2H), 3.80 (s, 3H), 2.59-2.53 (m, 2H), 1.08 (t, J=8.0 Hz, 3H).

Example 16: 3-((2-(6-(2-ethyl-5-fluoro-4-hydroxyphenyl)-1H-indazol-3-yl)-1H-imidazol-4-yl)methyl)-1-(2-hydroxyethyl)-1-methylurea (Ex-16)

Ex-15

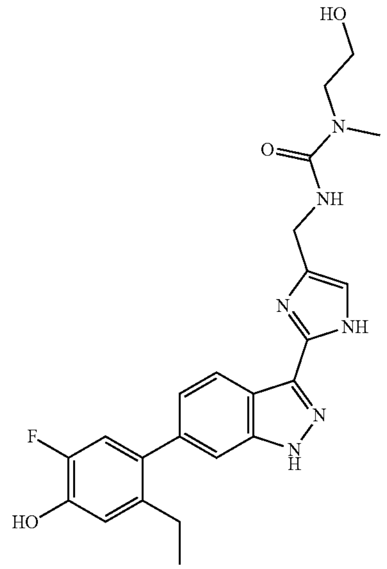

Synthetic Route of Ex-16

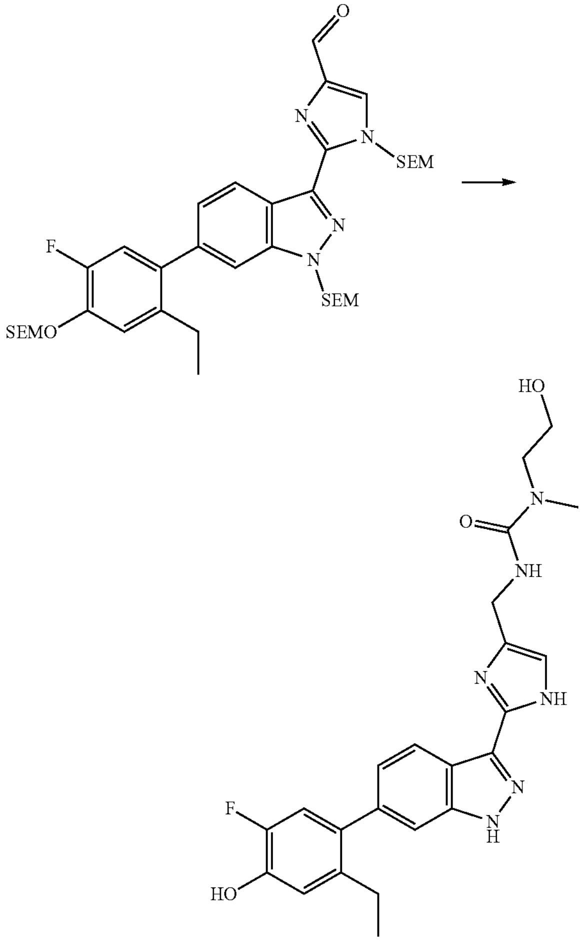

Ex-16

Synthesis of Compound Ex-16: 3-((2-(6-(2-ethyl-5-fluoro-4-hydroxyphenyl)-1H-indazol-3-yl)-1H-imidazol-4-yl)methyl)-1-(2-hydroxyethyl)-1-methylurea Triphosgene (11.1 mg, 0.04 mmol) was dissolved in DCM, and cooled to zero. To the resulting solution was added (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (25.0 mg, 0.03 mmol) in DCM. It was allowed to react for 5 minutes. Then triethylamine (10.2 mg, 0.10 mmol was dropwise added slowly. It was allowed to react at 0° C. for 0.5 hours. Then 2-(methylamino)ethane-1-ol (3.8 mg, 0.05 mmol) was added. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified. The obtained product was dissolved in 2 ml of methanol and 1 ml of concentrated hydrochloric acid. It was allowed to react at 50° C. for 6 hours and concentrated. The resulting residue was dissolved in 3 ml of methanol, to which 0.5 ml of aqueous ammonia was added, and then it was concentrated and purified by preparative silica gel plate to obtain 7 mg of the final product with a yield of 45.9%.

$^1$H NMR (400 MHz, MeOD) δ 8.28 (d, J=8.0 Hz, 1H), 7.42 (s, 1H), 7.17 (d, J=8.0 Hz, 1H), 7.10 (s, 1H), 6.89-6.97 (m, 2H), 4.44 (s, 2H), 3.71 (t, J=6.0 Hz, 2H), 3.45 (t, J=6.0 Hz, 2H), 3.01 (s, 3H), 2.53-2.59 (m, 2H), 1.08 (t, J=8.0 Hz, 3H).

Example 17: 4-(3-(4-(((cyclopropylmethyl)amino) methyl)-1H-imidazol-2-yl)-1H-indazol-6-yl)-5-ethyl-2-fluoro phenol (Ex-17)

Ex-17

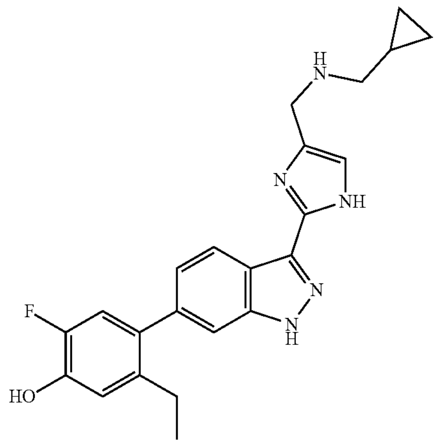

Synthetic Route of Ex-17

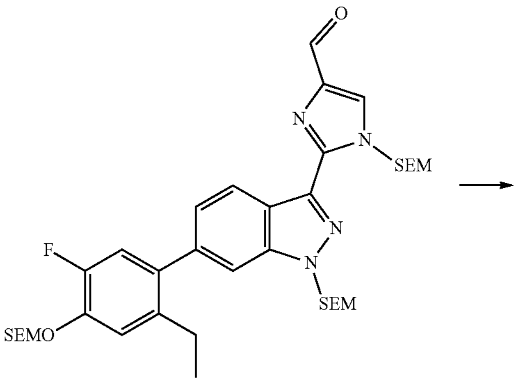

-continued

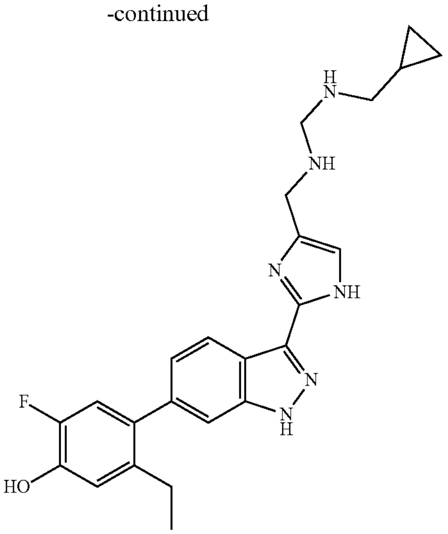

Ex-17

Synthesis Method

Synthesis of Compound Ex-17: 4-(3-(4-(((cyclopropylmethyl) amino)methyl)-1H-imidazol-2-yl)-1H-indazol-6-yl)-5-ethyl-2-fluorophenol 2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (30.0 mg, 0.04 mmol) and cyclopropylmethylamine (4.2 mg, 0.06 mmol) were dissolved in DCM. It was allowed to react at room temperature for 0.5 h. To the reaction solution was added sodium triacetylborohydride (16.4 mg, 0.06 mmol). It was allowed to react at room temperature for 1.5 hours, to which water was added, and then the reaction solution was extracted twice with DCM. The resulting organic phases was combined, washed with saturated brine, and dried over anhydrous sodium sulfate. It was concentrated and purified on silica gel plate. The obtained product was dissolved in 2 ml of methanol and 1 ml of concentrated hydrochloric acid. It was allowed to react at 50° C. for 6 hours and concentrated. The resulting residue was dissolved in 3 ml of methanol, to which 0.5 ml of aqueous ammonia was added, and then it was concentrated and purified by preparative silica gel plate to obtain 6.4 mg of the final product with a yield of 39.0%.

$^1$H NMR (400 MHz, MeOD) δ 8.35 (d, J=8 Hz, 1H), 7.45 (s, 1H), 7.33 (s, 1H), 7.22-7.17 (m, 1H), 6.99-6.88 (m, 2H), 4.19 (s, 2H), 2.91 (d, J=8 Hz, 2H), 2.62-2.51 (m, 2H), 1.18-1.11 (m, 1H), 1.08 (t, J=8 Hz, 3H), 0.74-0.67 (m, 2H), 0.42-0.35 (m, 2H).

Example 18: N-((2-(6-(2-ethyl-5-fluoro-4-hydroxyphenyl)-1H-indazol-3-yl)-1H-imidazol-4-yl)methyl) cyclopropanesulfonamide (Ex-18)

Ex-18

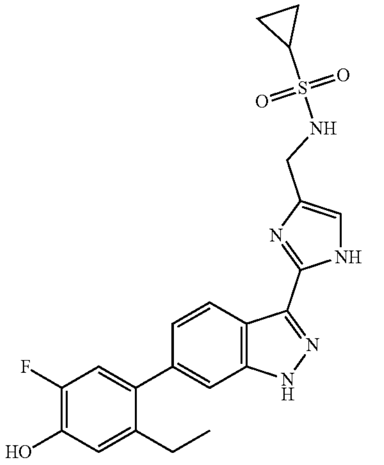

Synthetic Route of Ex-18

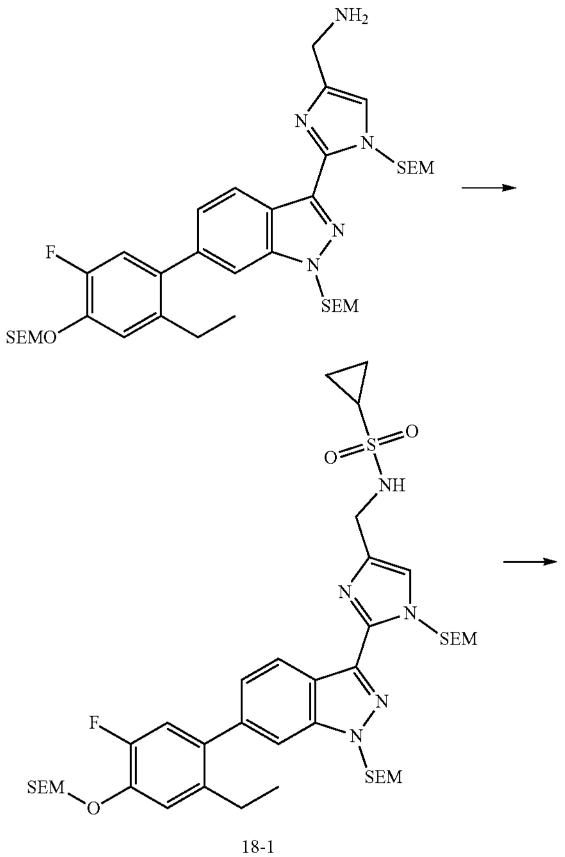

18-1

-continued

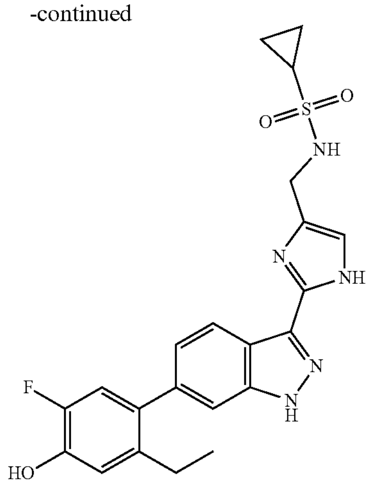

Ex-18

Synthesis Method

Synthesis of Intermediate 18-1: N-((2-(6-(2-ethyl-5-fluoro-4-((2-(trimethyl silyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)cyclopropanesulfonamide (2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazole-4-yl)methanamine (30.0 mg, 0.04 mmol), TEA (13.1 mg, 0.12 mmol), and 5 ml of DCM were added. It was allowed to cool to 0° C., to which cyclopropanesulfonyl chloride (7.4 mg, 0.05 mmol) was added dropwise. After the dropwise addition was complete, the reaction mixture was heated to room temperature and it was allowed to react for 1 hour. After the reaction was completed, the reaction mixture was quenched with water and extracted with DCM. The layers were separated and the resulting organic phase was washed with saturated sodium chloride solution and dried over anhydrous sodium sulfate. It was concentrated and purified to obtain 24 mg of colorless oil with a yield of 70.0%.

Synthesis of Compound Ex-18: N-((2-(6-(2-ethyl-5-fluoro-4-hydroxyphenyl)-1H-indazol-3-yl)-1H-imidazol-4-yl)methyl)cyclopropanesulfonamide The intermediate 18-1 (24 mg, 0.03 mmol), 2 ml methanol, and 2 ml concentrated hydrochloric acid were added. It was allowed to react at 50° C. for 6 hours and concentrated. To the resulting residue were added 4 ml methanol, and 0.5 ml of aqueous ammonia. It was concentrated and purified on a silica gel plate to obtain 8 mg of white solid with a yield of 61.3%. LC-MS m/z (ESI) [M+H]+ calculated for $C_{22}H_{23}FN_5O_3S$: 456.1; found: 456.1.

Example 19: N-((2-(6-(2-ethyl-5-fluoro-4-hydroxyphenyl)-1H-indazol-3-yl)-1H-imidazol-4-yl)methyl) ethanesulfonamide (Ex-19)

Ex-19

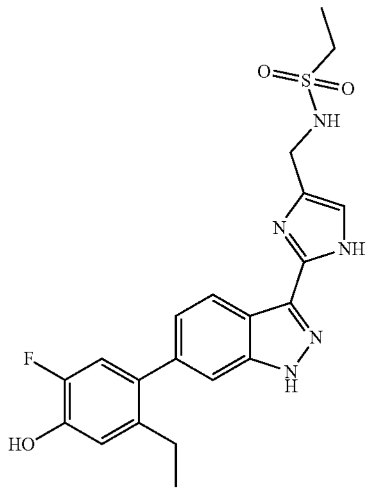

Synthetic Route of Ex-19

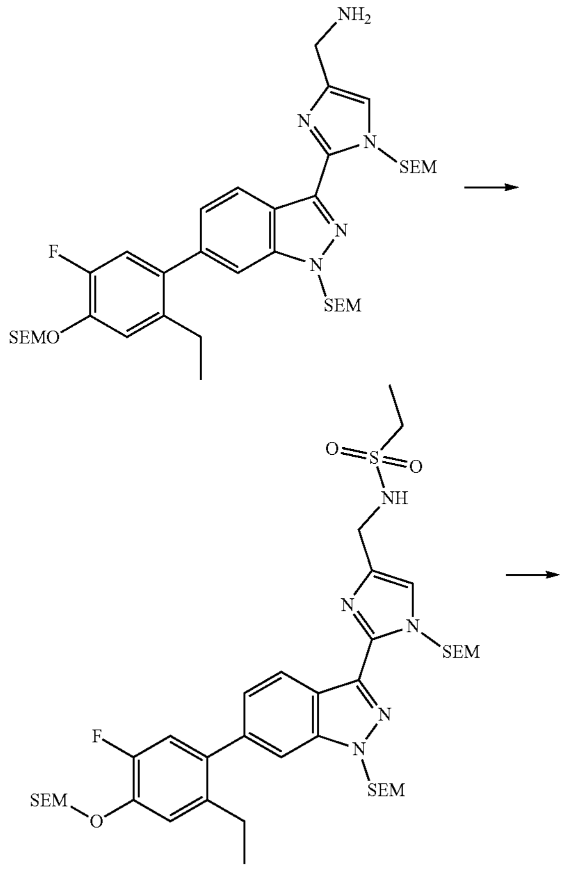

19-1

-continued

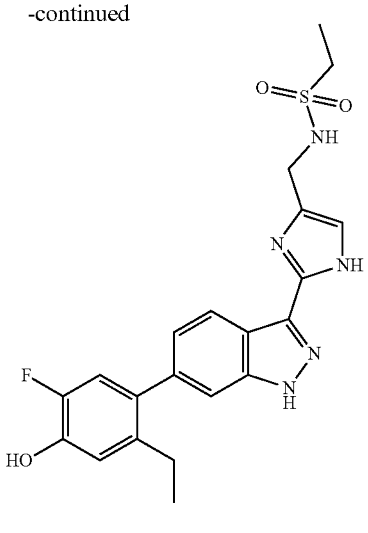

Ex-19

Synthesis Method

Synthesis of Intermediate 19-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)ethane sulfonamide (2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazole-4-yl)methanamine (30.0 mg, 0.04 mmol), TEA (12.3 mg, 0.12 mmol), and 5 ml of DCM were added. It was allowed to cool to 0° C., to which ethylsulfonyl chloride (7.8 mg, 0.06 mmol) was added dropwise. After the dropwise addition was complete, and the reaction was carried out at room temperature for 1 hour. After the reaction was completed, water was added for quenching, DCM was added for extraction, and the layers were separated. The organic phase was washed with saturated sodium chloride solution and dried over anhydrous sodium sulfate. Concentrated column chromatography gave 22 mg of colorless oil, yield: 65.16%.

Synthesis of Compound Ex-19: N-((2-(6-(2-ethyl-5-fluoro-4-hydroxyphenyl)-1H-indazol-3-yl)-1H-imidazol-4-yl)methyl)ethanesulfonamide The intermediate 19-1 (22 mg, 0.03 mmol), 4 ml methanol, and 2 ml concentrated hydrochloric acid were added. It was allowed to react at 50° C. for 6 hours and concentrated. To the resulting residue were added 4 ml methanol, and 0.5 ml of aqueous ammonia. It was concentrated and purified on a silica gel plate to obtain 3 mg of white solid with a yield of 25.7%. LC-MS m/z (ESI) [M+H]+ calculated for $C_{21}H_{23}FN_5O_3S$: 444.1; found: 444.1.

Example 20: N-((2-(6-(2-ethyl-5-fluoro-4-hydroxyphenyl)-1H-indazol-3-yl)-1H-imidazol-4-yl)methyl)-4-hydroxypiperidine-1-carboxamide (Ex-20)

Ex-20

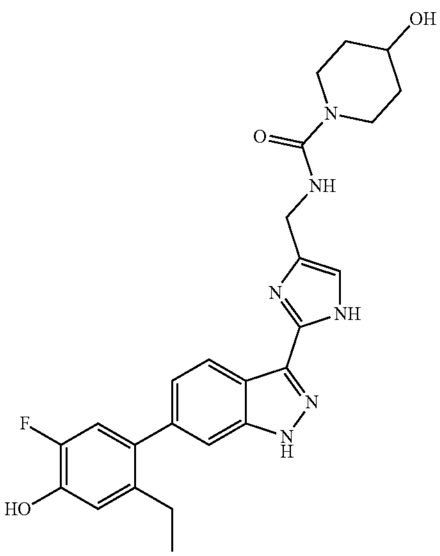

Synthetic Route of Ex-20

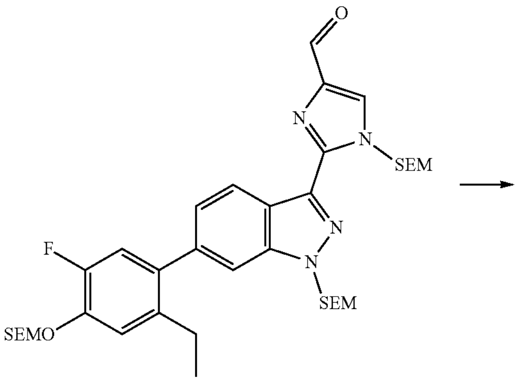

-continued

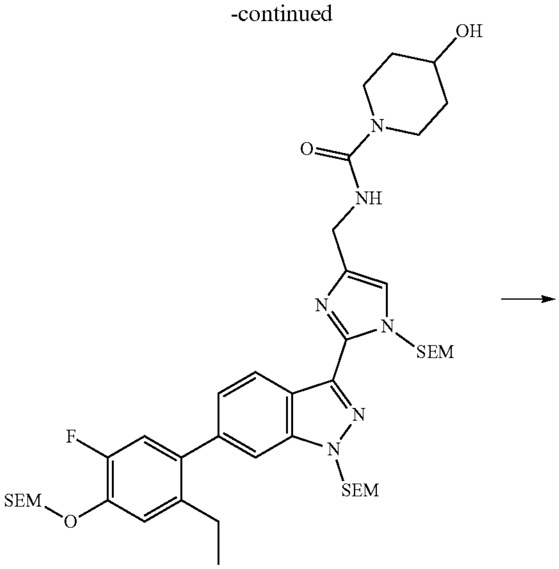

20-1

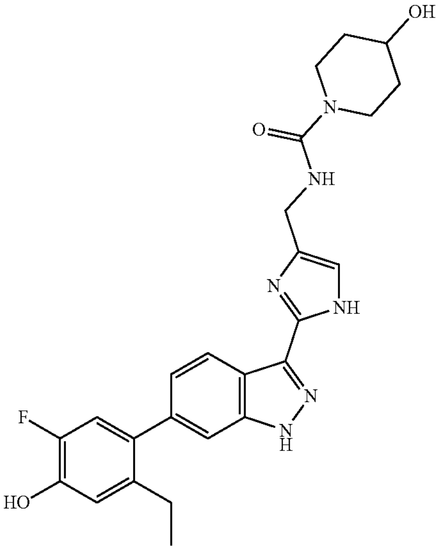

Ex-20

Synthesis Method

Synthesis of Intermediate 20-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-4-hydroxy piperidine-1-carboxamide (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl) methylamine (25.0 mg, 0.03 mmol) was dissolved in 5 ml of anhydrous dichloromethane and then was cooled to 0° C. Triphosgene (10.0 mg, 0.03 mmol) was added and it was allowed to react for 5 minutes. And then triethylamine (34.1 mg, 0.34 mmol) was added slowly and it was allowed to react for 30 minutes. After that, 4-hydroxypiperidine (4.1 mg, 0.04 mmol) was added and it was allowed to react at room temperature for 1 hour. Water was added to the reaction mixture and the resulting reaction mixture was extracted twice with dichloromethane. The resulting organic phases were combined, washed with saturated brine, dried over anhydrous sodium sulfate, concentrated and purified to obtain 19.1 mg of intermediate 20-1 with a yield of 65.2%.

Synthesis of Compound Ex-20: N-((2-(6-(2-ethyl-5-fluoro-4-hydroxyphenyl)-1H-indazol-3-yl)-1H-imidazol-4-yl)methyl)-4-hydroxypiperidine-1-carboxamide The intermediate 20-1 (19.1 mg, 0.02 mmol) was dissolved in 2 ml methanol, to which 1 ml of concentrated hydrochloric acid was added. It was allowed to react at 50° C. for 6 hours. The reaction mixture was concentrated and dissolved in 2 ml methanol, to which 0.5 ml of aqueous ammonia was added. The resulting mixture was concentrated and purified by a preparative silica gel plate to obtain 3.6 mg of final product with a yield of 34.2%.

$^1$H NMR (400 MHz, MeOD) δ 8.29 (d, J=8.0 Hz, 1H), 7.43 (d, J=4.0 Hz, 1H), 7.19 (dd, J=4.0 Hz, J=8.0 Hz, 1H), 7.09 (s, 1H), 6.95 (dd, J=12.0 Hz, J=20.0 Hz, 2H), 4.44 (s, 2H), 3.90-3.78 (m, 3H), 3.13-3.06 (m, 2H), 2.59-2.53 (m, 2H), 1.90-1.85 (m, 2H), 1.48-1.45 (m, 2H), 1.08 (t, J=8.0 Hz, 3H).

Example 21: (R)—N-((2-(6-(2-ethyl-5-fluoro-4-hydroxyphenyl)-1H-indazol-3-yl)-1H-imidazol-4-yl)methyl)-3-hydroxy-N-methylpyrrolidine-1-carboxamide (Ex-21)

Ex-21

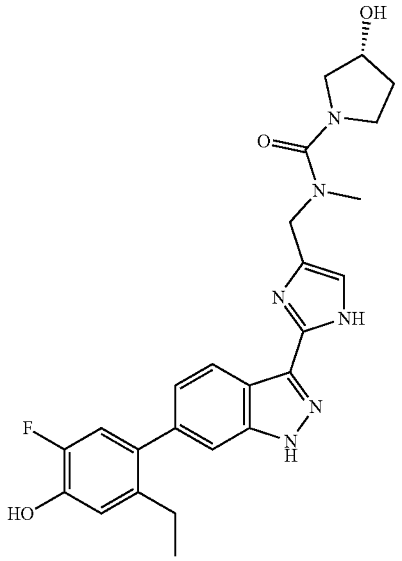

Synthetic Route of Ex-21

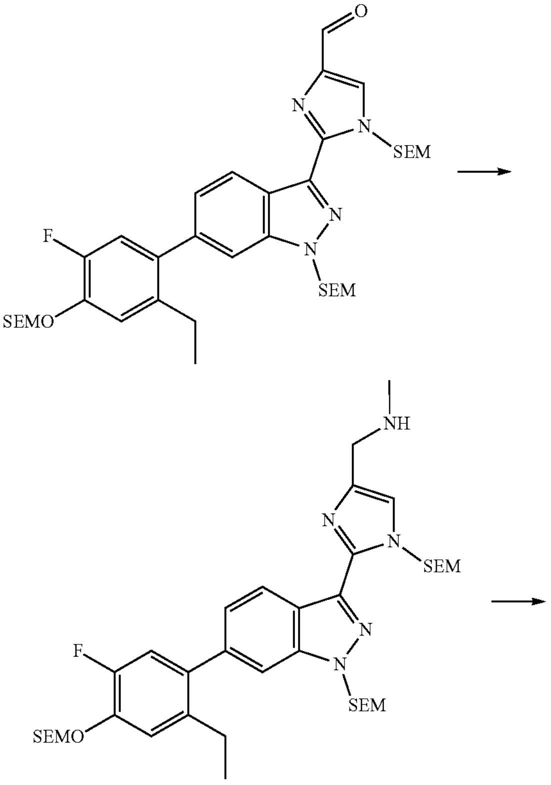

21-1

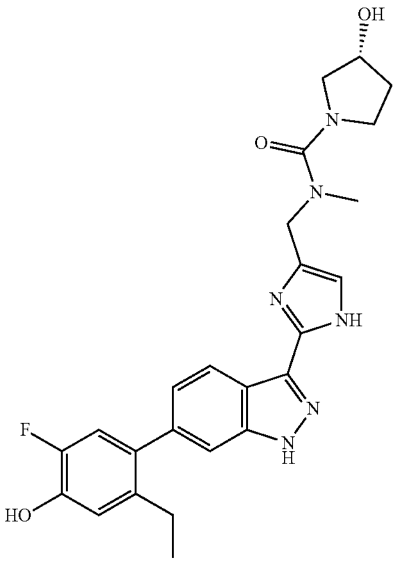

Ex-21

Synthesis Method

Synthesis of Intermediate 21-1: 1-(2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)-N-methylmethylamine 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (50 mg, 0.07 mmol) and methylamine hydrochloride (5.3 mg, 0.08 mmol) were dissolved in DCM, to which triethylamine (9.8 mg, 0.10 mmol) was added. It was allowed to react at room temperature for 0.5 hours. To the reaction mixture was added sodium triacetylborohydride (28.6 mg, 0.13 mmol) and it was allowed to react at room temperature for 1.5 hours. Water was added to the reaction solution, and the resulting mixture was extracted twice with DCM, and the organic phases were combined, washed with saturated brine, dried over anhydrous sodium sulfate, concentrated and purified on silica gel plate to obtain 37 mg of intermediate 21-1 with a yield of 72.5%.

$^1$H NMR (400 MHz, $CDCl_3$) δ 8.48 (d, J=8.0 Hz, 1H), 7.44 (d, J=12.0 Hz, 2H), 7.24 (d, J=8.0 Hz, 1H), 7.15 (d, J=8.0 Hz, 1H), 6.99 (d, J=12.0 Hz, 1H), 5.91 (s, 2H), 5.75 (s, 2H), 5.32 (s, 2H), 4.14 (s, 2H), 3.86 (t, J=10.0 Hz, 2H), 3.56-3.62 (m, 4H), 2.71 (s, 3H), 2.51-2.57 (m, 2H), 1.05 (t, J=8.0 Hz, 3H), 0.86-0.91 (m, 6H), 0.02-0.04 (m, 9H), −0.10-−0.07 (m, 18H).

Synthesis of Compound Ex-21: (R)—N-((2-(6-(2-ethyl-5-fluoro-4-hydroxy phenyl)-1H-indazol-3-yl)-1H-imidazol-4-yl)methyl)-3-hydroxy-N-methylpyrrolidine-1-carboxamide Triphosgene (14.5 mg, 0.05 mmol) was dissolved in DCM, and cooled to zero. To the resulting solution was added intermediate 21-1 (37 mg, 0.05 mmol) in DCM. It was allowed to react for 5 minutes. Then triethylamine (14.8 mg, 0.15 mmol) was dropwise added slowly. It was allowed to react at 0° C. for 0.5 hours. Then (R)-pyrrolidin-3-ol (6.4 mg, 0.07 mmol) in DCM was added. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified. The obtained product was dissolved in 2 ml of methanol and 1 ml of concentrated hydrochloric acid. It was allowed to react at 50° C. for 6 hours. The reaction mixture was concentrated and dissolved in 3 ml of methanol, to which 0.5 ml of aqueous ammonia was added. And then it was concentrated and purified by preparative silica gel plate to obtain 11 mg of the final product with a yield of 47.0%.

$^1$H NMR (400 MHz, MeOD) δ 8.28 (d, J=8.0 Hz, 1H), 7.43 (s, 1H), 7.17-7.19 (m, 2H), 6.90-6.97 (m, 2H), 4.47 (s, 2H), 4.40-4.42 (m, 1H), 3.62-3.75 (m, 2H), 3.49-3.54 (m, 1H), 3.37-3.38 (m, 1H), 2.94 (s, 3H), 2.53-2.58 (m, 2H), 1.90-2.01 (m, 2H), 1.08 (t, J=8.0 Hz, 3H).

Example 22: (R)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide (Ex-22)

Ex-22

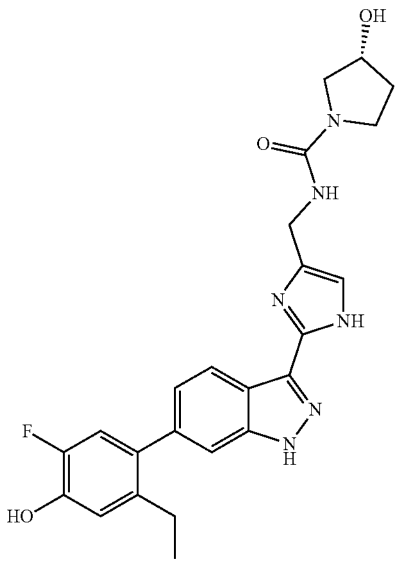

Synthetic Route of Ex-22

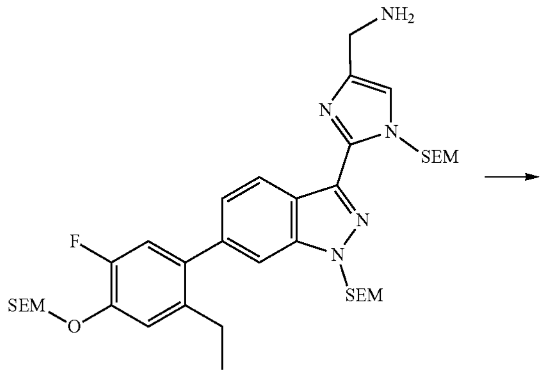

-continued

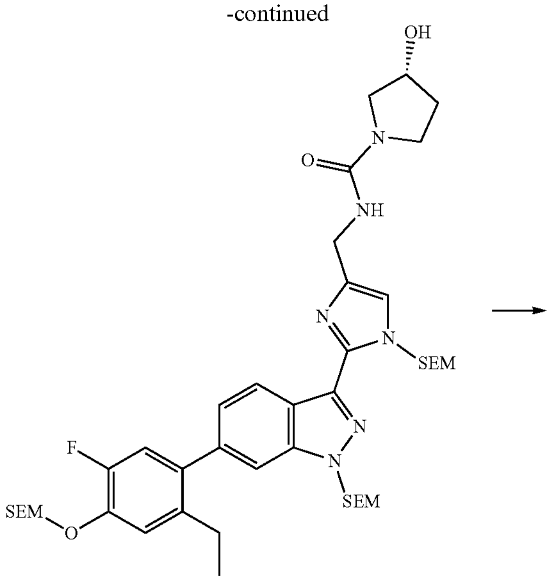

22-1

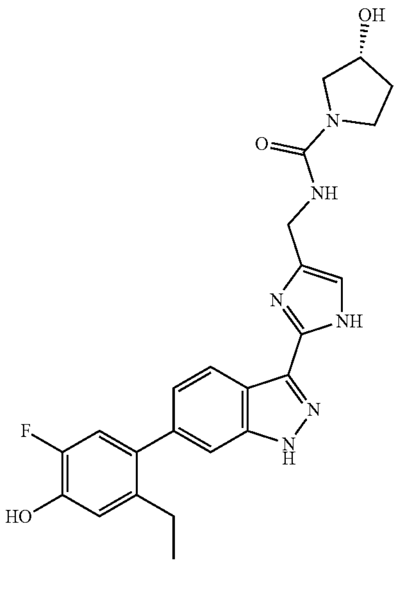

Ex-22

Synthesis Method

Synthesis of Intermediate 22-1: (R)—N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-3-hydroxy pyrrolidine-1-carboxamide (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl) methylamine (25.0 mg, 0.03 mmol) was dissolved in 5 ml of anhydrous dichloromethane, and was cooled to 0° C., to which triphosgene (10.0 mg, 0.03 mmol) was added. It was allowed to react for 5 minutes. And then triethylamine (34.1 mg, 0.34 mmol) was added slowly and it was allowed to react for 30 minutes. After that (R)-pyrrolidin-3-ol (3.5 mg, 0.04 mmol) was added and it was allowed to react at room temperature for 1 hour. Water was added to the reaction solution, the resulting mixture was extracted twice with dichloromethane, and the organic phases were combined, washed with saturated brine, dried over anhydrous sodium sulfate, and concentrated and purified to obtain 21.0 mg of intermediate 22-1 with a yield of 72.9%.

Synthesis of Compound Ex-22: (R)—N-((2-(6-(2-ethyl-5-fluoro-4-hydroxyphenyl)-1H-indazol-3-yl)-1H-imidazole-4-yl)methyl)-3-hydroxypyrrolidine-1-carboxamide The intermediate 22-1 (21.0 mg, 0.02 mmol) was dissolved in 2 ml of methanol to which 1 ml of concentrated hydrochloric acid was added. It was allowed to react at 50° C. for 6 hours. The reaction mixture was concentrated and dissolved in 2 ml of methanol, to which 0.5 ml of aqueous ammonia was added. And then it was concentrated and purified by preparative silica gel plate to obtain 6.7 mg of the final product with a yield of 58.6%.

$^1$H NMR (400 MHz, MeOD) δ 8.29 (d, J=8.0 Hz, 1H), 7.43 (d, J=4.0 Hz, 1H), 7.19 (d, J=8.0 Hz, 1H), 7.11 (s, 1H), 6.95 (dd, J=12.0 Hz, J=20.0 Hz, 2H), 4.45-4.43 (m, 3H), 3.54-3.49 (m, 3H), 3.40-3.37 (m, 1H), 2.59-2.53 (m, 2H), 2.08-2.02 (m, 2H), 1.08 (t, J=8.0 Hz, 3H).

Example 23: (S)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide (Ex-23)

Ex-23

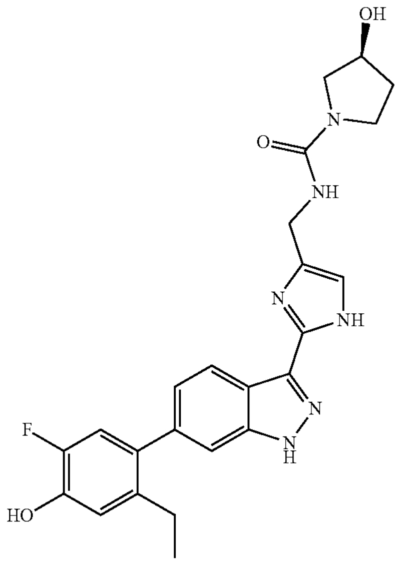

Synthetic Route of Ex-23

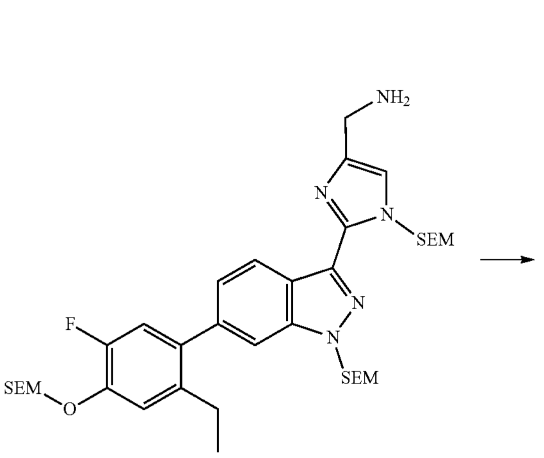

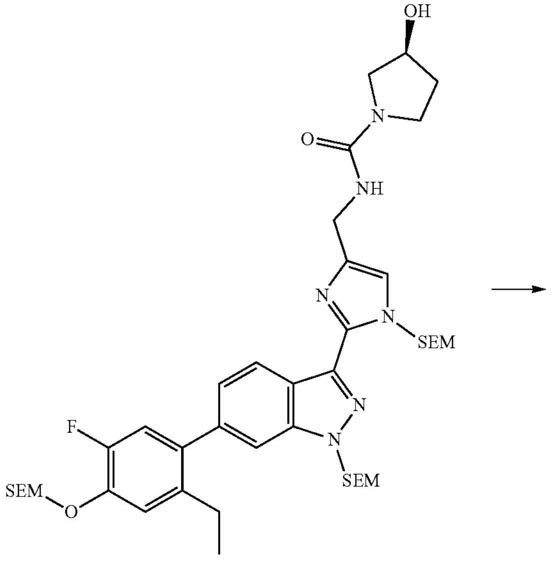

23-1

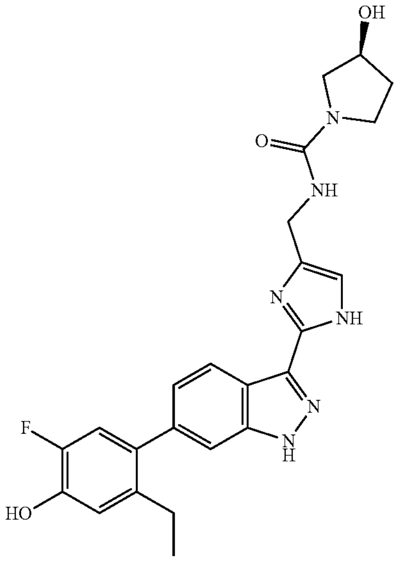

Ex-23

Synthesis Method

Synthesis of Intermediate 23-1: (S)—N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-3-hydroxy pyrrolidine-1-carboxamide (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methylamine (25.0 mg, 0.03 mmol) was dissolved in 5 ml of anhydrous dichloromethane, and was cooled to 0° C., to which triphosgene (10.0 mg, 0.03 mmol) was added. It was allowed to react for 5 minutes. And then triethylamine (34.1 mg, 0.34 mmol) was added slowly and it was allowed to react for 30 minutes. After that (S)-pyrrolidin-3-ol (3.5 mg, 0.04 mmol) was added and it was allowed to react at room temperature for 1 hour. Water was added to the reaction solution, the resulting mixture was extracted twice with dichloromethane, and the organic phases were combined, washed with saturated brine, dried over anhydrous sodium sulfate, and concentrated and purified to obtain 17.8 mg of intermediate 22-1 with a yield of 61.6%.

Synthesis of Compound Ex-23: (S)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide The intermediate 23-1 (17.8 mg, 0.02 mmol) was dissolved in 2 ml of methanol to which 1 ml of concentrated hydrochloric acid was added. It was allowed to react at 50° C. for 6 hours. The reaction mixture was concentrated and dissolved in 2 ml of methanol, to which 0.5 ml of aqueous ammonia was added. And then it was concentrated and purified by preparative silica gel plate to obtain 4.2 mg of the final product with a yield of 43.5%.

$^1$H NMR (400 MHz, MeOD) δ 8.29 (d, J=8.0 Hz, 1H), 7.43 (d, J=4.0 Hz, 1H), 7.19 (d, J=8.0 Hz, 1H), 7.10 (s, 1H), 6.95 (dd, J=12.0 Hz, J=20.0 Hz, 2H), 4.45-4.43 (m, 3H), 3.53-3.49 (m, 3H), 3.40-3.37 (m, 1H), 2.59-2.53 (m, 2H), 2.07-2.03 (m, 2H), 1.08 (t, J=8.0 Hz, 3H).

Example 24: 5-ethyl-2-fluoro-4-(3-(4-(((2-hydroxyethyl)(methyl)amino) methyl)-1H-imidazol-2-yl)-1H-indazol-6-yl)phenol (Ex-24)

Ex-24

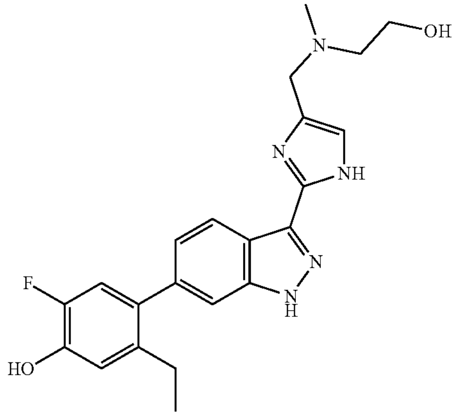

Synthetic Route of Ex-24

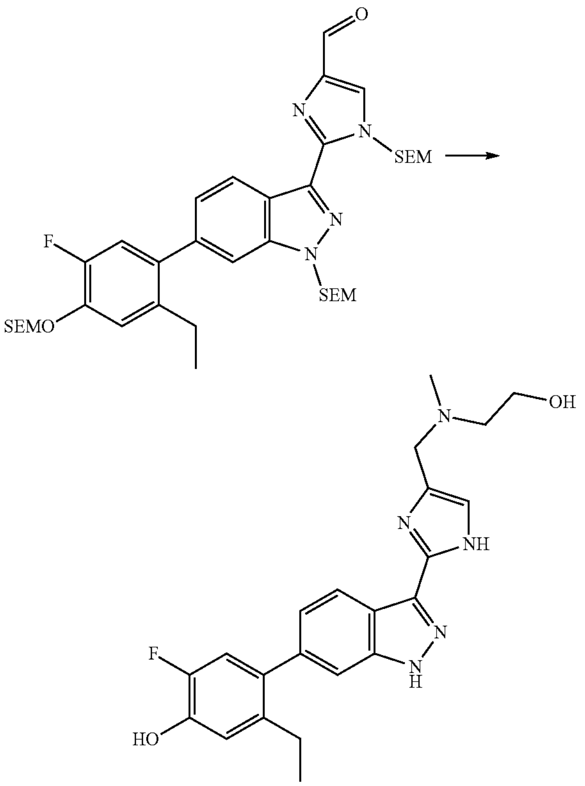

Ex-24

Synthesis Method

Synthesis of Compound Ex-24: 5-ethyl-2-fluoro-4-(3-(4-(((2-hydroxyethyl)(methyl)amino)methyl)-1H-imidazol-2-yl)-1H-Indazol-6-yl)phenol 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (20 mg, 0.03 mmol) and 2-(methylamino)ethane-1-ol (3 mg, 0.04 mmol) were dissolved in DCM. It was allowed to react at room temperature for 0.5 hours. To the reaction solution was added sodium triacetylborohydride (8.2 mg, 0.04 mmol). It was allowed to react at room temperature for 1.5 hour, to which water was added, and then the reaction solution was extracted twice with DCM. The resulting organic phases was combined, washed with saturated brine, and dried over anhydrous sodium sulfate. It was concentrated and purified on silica gel plate. The purified concentrate was dissolved in 2 ml of methanol to which 1 ml of concentrated hydrochloric acid was added. It was allowed to react at 50° C. for 6 hours. The reaction mixture was concentrated and dissolved in 3 ml of methanol, to which 0.5 ml of aqueous ammonia was added. And then it was concentrated and purified by a silica gel plate to obtain 4.8 mg of the final product with a yield of 43.4%.

$^1$H NMR (400 MHz, MeOD) δ 8.34 (d, J=8.0 Hz, 1H), 7.51 (s, 1H), 7.45 (s, 1H), 7.22-7.17 (m, 1H), 7.00-6.89 (m, 2H), 4.47 (s, 2H), 3.98 (t, J=4.0 Hz, 2H), 3.43-3.37 (m, 2H), 3.00 (s, 3H), 2.60-2.51 (m, 2H), 1.08 (t, J=8.0 Hz, 3H).

Example 25: N-((2-(6-(2-ethyl-5-fluoro-4-hydroxyphenyl)-1H-indazol-3-yl)-1H-imidazol-4-yl)methyl)propane-2-sulfonamide (Ex-25)

Ex-25

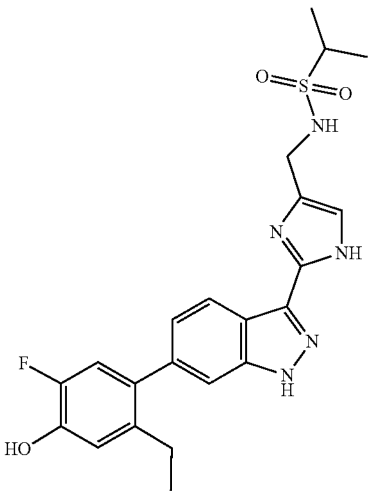

Synthetic Route of Ex-25

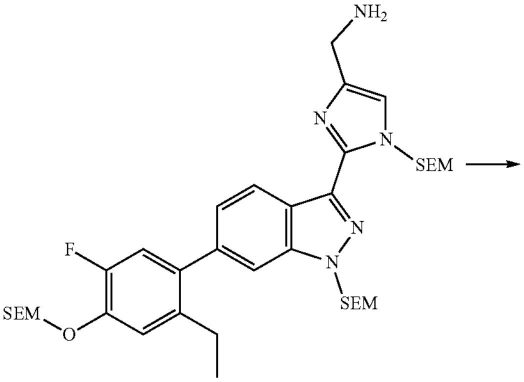

-continued

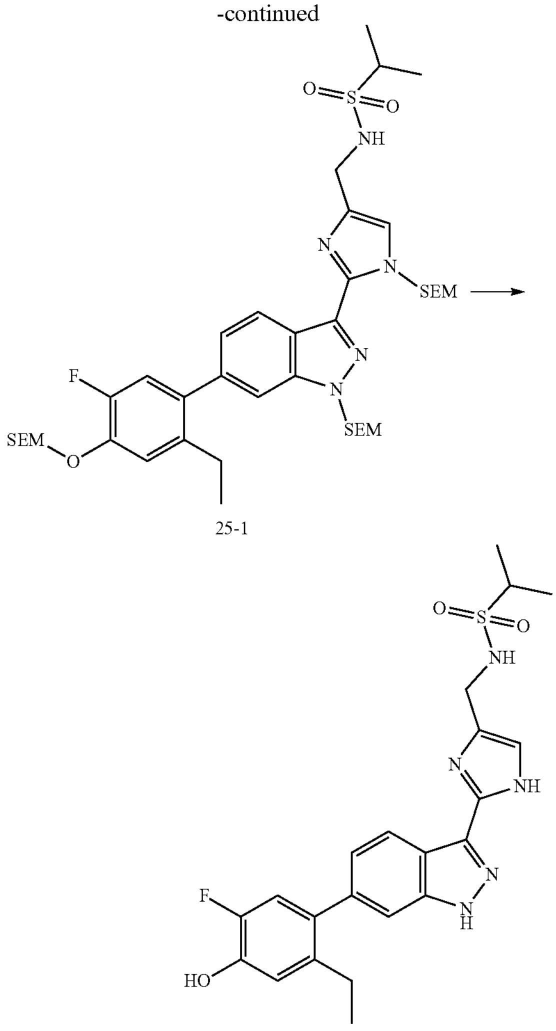

25-1

Ex-25

Synthesis Method

Synthesis of Intermediate 25-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)propane-2-sulfonamide (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (17.0 mg, 0.02 mmol), TEA (7.0 mg, 0.07 mmol), and 5 ml of DCM were added. The resulting mixture was cooled to 0° C., to which propane 2-sulfonyl chloride (7.4 mg, 0.05 mmol) was added dropwise. After the dropwise addition was complete, it was allowed to react at room temperature for 1 hour. After the reaction was completed, the reaction mixture was quenched with water, and extracted with DCM. The layers were separated. The resulting organic phase was washed with saturated sodium chloride solution and dried over anhydrous sodium sulfate. It was concentrated and purified to obtain 11 mg of colorless oil with a yield of 56.6%.

Synthesis of Compound Ex-25: N-((2-(6-(2-ethyl-5-fluoro-4-hydroxyphenyl)-1H-indazol-3-yl)-1H-imidazol-4-yl)methyl)propane-2-sulfonamide The intermediate 25-1 (11 mg, 0.01 mmol), 4 ml methanol, and 2 ml concentrated hydrochloric acid were added. It was allowed to react at 50° C. for 6 hours. The reaction mixture was concentrated and to the resulting concentrate were added 4 ml methanol, and 0.5 ml of aqueous ammonia. It was concentrated and purified on a preparative silica gel plate to obtain 3 mg of white solid with a yield of 50.5%. LC-MS m/z (ESI) [M+H]+ calculated for $C_{22}H_{25}FN_5O_3S$: 458.1; found: 458.1.

Example 26: methyl ((2-(6-(2-ethyl-5-fluoro-4-hydroxyphenyl)-1H-indazol-3-yl)-1H-imidazol-4-yl)methyl)carbamate (Ex-26)

Ex-26

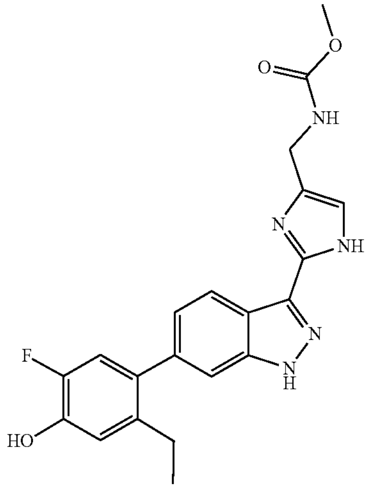

Synthetic Route of Ex-26

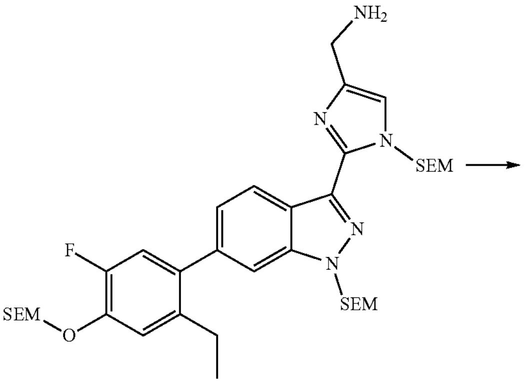

-continued

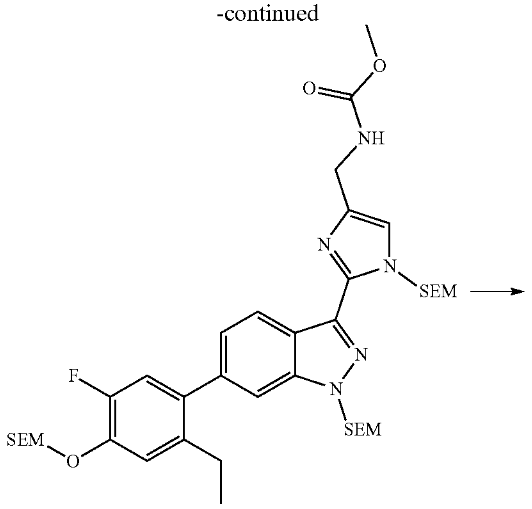

26-1

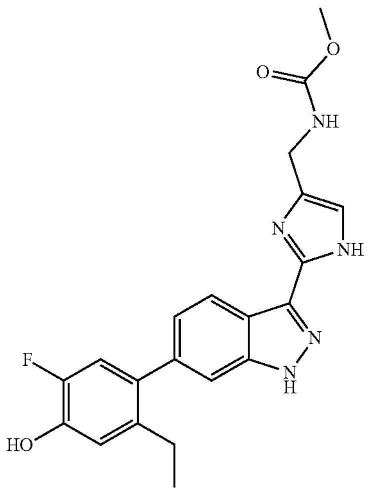

Ex-26

Synthesis Method

Synthesis of Intermediate 26-1: methyl ((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)carbamate (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl) methylamine (30.0 mg, 0.04 mmol) was dissolved in 5 ml of anhydrous dichloromethane, and was cooled to 0° C., to which triphosgene (11.9 mg, 0.04 mmol) was added. It was allowed to react for 5 minutes. And then triethylamine (40.4 mg, 0.40 mmol) was added slowly and it was allowed to react for 30 minutes. The reaction mixture was concentrated and was dissolved in 2 ml of methanol. After that DMAP (4.9 mg, 0.04 mmol) was added. The resulting mixture was added to 70° C. and it was allowed to react for 4 hour. Water was added to the reaction solution, the resulting mixture was extracted twice with dichloromethane, and the organic phases were combined, washed with saturated brine, dried over anhydrous sodium sulfate, and concentrated and purified to obtain 17.9 mg of intermediate 26-1 with a yield of 55.3%.

Synthesis of Compound Ex-26: methyl ((2-(6-(2-ethyl-5-fluoro-4-hydroxyphenyl)-1H-indazol-3-yl)-1H-imidazol-4-yl)methyl) carbamate The intermediate 26-1 (17.9 mg, 0.02 mmol) was dissolved in 2 ml of methanol to which 1 ml of concentrated hydrochloric acid was added. It was allowed to react at 50° C. for 6 hours. The reaction mixture was concentrated and dissolved in 2 ml of methanol, to which 0.5 ml of aqueous ammonia was added. And then it was concentrated and purified by preparative silica gel plate to obtain 3.9 mg of the final product with a yield of 42.5%.

$^1$H NMR (400 MHz, MeOD) δ 8.29 (dd, J=4.0 Hz, J=8.0 Hz, 1H), 7.42 (s, 1H), 7.17 (dd, J=4.0 Hz, J=8.0 Hz, 1H), 7.10 (s, 1H), 6.95 (dd, J=12.0 Hz, J=20.0 Hz, 2H), 4.39 (s, 2H), 3.70 (s, 3H), 2.58-2.53 (m, 2H), 1.08 (t, J=8.0 Hz, 3H).

Example 27: 2-cyanoethyl ((2-(6-(2-ethyl-5-fluoro-4-hydroxyphenyl)-1H-indazol-3-yl)-1H-imidazol-4-yl)methyl) carbamate (Ex-27)

Ex-27

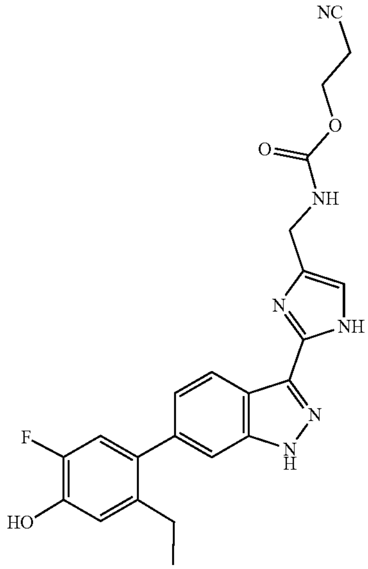

Synthetic Route of Ex-27

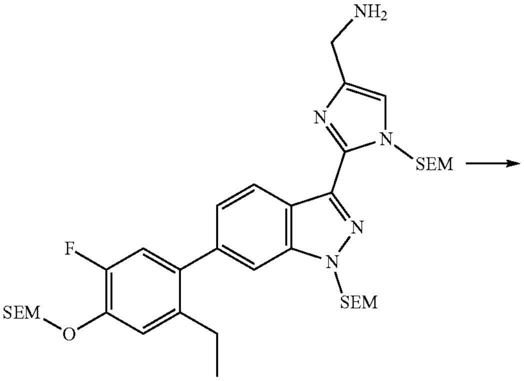

-continued

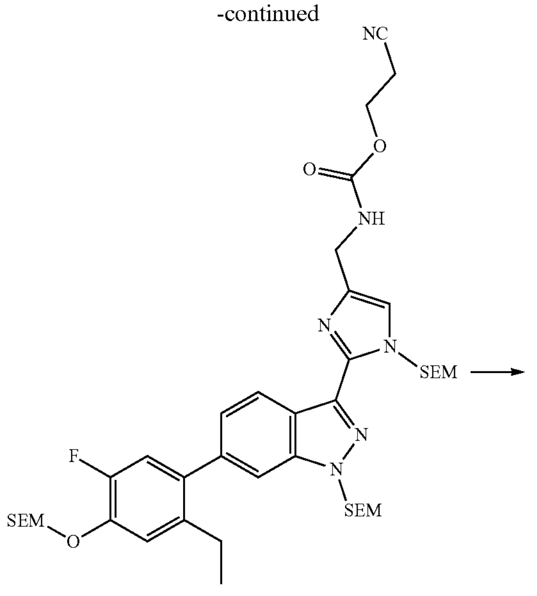

26-1

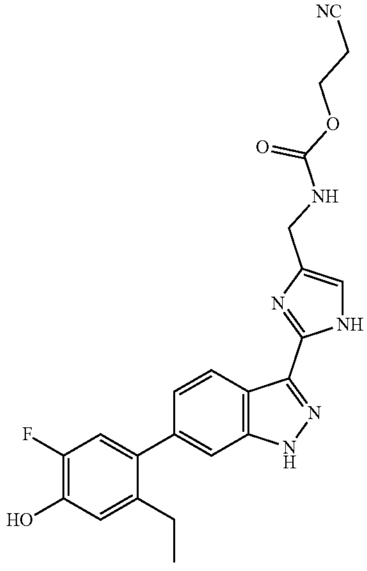

Ex-27

Synthesis Method

Synthesis of Intermediate 27-1: 3-cyanoethyl ((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)carbamate 3-Hydroxypropionitrile (10.1 mg, 0.14 mmol), 5 ml of DMF, 0.2 ml of triethylamine, and CDI (10.0 mg, 0.06 mmol) were added. It was allowed to react for 10 minutes. To the reaction mixture, (2-(6-(2-ethyl-5-fluoro-4-((2-(trimethylsilyl) ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (30.0 mg, 0.04 mmol), and DMAP (0.6 mg, 0.005 ml) were added. It was allowed to react at room temperature for 17 h. After the reaction is completed, the reaction mixture was quenched with water and extracted with EA. The resulting organic phase was washed with aqueous ammonium chloride solution, washed with saturated sodium chloride solution, and dried over with anhydrous sodium sulfate. It was concentrated and purified by column chromatography to obtain 19 mg of colorless oil with a yield of 57%.

Synthesis of Compound Ex-27: 2-cyanoethyl ((2-(6-(2-ethyl-5-fluoro-4-hydroxyphenyl)-1H-indazol-3-yl)-1H-imidazole-4-yl)methyl)carbamate The intermediate 27-1 (19 mg, 0.02 mmol), 4 ml of 1,4-dioxane, and 2 ml of concentrated hydrochloric acid were added. It was allowed to react at 50° C. for 4 hours. The reaction mixture was concentrated and to the resulting concentrate were added 4 ml of 1,4-dioxane, and 0.5 ml of aqueous ammonia. It was concentrated and purified on a preparative silica gel plate to obtain 2 mg of white solid with a yield of 20.0%. LC-MS m/z (ESI) [M+H]+ calculated for $C_{23}H_{22}FN_6O_3$: 449.2; found: 449.2.

Example 28: N-((2-(6-(2-ethyl-5-fluoro-4-hydroxyphenyl)-1H-indazol-3-yl)-1H-imidazol-4-yl)methyl)cyclobutanecarboxamide (Ex-28)

Ex-28

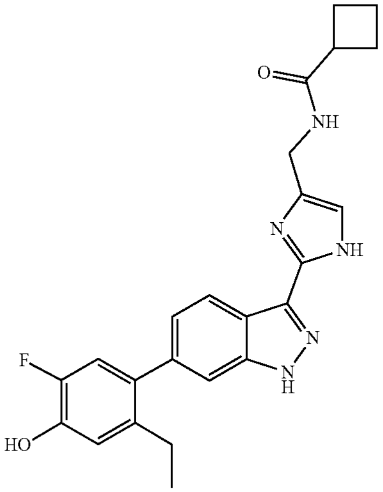

Synthetic Route of Ex-28

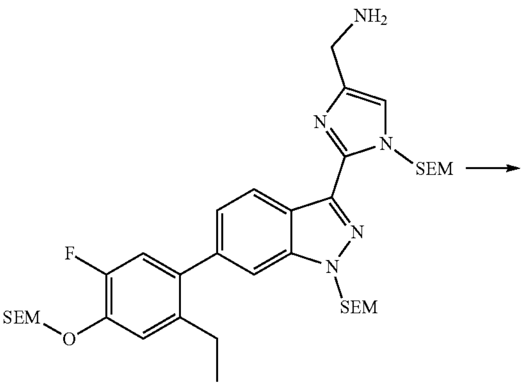

-continued

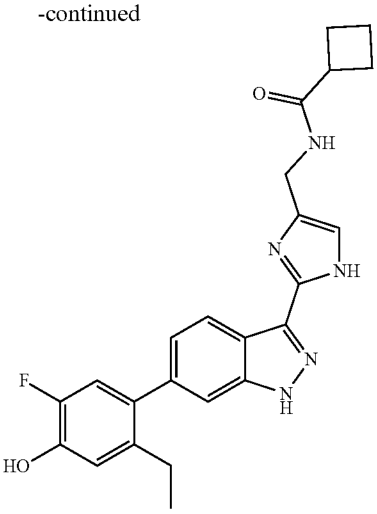

Ex-28

Synthesis Method

Synthesis of Compound Ex-28: N-((2-(6-(2-ethyl-5-fluoro-4-hydroxyphenyl)-1H-indazol-3-yl)-1H-imidazol-4-yl) methyl)cyclobutanecarboxamide (2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methylamine (30.0 mg, 0.04 mmol) was dissolved in 5 ml of anhydrous dichloromethane, to which triethylamine (4.9 mg, 0.05 mmol) and cyclobutylcarbonyl chloride (7.2 mg, 0.06 mmol) were added. It was allowed to react at room temperature for 1 hour. The reaction mixture was quenched with water, and extracted twice with dichloromethane. The resulting organic phases was combined, washed with saturated brine, and dried over anhydrous sodium sulfate. It was concentrated to obtain coarse product. The obtained product was dissolved in 4 ml of methanol to which 2 ml of concentrated hydrochloric acid was added. It was allowed to react at 50° C. for 6 hours. The reaction mixture was concentrated and dissolved in 2 ml of methanol, to which 0.5 ml of aqueous ammonia was added. And then the resulting mixture was concentrated and purified by preparative plate to obtain 7.0 mg of the final product with a yield of 39.9%.

$^1$H NMR (400 MHz, MeOD) δ 8.28 (d, J=8.4 Hz, 1H), 7.42 (s, 1H), 7.17 (dd, J=1.4 Hz, J=8.4 Hz, 1H), 7.10 (s, 1H), 6.93 (dd, J=11.8 Hz, J=21.8 Hz, 2H), 4.45 (s, 2H), 3.22-3.14 (m, 1H), 2.55 (q, J=7.6 Hz, 2H), 2.37-2.27 (m, 2H), 2.23-2.13 (m, 2H), 2.07-1.96 (m, 2H), 1.08 (t, J=7.6 Hz, 3H).

Example 29: N-((2-(6-(2-ethyl-5-fluoro-4-hydroxyphenyl)-1H-indazol-3-yl)-1H-imidazol-4-yl)methyl)-1-methylpyrrolidine-3-carboxamide (Ex-29)

Ex-29

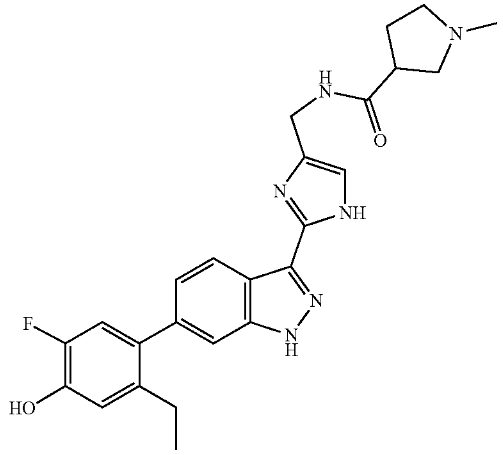

Synthetic Route of Ex-29

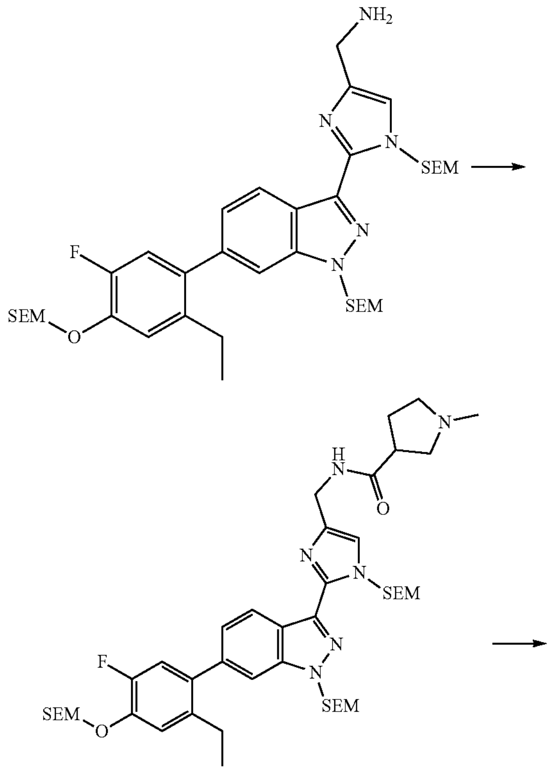

29-1

-continued

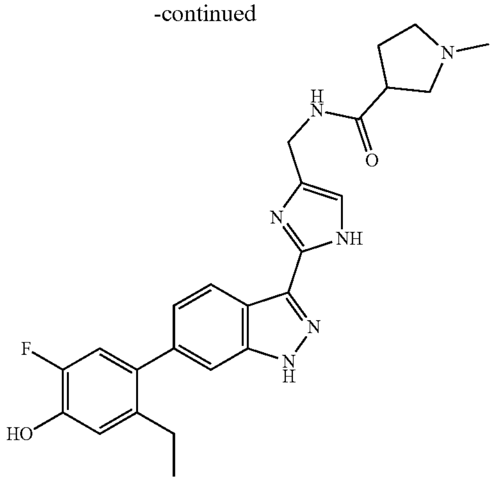

Ex-29

Synthesis Method

Synthesis of Intermediate 29-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-1-methyl pyrrolidine-3-carboxamide (2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (50.0 mg, 0.07 mmol), 1-methylpyrrolidine-3-carboxylic acid (28.0 mg, 0.16 mmol), HATU (46.8 mg, 0.12 mmol), 10 ml DMF, and 0.4 ml DIEA were added. The resulting mixture was stirred at room temperature for 2 h. After the reaction was completed, the reaction mixture was quenched with water and extracted with EA. The layers were separated, and dried over anhydrous sodium sulfate. It was concentrated and separated by column chromatography to obtain 28 mg of colorless oil with a yield of 40.0%.

Synthesis of Compound Ex-29: N-((2-(6-(2-ethyl-5-fluoro-4-hydroxy phenyl)-1H-indazol-3-yl)-1H-imidazol-4-yl)methyl)-1-methylpyrrolidine-3-carboxamide Intermediate 29-1 (28.0 mg, 0.03 mmol), 6 ml of MeOH, and 3 ml of concentrated hydrochloric acid were added. It was allowed to react at 50° C. for 6 hours. The reaction mixture was concentrated, to which 4 ml of methanol and 0.5 ml of aqueous ammonia were added. The resulting mixture was concentrated and purified by a preparative silica gel plate to obtain 2 mg of white solid with a yield of 13.1%. LC-MS m/z (ESI) [M+H]+ calcd for $C_{25}H_{28}FN_6O_2$: 463.2; Found: 463.2.

Example 30: 4-(3-(4-((2-azabicyclo[2.2.2]octan-2-yl)methyl)-1H-imidazol-2-yl)-1H-indazol-6-yl)-5-ethyl-2-fluorophenol (Ex-30)

Ex-30

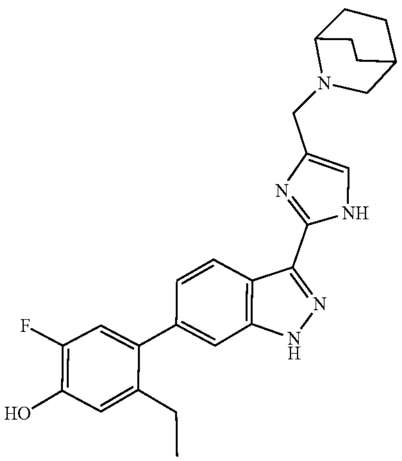

Synthetic Route of Ex-30

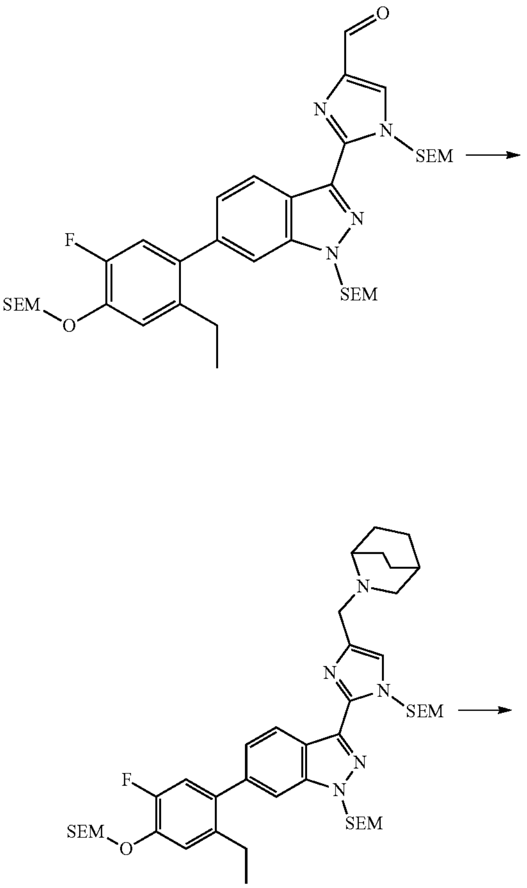

30-1

-continued

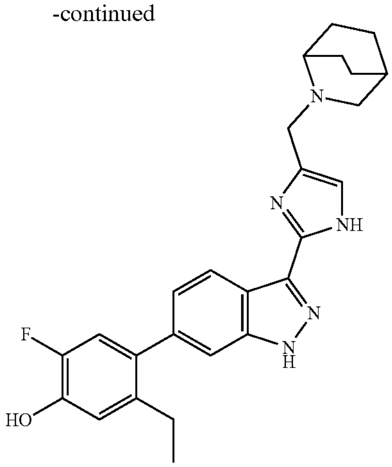

Ex-30

Synthesis Method

Synthesis of Intermediate 30-1: 2-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-2-azabicyclo[2.2.2]octane 2-(6-(2-ethyl-5-fluoro-4-((2-(trimethylsilyl)ethoxy)methoxy)phenyl)-1-((2-(trimethylsilyl)ethoxy)methyl)-1H-indol-3-yl)-1-(((2-(trimethylsilyl)ethoxy)methyl)-1H-imidazole-4-formaldehyde (55.0 mg, 0.08 mmol), 2-azabicyclo[2.2.2]octane (45.1 mg, 0.40 mmol), and 10 ml of 1,2-dichloroethane were added. The resulting mixture was stirred at room temperature for 2 h. Then sodium triacetylborohydride (53.6 mg, 0.24 mmol) was added. It was allowed to react at room temperature. After the reaction was completed, the reaction mixture was quenched with water and extracted with EA. The layers were separated. The resulting organic phase was washed with saturated sodium chloride solution and dried over anhydrous sodium sulfate. It was concentrated and separated by column chromatography to obtain 36 mg of colorless oil with a yield of 49.3%.

Synthesis of Compound Ex-30: 4-(3-(4-((2-azabicyclo[2.2.2]octan-2-yl)methyl)-1H-imidazol-2-yl)-1H-indazol-6-yl)-5-ethyl-2-fluorophenol Intermediate 30-1 (36 mg, 0.04 mmol), 6 ml of MeOH, and 3 ml of concentrated hydrochloric acid were added. It was allowed to react at 50° C. for 6 hours. The reaction mixture was concentrated, to which 4 ml of methanol and 0.5 ml of aqueous ammonia were added. The resulting mixture was concentrated and purified by a preparative silica gel plate to obtain 12 mg of white solid with a yield of 62.6%. LC-MS m/z (ESI) [M+H]+ calcd for $C_{26}H_{29}FN_5O_2$: 446.2; Found: 446.2.

Example 31: 4-(3-(4-((cyclobutylamino)methyl)-1H-imidazol-2-yl)-1H-indazol-6-yl)-5-ethyl-2-fluorophenol (Ex-31)

Ex-31

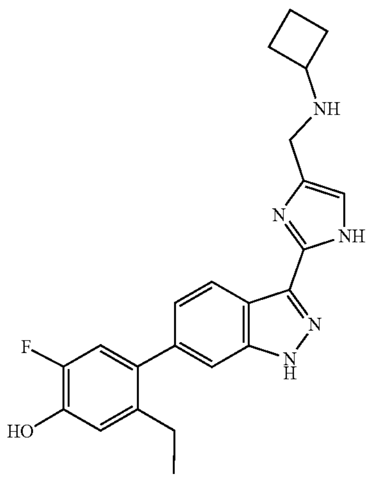

Synthetic Route of Ex-31

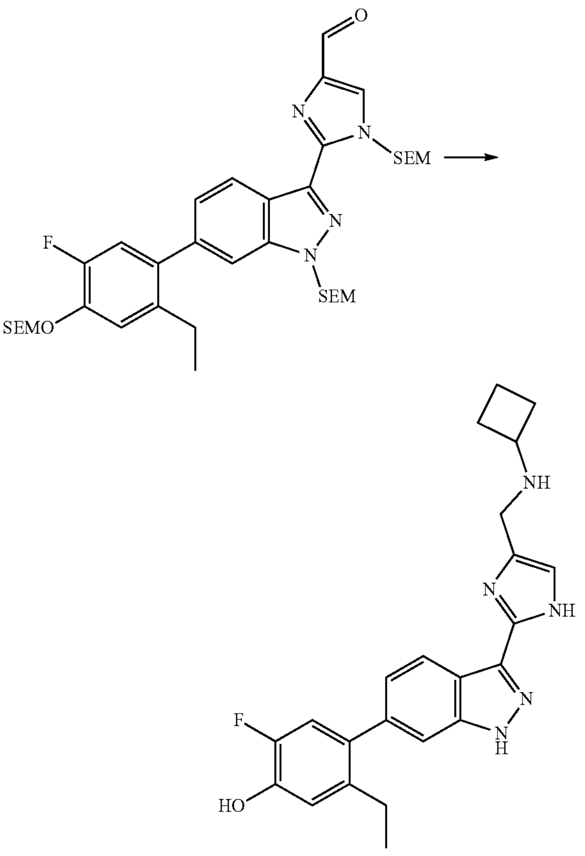

Ex-31

Synthesis Method

Synthesis of Compound Ex-31: 4-(3-(4-((cyclobutylamino)methyl)-1H-imidazol-2-yl)-1H-indazol-6-yl)-5-ethyl-2-fluorophenol 2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (20.0 mg, 0.03 mmol) and cyclobutylamine (3.1 mg, 0.04 mmol) were dissolved in DCM. It was allowed to react at room temperature for 0.5 h. To the reaction solution was added sodium triacetylborohydride (8.2 mg, 0.04 mmol). It was allowed to react at room temperature for 1.5 hour, to which water was added, and then the reaction solution was extracted twice with DCM. The resulting organic phases was combined, washed with saturated brine, and dried over anhydrous sodium sulfate. It was concentrated and purified. The obtained product was dissolved in 2 ml of methanol to which 1 ml of concentrated hydrochloric acid was added. It was allowed to react at 50° C. for 6 hours. The reaction mixture was concentrated and dissolved in 3 ml of methanol, to which 0.5 ml of aqueous ammonia was added, and then it was concentrated and purified by silica gel plate to obtain 5.2 mg of the final product with a yield of 49.0%.

$^1$H NMR (400 MHz, MeOD) δ 8.39 (d, J=8.0 Hz, 1H), 7.45 (s, 1H), 7.40 (s, 1H), 7.22-7.17 (m, 1H), 7.00-6.89 (m, 2H), 4.19 (s, 2H), 3.97-3.87 (m, 1H), 2.62-2.51 (m, 2H), 2.46-2.36 (m, 2H), 2.3-2.22 (m, 2H), 2.02-1.93 (m, 2H), 1.08 (t, J=8.0 Hz, 3H).

Example 32: 5-ethyl-2-fluoro-4-(3-(4-(((tetrahydrofuran-3-yl)amino)methyl)-1H-imidazol-2-yl)-1H-indazol-6-yl) phenol (Ex-32)

Ex-32

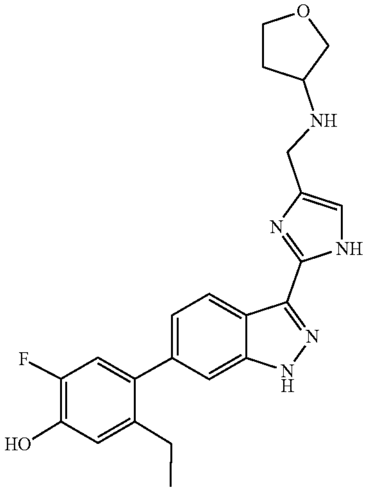

Synthetic Route of Ex-32

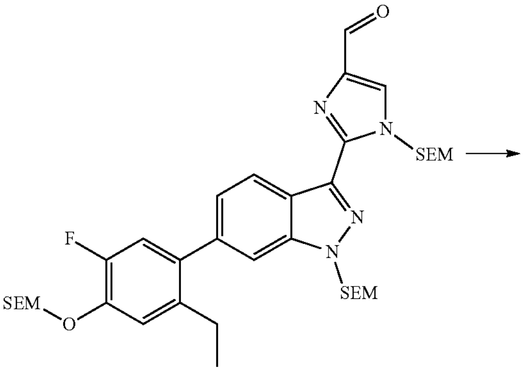

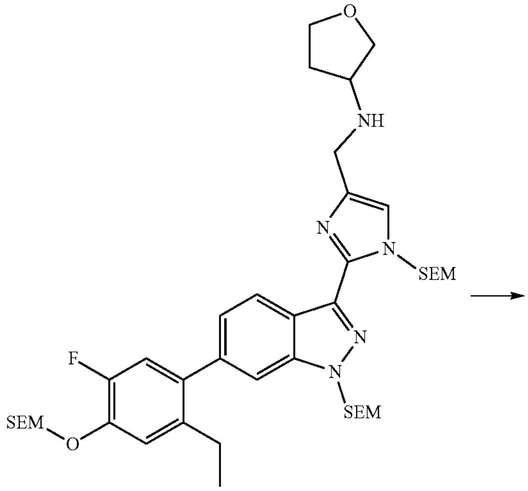

32-1

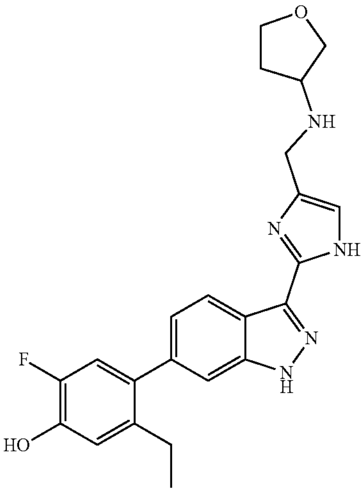

Ex.32

Synthesis Method

Synthesis of Intermediate 32-1: N-((2-(6-(2-ethyl-5-fluoro-4-((2-(trimethylsilyl)ethoxy)methoxy)phenyl)-1-((2-(Trimethylsilyl)ethoxy)methyl)-1H-indazol-3-yl)-1-((2-(trimethylsilyl)ethoxy)methyl)-1H-imidazol-4-yl)methyl) tetrahydrofuran-3-amine 2-(6-(2-ethyl-5-fluoro-4-((2-(trimethylsilyl)ethoxy) methoxy)phenyl)-1-((2-(trimethylsilyl)ethoxy)methyl)-1H-indazol-3-yl)-1-((2-(trimethylsilyl)ethoxy)methyl)-1H-imidazole-4-formaldehyde (20.0 mg, 0.03 mmol) was dissolved in 5 ml of anhydrous dichloromethane, to which tetrahydrofuran-3-amine (3.5 mg, 0.04 mmol) was added. It was allowed to react at room temperature for 30 minutes. And then sodium triacetylborohydride (8.6 mg, 0.04 mmol) was added. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified to obtain 15.0 mg of intermediate 32-1 with a yield of 68.4%.

Synthesis of Compound Ex-32: 5-ethyl-2-fluoro-4-(3-(4-(((tetrahydrofuran-3-yl)amino)methyl)-1H-imidazol-2-yl)-1H-indzazol-6-yl) phenol The intermediate 32-1 (15.0 mg, 0.02 mmol) was dissolved in 2 ml of methanol to which 1 ml of concentrated hydrochloric acid was added. It was allowed to react at 50° C. for 6 hours. The reaction mixture was concentrated and dissolved in 2 ml of methanol, to which 0.5 ml of aqueous ammonia was added, and then it was concentrated and purified by silica gel plate to obtain 4.3 mg of the final product with a yield of 55.1%.

$^1$H NMR (400 MHz, MeOD) δ 8.32 (dd, J=4.0 Hz, J=8.0 Hz, 1H), 7.43 (s, 1H), 7.20-7.17 (m, 2H), 6.95 (dd, J=12.0 Hz, J=20.0 Hz, 2H), 4.01-3.96 (m, 1H), 3.92 (d, J=4.0 Hz, 2H), 3.90-3.87 (m, 1H), 3.82-3.77 (m, 1H), 3.72-3.69 (m, 1H), 3.59-3.56 (m, 1H), 2.59-2.53 (m, 2H), 2.24-2.17 (m, 1H), 1.92-1.87 (m, 1H), 1.08 (t, J=8.0 Hz, 3H).

Example 33: 5-ethyl-2-fluoro-4-(3-(4-((pyridin-2-ylamino)methyl)-1H-imidazol-2-yl)-1H-indazol-6-yl)phenol (Ex-33)

Ex-33

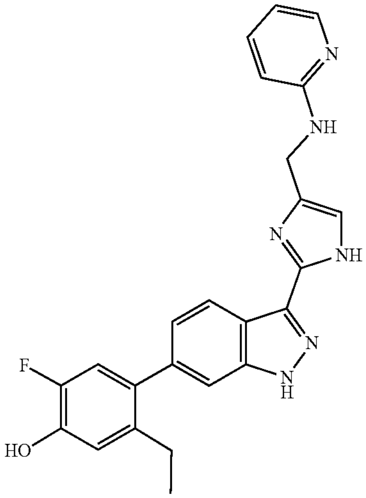

Synthetic Route of Ex-33

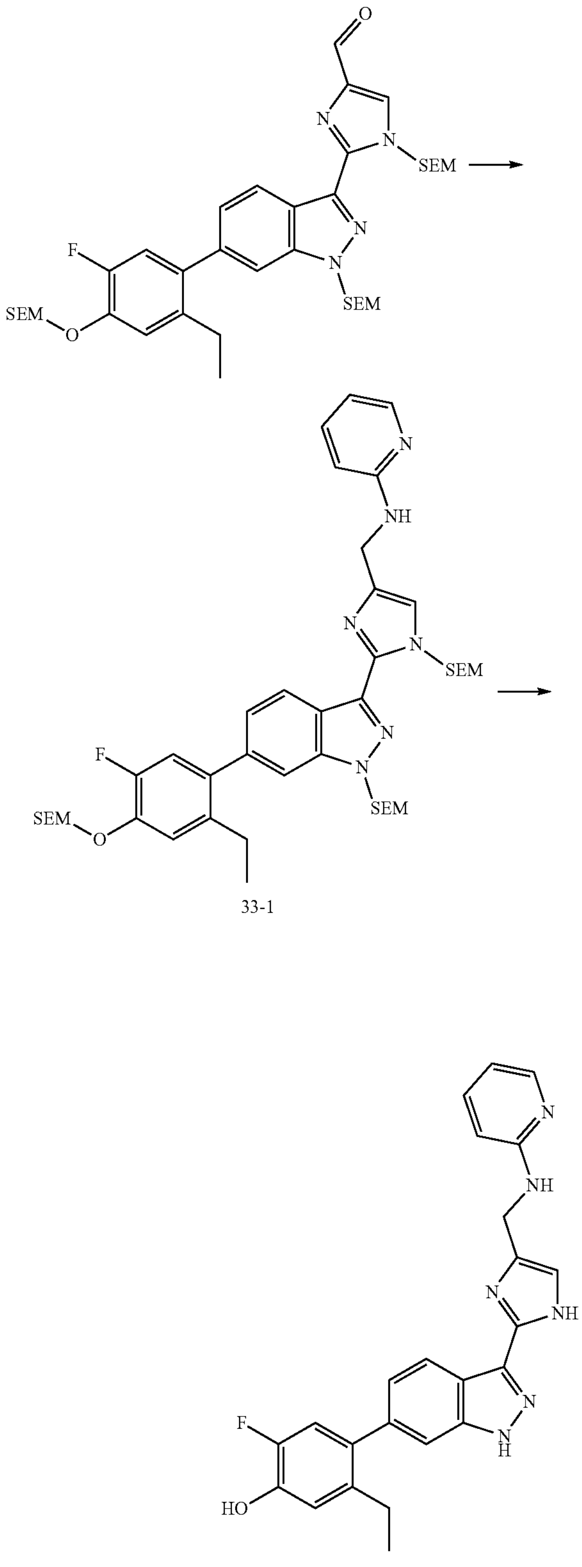

33-1

Ex.33

Synthesis Method

Synthesis of Intermediate 33-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)pyridin-2-amine The intermediate 2-(6-(2-ethyl-5-fluoro-4-((2-(trimethylsilyl)ethoxy) methoxy)phenyl)-1-((2-(trimethylsilyl)ethoxy) methyl)-1H-indol-3-yl)-1-(((2-(trimethylsilyl) ethoxy) methyl)-1H-imidazole-4-formaldehyde (30.0 mg, 0.04 mmol) and pyridin-2-amine (7.6 mg, 0.08 mmol) were dissolved in 3 ml of toluene. The resulting mixture was stirred at 100° C. for 20 hours. To the reaction mixture, sodium triacetylborohydride (17.0 mg, 0.08 mmol) was added. It was allowed to react at room temperature for 1 hour. The reaction mixture was quenched with water and extracted twice with DCM. The resulting organic phases was combined, and dried over anhydrous sodium sulfate. It was concentrated and purified to obtain 20.0 mg of intermediate 33-1 with a yield of 60.3%.

Synthesis of Compound Ex-33: 5-ethyl-2-fluoro-4-(3-(4-((pyridin-2-ylamino)methyl)-1H-imidazol-2-yl)-1H-indazol-6-yl)phenol The intermediate 33-1 (18.0 mg, 0.02 mmol) was dissolved in 2 ml of methanol to which 1 ml of concentrated hydrochloric acid was added. It was allowed to react at 50° C. for 6 hours. The reaction mixture was vacuum concentrated and dissolved in 3 ml of methanol, to which 0.5 ml of aqueous ammonia was added, and then it was concentrated and separated by silica gel plate to obtain 7 mg of the final product with a yield of 74.3%.

$^{1}$H NMR (400 MHz, MeOD) δ 8.30 (d, J=8.4 Hz, 1H), 8.07-7.91 (m, 1H), 7.50 (ddd, J=8.7 Hz, J=7.1 Hz, J=1.9 Hz, 1H), 7.42 (s, 1H), 7.24-7.10 (m, 2H), 7.01-6.85 (m, 2H), 6.74-6.55 (m, 2H), 4.57 (s, 2H), 2.55 (q, J=7.5 Hz, 2H), 1.07 (t, J=7.5 Hz, 3H).

Example 34: N-((2-(6-(2-ethyl-5-fluoro-4-hydroxyphenyl)-1H-indazol-3-yl)-1H-imidazol-4-yl)methyl)-1-methyl-1H-pyrazole-4-carboxamide (Ex-34)

Ex-34

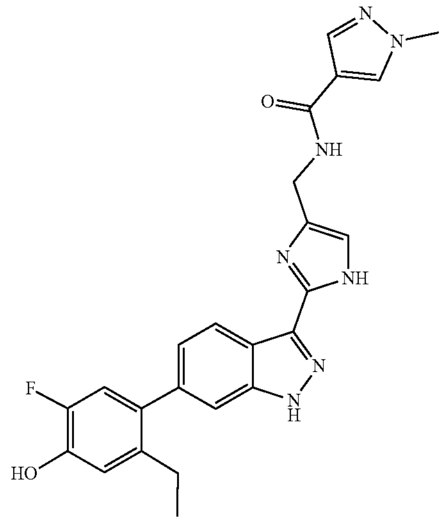

Synthetic Route of Ex-34

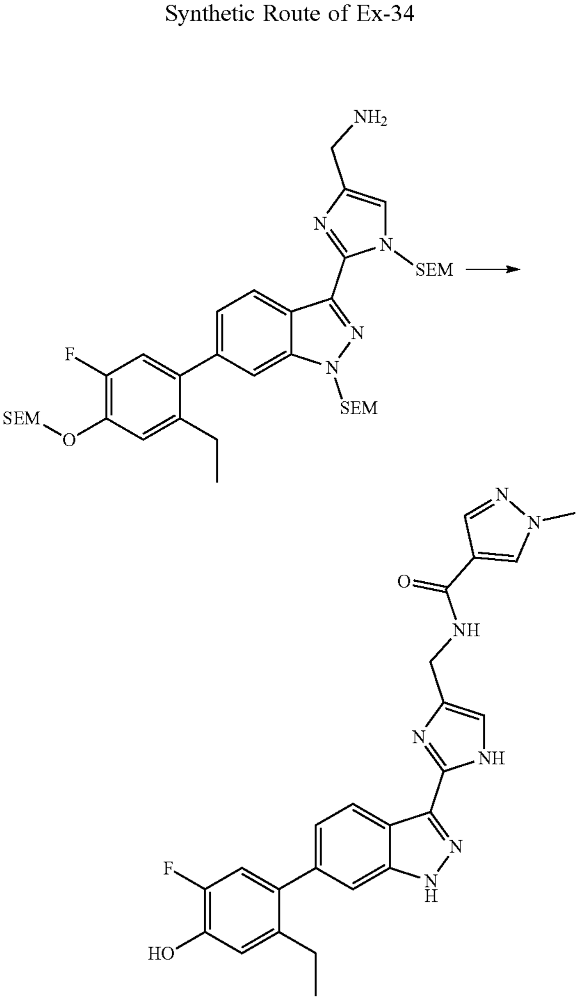

Ex-34

Synthesis Method

Synthesis of Compound Ex-34: N-((2-(6-(2-ethyl-5-fluoro-4-hydroxyphenyl)-1H-indazol-3-yl)-1H-imidazol-4-yl)methyl)-1-methyl-1H-pyrazole-4-carboxamide 1-methylpyrazole-4-carboxylic acid (7.4 mg, 0.06 mmol) was dissolved in 10 ml of DMF, to which HATU (22.4 mg, 0.06 mmol) and DIEA (12.7 mg, 0.10 mmol) were added. The resulting mixture was stirred at room temperature for 30 minutes. (2-(6-(2-ethyl-5-fluoro-4-((2-(trimethylsilyl) ethoxy)methoxy)phenyl)-1-((2-(trimethylsilyl)ethoxy) methyl)-1H-indazol-3-yl)-1-((2-(trimethylsilyl)ethoxy) methyl)-1H-imidazol-4-yl) methylamine (30.0 mg, 0.04 mmol) was added. It was allowed to react at room temperature for 2 hours. The reaction mixture was quenched with water and extracted twice with ethyl acetate. The resulting organic phases were combined, washed with saturated brine, dried over anhydrous sodium sulfate and concentrated to obtain the crude product. The resulting produce was dissolved in 4 ml of methanol, to which 2 ml of concentrated hydrochloric acid was added. It was allowed to react at 50° C. for 6 hours. The reaction mixture was concentrated and dissolved in 2 ml of methanol, to which 0.5 ml of aqueous ammonia was added. It was concentrated and purified by a preparative silica gel plate to obtain 8.0 mg of the final product with a yield of 43.1%.

$^1$H NMR (400 MHz, MeOD) δ 8.29 (d, J=8.3 Hz, 1H), 8.10 (s, 1H), 7.94 (s, 1H), 7.42 (s, 1H), 7.17 (dd, J=1.4 Hz, J=8.3 Hz, 1H), 7.16 (s, 1H), 6.93 (dd, J=11.7 Hz, J=21.7 Hz, 2H), 4.61 (s, 2H), 3.94 (s, 3H), 2.55 (q, J=7.6 Hz, 2H), 1.08 (t, J=7.6 Hz, 3H).

Example 35: 5-ethyl-2-fluoro-4-(3-(4-(((1-methylpyrrolidin-3-yl)amino)methyl)-1H-imidazol-2-yl)-1H-indazol-6-yl)phenol (Ex-35)

Ex-35

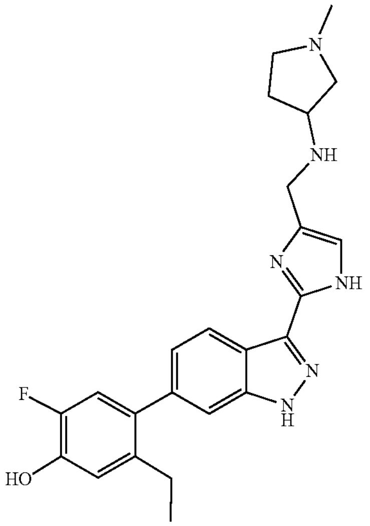

Synthetic Route of Ex-35

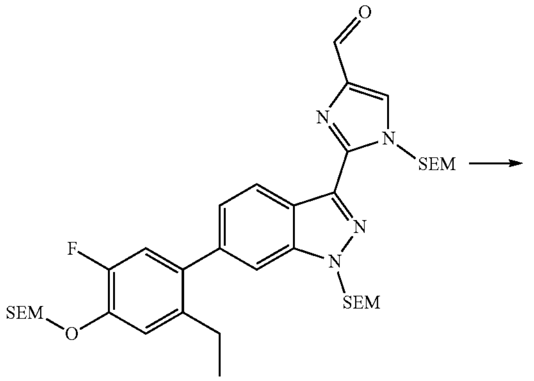

-continued

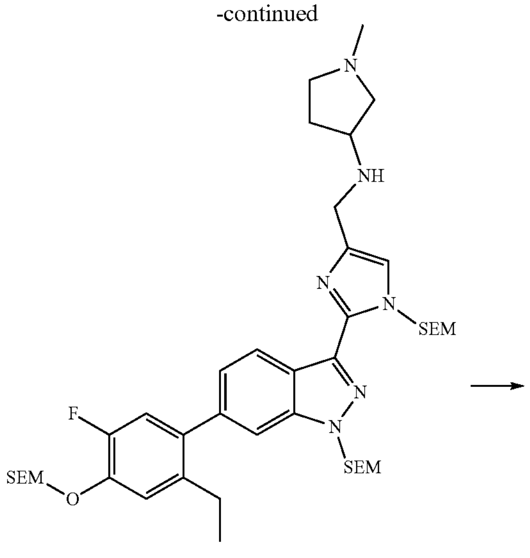

35-1

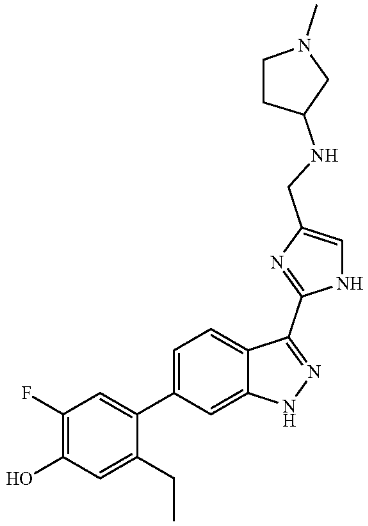

Ex.35

Synthesis Method

Synthesis of Intermediate 35-1: N-((2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methyl)-1-methyl pyrrolidin-3-amine 2-(6-(2-ethyl-5-fluoro-4-((2-(trimethylsilyl)ethoxy)methoxy)phenyl)-1-((2-(trimethylsilyl)ethoxy)methyl)-1H-indol-3-yl)-1-(((2-(trimethylsilyl) ethoxy)methyl)-1H-imidazole-4-formaldehyde (25.0 mg, 0.03 mmol) was dissolved in 3 ml of anhydrous dichloromethane, to which 1-methylpyrrolidin-3-amine (5.1 mg, 0.05 mmol) was added. The resulting mixture was stirred at room temperature for 30 minutes. To the reaction mixture, sodium triacetylborohydride (10.7 mg, 0.05 mmol) was added. It was allowed to react at room temperature for 1 hour. The reaction mixture was quenched with water and extracted twice with DCM. The resulting organic phases was combined, washed with saturated saline and dried over anhydrous sodium sulfate. It was concentrated and purified to obtain 17.2 mg of intermediate 35-1 with a yield of 61.8%.

Synthesis of Compound Ex-35: 5-ethyl-2-fluoro-4-(3-(4-(((1-methylpyrrolidin-3-yl)amino)methyl)-1H-imidazol-2-yl)-1H-indazol-6-yl)phenol The intermediate 35-1 (17.2 mg, 0.02 mmol) was dissolved in 2 ml of methanol to which 1 ml of concentrated hydrochloric acid was added. It was allowed to react at 50° C. for 6 hours. The reaction mixture was concentrated and dissolved in 3 ml of methanol, to which 0.5 ml of aqueous ammonia was added, and then it was concentrated and purified by a preparative silica gel plate to obtain 3.4 mg of the final product with a yield of 37.6%.

$^1$H NMR (400 MHz, MeOD) δ 8.36 (d, J=8.0 Hz, 1H), 7.46 (dd, J=4.0 Hz, J=8.0 Hz, 2H), 7.22-7.20 (m, 1H), 6.95 (dd, J=12.0 Hz, J=20.0 Hz, 2H), 4.22 (s, 2H), 4.10-4.04 (m, 1H), 3.67-3.54 (m, 3H), 3.37-3.33 (m, 1H), 2.96 (s, 3H), 2.61-2.52 (m, 3H), 2.32-2.21 (m, 1H), 1.08 (t, J=8.0 Hz, 3H).

Example 36: N-((2-(6-(2-ethyl-5-fluoro-4-hydroxyphenyl)-1H-indazol-3-yl)-1H-imidazol-4-yl)methyl)morpholine-4-carboxamide (Ex-36)

Ex-36

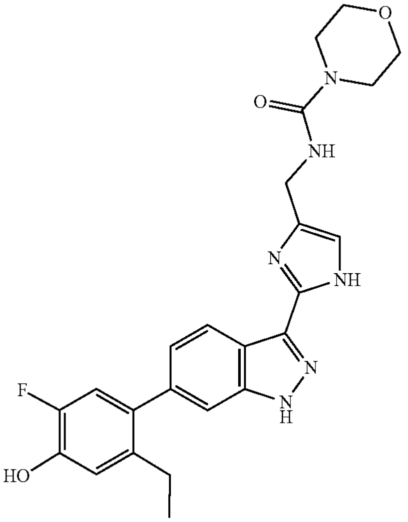

Synthetic Route of Ex-36

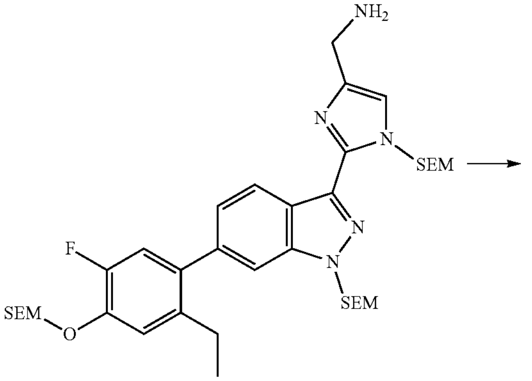

-continued

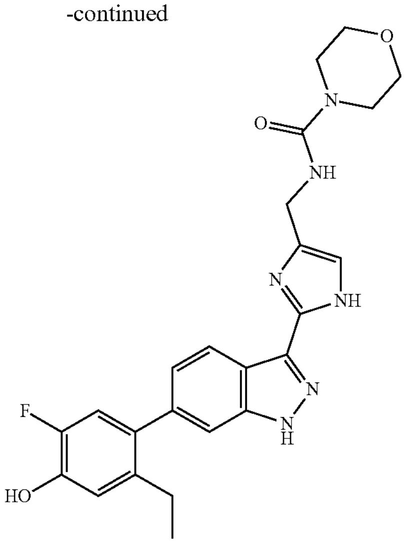

Ex-36

Synthesis Method

Synthesis of Compound Ex-36: N-((2-(6-(2-ethyl-5-fluoro-4-hydroxyphenyl)-1H-indazol-3-yl)-1H-imidazol-4-yl)methyl)morpholine-4-carboxamide Triphosgene (11 mg, 0.04 mmol) was dissolved in DCM and cooled to 0° C. To the solution, (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (25.0 mg, 0.03 mmol) in DCM was dropwise added. It was allowed to react for 5 minutes. To the reaction mixture, triethylamine (10.2 mg, 0.10 mmol) was dropwise add slowly. It was allowed to react at 0° C. for 0.5 hours. To the reaction mixture, morpholine (4.4 mg, 0.05 mmol) was added. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified on silica gel plate. The obtained product was dissolved in 2 ml of methanol and 1 ml of concentrated hydrochloric acid. It was allowed to react at 50° C. for 6 hours. The reaction mixture was concentrated and dissolved in 3 ml of methanol, to which 0.5 ml of aqueous ammonia was added, and then it was concentrated and purified by a preparative plate to obtain 5 mg of the final product with a yield of 32.0%.

$^1$H NMR (400 MHz, MeOD) δ 8.28 (d, J=8.0 Hz, 1H), 7.43 (s, 1H), 7.18 (d, J=8.0 Hz, 1H), 7.10 (s, 1H), 6.90-6.97 (m, 2H), 4.45 (s, 2H), 3.68 (t, J=4.0 Hz, 4H), 3.43 (t, J=4.0 Hz, 4H), 2.53-2.58 (m, 2H), 1.08 (t, J=8.0 Hz, 3H).

Example 37: N-((2-(6-(2-ethyl-5-fluoro-4-hydroxyphenyl)-1H-indazol-3-yl)-1H-imidazol-4-yl)methyl)-4-methylpiperazine-1-carboxamide (Ex-37)

Ex-37

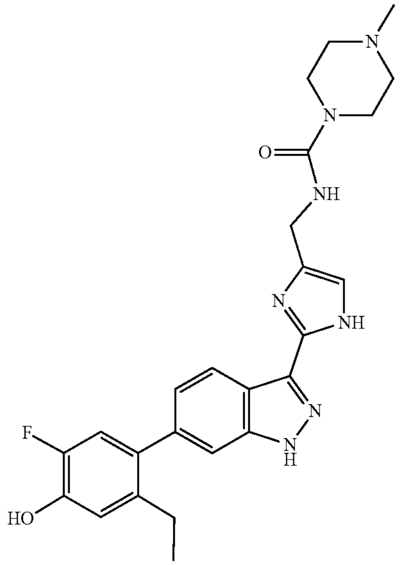

Synthetic Route of Ex-37

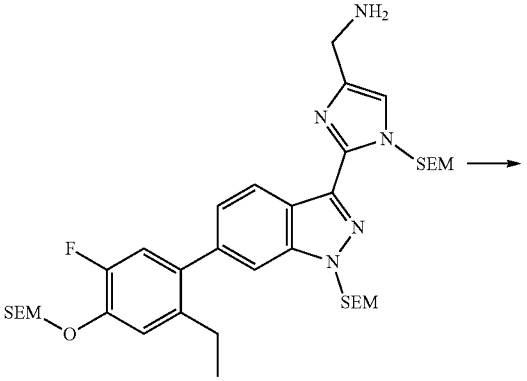

-continued

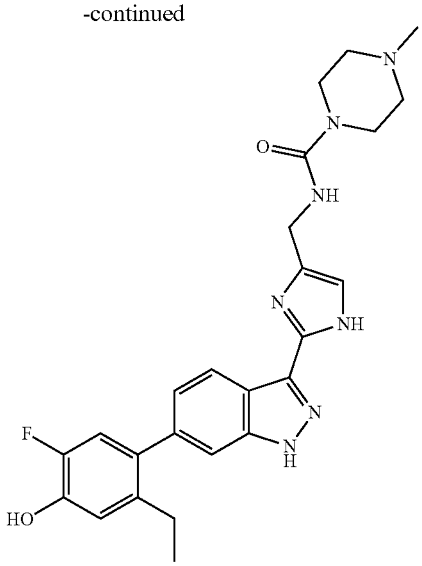

Ex-37

Synthesis Method

Synthesis of Compound Ex-37: N-((2-(6-(2-ethyl-5-fluoro-4-hydroxyphenyl)-1H-indazol-3-yl)-1H-imidazol-4-yl)methyl)-4-methylpiperazine-1-carboxamide Triphosgene (11 mg, 0.04 mmol) was dissolved in DCM and cooled to 0° C. To the solution, (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-1H-imidazol-4-yl)methanamine (25.0 mg, 0.03 mmol) in DCM was dropwise added. It was allowed to react for 5 minutes. To the reaction mixture, triethylamine (10.2 mg, 0.10 mmol) was dropwise add slowly. It was allowed to react at 0° C. for 0.5 hours. To the reaction mixture, 1-methylpiperazine (5.1 mg, 0.05 mmol) was added. It was allowed to react at room temperature for 1 hour, to which water was added, and then the reaction solution was extracted twice with DCM. The resulting organic phases was combined, washed with saturated brine, and dried over anhydrous sodium sulfate. It was concentrated and purified. The obtained product was dissolved in 2 ml of methanol and 1 ml of concentrated hydrochloric acid. It was allowed to react at 50° C. for 6 hours. The reaction mixture was concentrated and dissolved in 3 ml of methanol, to which 0.5 ml of aqueous ammonia was added, and then it was concentrated and purified by a preparative plate to obtain 6 mg of the final product with a yield of 37.3%.

$^1$H NMR (400 MHz, MeOD) δ 8.27 (d, J=8.0 Hz, 1H), 7.45 (s, 1H), 7.19 (d, J=8.0 Hz, 1H), 7.16 (s, 1H), 6.90-6.97 (m, 2H), 4.46 (s, 2H), 3.67-3.74 (m, 4H), 3.10-3.15 (m, 4H), 2.80 (s, 3H), 2.53-2.58 (m, 2H), 1.08 (t, J=8.0 Hz, 3H).

Example 38: 5-ethyl-4-(3-(4-((4-ethylpiperazin-1-yl)methyl)-1H-imidazol-2-yl)-1H-indazol-6-yl)-2-fluorophenol (Ex-38)

Ex-38

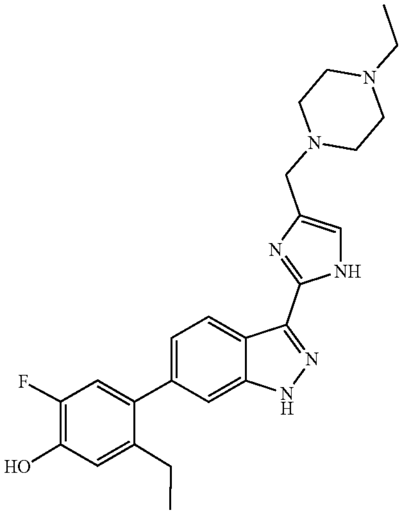

Synthetic Route of Ex-38

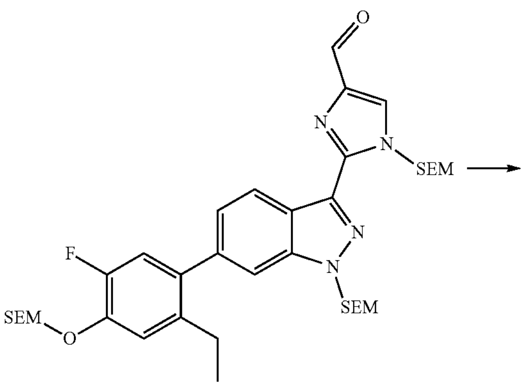

-continued

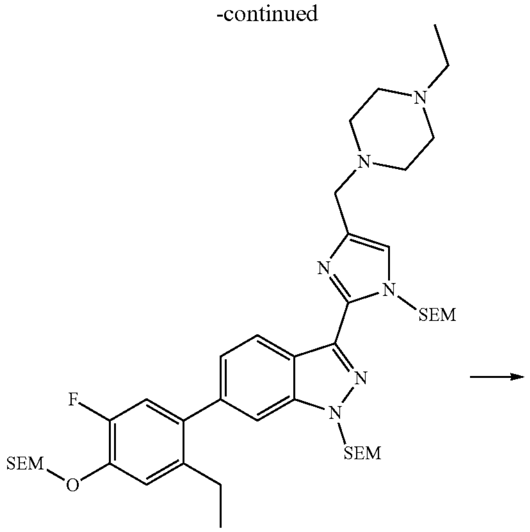

38-1

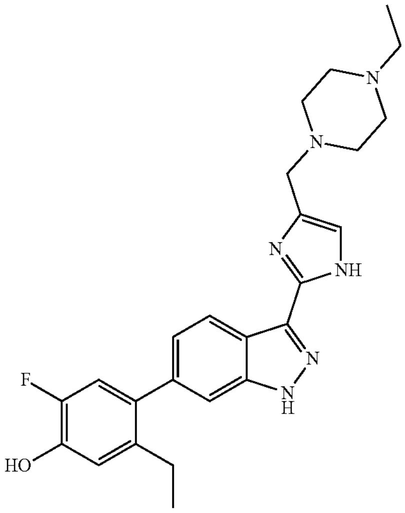

Ex-38

Synthesis Method

Synthesis of Intermediate 38-1: (6-(2-ethyl-5-fluoro-4-((2-(trimethylsilyl)ethoxy)methoxy)phenyl)-3-(4-((4-ethylpiperazin-1-yl)methyl)-1-((2-(trimethylsilyl)ethoxy)methyl)-1H-imidazol-2-yl)-1-((2-(trimethylsilyl)ethoxy)methyl)-1H-indazole 2-(6-(2-ethyl-5-fluoro-4-((2-(trimethylsilyl)ethoxy)methoxy)phenyl)-1-((2-(trimethylsilyl)ethoxy)methyl)-1H-indol-3-yl)-1-(((2-(trimethylsilyl) ethoxy)methyl)-1H-imidazole-4-formaldehyde (25.0 mg, 0.03 mmol) was dissolved in 5 ml of anhydrous dichloromethane, to which 1-ethylpiperazine (5.8 mg, 0.05 mmol) was added. It was allowed to react at room temperature for 30 minutes. To the reaction mixture, sodium triacetylborohydride (10.7 mg, 0.05 mmol) was added. It was allowed to react at room temperature for 1 hour. The reaction mixture was quenched with water and extracted twice with DCM. The resulting organic phases was combined, washed with saturated saline and dried over anhydrous sodium sulfate. It was concentrated and purified to obtain 23.0 mg of intermediate 32-1 with a yield of 81.3%.

Synthesis of Compound Ex-38: 5-ethyl-4-(3-(4-((4-ethylpiperazin-1-yl)methyl)-1H-imidazol-2-yl)-1H-indazol-6-yl)-2-fluorophenol Intermediate 38-1 (23.0 mg, 0.02 mmol) was dissolved in 2 mol of methanol, to which 1 ml of concentrated hydrochloric acid was added. It was allowed to react at 50° C. for 6 hours. The reaction mixture was concentrated, and dissolved in 2 ml of methanol to which 0.5 ml of aqueous ammonia was added. The resulting mixture was concentrated and purified by a preparative silica gel plate to obtain 6.7 mg of final product with a yield of 54.5%. LC-MS m/z (ESI) [M+H]+ calcd for $C_{25}H_{30}FN_6O$: 449.2; Found: 449.2.

Assay: Evaluation of Pharmacological Activity

1. Experimental Principle

A drug screening system based on kinases JAK1, JAK2, JAK3, and TYK2 was used to detect the inhibitory ability of small molecule compounds on kinase activity. A kinase undergoes an enzymatic reaction with its substrates IRS 1, IGF1Rtide, and Poly (4:1 Glu, Tyr), consuming ATP to produce ADP, wherein the ADP-Glo reagent and luminescence method were used to detect the amount of the product to reflect the activity of the kinase. 2.1 Experimental Materials and Instruments

| No. | Name | Source/Supplier | Catalogue No. |
|---|---|---|---|
| 1 | HEPES | Life Technologies | 15630-080 |
| 2 | BRIJ 35 detergent (10%) | Sigma | 1018940100 |
| 3 | MgCl2 | Sigma | M1028 |
| 4 | EGTA | Sigma | E3889 |
| 5 | ADP-Glo Kinase Assay | Promega | V9101 |
| 6 | JAK1 | Carna | 08-144 |
| 7 | JAK2 | Carna | 08-045 |
| 8 | JAK3 | Carna | 08-046 |
| 9 | TYK2 | Carna | 08-147 |
| 10 | ATP | Promega | V915B |
| 11 | IRS1 | Signalchem | I40-58-1000 |
| 12 | IGFIRtide | Signalchem | I15-58 |
| 13 | Poly (4:1 Glu, Tyr) | Sigma | P0275 |
| 15 | 384-Well polystyrene shallow flat white | Greiner | 784075 |
| 16 | 384-Well Polypropylene microplate | Labeyte | PP-0200 |
| 17 | Biotek Microplate Reader | Biotek | Synergy 4 |
| 18 | Microplate Low Speed Centrifuge | XiangZhi | TD5B |

2.2 Experimental Methods 2.2.1 Kinase Reaction Reagent Formulation 2.2.1.1 1× Kinase Reaction Buffer (400 ML)

| Name | Stock Concentration | Volume | Final Concentration |
|---|---|---|---|
| HEPES | 1M (20X) | 20 mL | 50 mM |
| $MgCl_2$ | 1M (100X) | 4 mL | 10 mM |
| BRIJ-35 | 10% (1000X) | 400 μL | 0.01% |
| EGTA | Powder | 152 mg | 1 mM |
| ddH2O | | 375.6 mL | |

2 mM DTT, ready to use 2.2.1.2 2× Kinase Formulation

| Name | Stock concentration | Volume | 2X Final Concentration | Final Concentration |
|---|---|---|---|---|
| JAK1 kinase solution | | | | |
| JAK1 | 3225 nM (884X) | 5.21 μL | 40 nM | 20 nM |
| 1X Kinase Reaction Buffer | | 414.79 μL | | |
| JAK2 kinase solution | | | | |
| JAK2 | 4256 nM (4955X) | 0.2 μL | 2 nM | 1 nM |
| 1X Kinase Reaction Buffer | | 419.8 μL | | |

| Name | Stock concentration | Volume | 2X Final Concentration | Final Concentration |
|---|---|---|---|---|
| JAK3 kinase solution | | | | |
| JAK3 | 3195 nM (5341.2X) | 0.5 μL | 4 nM | 2 nM |
| 1X Kinase Reaction Buffer | | 419.5 μL | | |
| TYK2 kinase solution | | | | |
| TYK2 | 3174 nM (763X) | 2.65 μL | 20 nM | 10 nM |
| 1X Kinase Reaction Buffer | | 417.35 μL | | |

2.2.1.3 4× Substrate Mixture Formulation

| Name | Stock concentration | Volume | 4X Final Concentration | Final Concentration |
|---|---|---|---|---|
| JAK1 substrate mixture solution | | | | |
| ATP | 10 mM (125X) | 2.4 μL | 80 μM | 30 μM |
| IRS1 | 1 mg/mL (5X) | 60 μL | 0.2 mg/mL | 0.05 mg/mL |
| 1X Kinase Reaction Buffer | | 237.6 μL | | |
| JAK2 substrate mixture solution | | | | |
| ATP | 10 mM (500X) | 6 μL | 20 μM | 5 μM |
| IGF1Rtide | 1 mg/mL (25X) | 12 μL | 0.04 mg/mL | 0.01 mg/mL |
| 1X Kinase Reaction Buffer | | 287.4 μL | | |
| JAK3 substrate mixture solution | | | | |
| ATP | 10 mM (250X) | 1.2 μL | 40 μM | 10 μM |
| Poly (4:1 Glu, Tyr) Peptide | 5 mg/mL (41.6X) | 6 μL | 0.12 mg/mL | 0.03 mg/mL |
| 1X Kinase Reaction Buffer | | 292.8 μL | | |

-continued

| Name | Stock concentration | Volume | 4X Final Concentration | Final Concentration |
|---|---|---|---|---|
| | | TYK2 substrate mixture solution | | |
| ATP | 10 mM (250X) | 1.2 μL | 40 μM | 10 μM |
| IRS1 | 1 mg/mL (5X) | 60 μL | 0.08 mg/mL | 0.02 mg/mL |
| 1X Kinase Reaction Buffer | | 238.8 μL | | |

2.2.2 Kinase Reaction Experiment Procedure a) Dilute a compound solution to be tested by 5 times with 100% DMSO. Then, using 100% DMSO as diluent, perform a series of dilutions at a ratio of 1:3 for Filgotinib (10 mM stock solution) and the compound solution to be tested in a 96-well dilution plate. Take out 1 μL of the compound solution and add it to 49 μL of kinase reaction buffer, and shake the resulting mixture on a microplate shaker for 20 minutes.

b) Transfer 2 μL of kinase (prepared according to 2.2.1.2) to a 384-well reaction plate, add 1 μL of the compound solution to be tested (prepared in step a) to the 384-well reaction plate (Greiner, 784075), centrifuge it at 1000 rpm/min for 1 min and incubate it at 25° C. for 10 min.

c) Transfer 1 μL of the substrate mixture (prepared according to 2.2.1.3) to the 384-well reaction plate, centrifuge it at 1000 rpm/min for 1 min, and incubate it at 25° C. for 60 min. In the reaction system, the final concentrations of Filgotinib are 50, 12.5, 3.125, 0.7812, 0.1953, 0.0488, 0.0122, 0.003, 0.00076, 0.00019, and 0.000047 μM. The final concentrations of the compound to be tested are: 10, 2.5, 0.625, 0.15625, 0.039, 0.0097, 0.0024, 0.0006, 0.0015, 0.000038, and 0.0000095 μM. The final concentration of DMSO is 0.5%.

d) Transfer 4 μL of ADP-Glo to the 384-well reaction plate, centrifuge it at 1000 rpm/min for 1 min, and incubate it at 25° C. for 40 min.

e) Transfer 8 μL of Detection solution to the 384-well reaction plate, centrifuge it at 1000 rpm/min for 1 min, and incubate it at 25° C. for 40 min.

f) Use Biotek multi-function plate reader to read the RLU (Relative luminescence unit) signal. The signal intensity is used to characterize the degree of kinase activity.

2.2.3 Experimental Data Processing Method

Compound inhibition rate (% inh)=(negative control−compound)/(negative control−positive control)*100%

Negative control: DMSO

Positive control: 10 μM/50 μM Filgotinib

IC50 (half inhibitory concentration) of the compound can be obtained using the following nonlinear fitting formula:

$$Y=\text{Bottom}+(\text{Top}-\text{Bottom})/(1+10\hat{}((\text{Log IC50}-X)*\text{HillSlope}))$$

X: log value of the compound concentration

Y: Compound inhibition rate (% inh)

Z' Factor Calculation Equation:

$$Z'=1-3(\text{SDmin}+\text{SDmax})/(\text{AVEmax}-\text{AVEmin})$$

in which:

Min is the RLU value of the positive control 10 μM/50 μM Filgotinib, and Max is the RLU value of the negative control DMSO; and SD is the standard error, and AVE is the average value of RLU.

3. Experimental Results 3.1 Quality Control Results of Compound Test 3.1.1 Quality Control Result of JAK1 Binding Experiment Z'=0.79CV % (min)=4% CV % (max)=5%

3.1.2 Quality Control Result of JAK2 Binding Experiment

Z'=0.74CV % (min)=9% CV % (max)=8%

3.1.3 Quality Control Result of JAK3 Binding Experiment

Z'=0.76CV % (min)=15% CV % (max)=6%

3.1.4 Quality Control Result of TYK2 Binding Experiment

Z'=0.84CV % (Min)=8% CV % (Max)=4%

3. Experimental Results

| Compound | IC50(nM) | | | |
|---|---|---|---|---|
| ID | JAK1 | JAK2 | JAK3 | TYK2 |
| Filgotinib | 42.3 | 44.8 | 1473 | 293 |
| MDI-3 | 1.96 | 1.35 | 1.41 | 32.2 |
| MDI-301 | 0.317 | 0.466 | 1.13 | 6.82 |
| MDI-302 | 0.359 | 0.420 | 0.812 | 12.9 |
| MDI-303 | 0.430 | 0.641 | 1.34 | 6.26 |
| MDI-304 | 0.172 | 1.32 | 0.912 | 8.26 |
| MDI-305 | 3.18 | 1.49 | 2.20 | 63.8 |
| MDI-306 | 0.104 | 0.428 | 0.600 | 9.07 |
| Ex-9 | 1.3 | 1.5 | 1.3 | 19.8 |
| Ex-10 | 1.2 | 5.2 | 4.5 | 27 |
| Ex-11 | 0.31 | 0.85 | 2.5 | 18.4 |
| Ex-12 | 0.1 | 0.74 | 0.67 | 6.1 |
| Ex-13 | 0.48 | 0.84 | 1.7 | 11.3 |
| Ex-14 | 0.47 | 1.2 | 1.6 | 9.6 |
| Ex-15 | 0.29 | 0.78 | 0.76 | 4.9 |
| Ex-16 | 0.16 | 0.5 | 0.43 | 0.97 |
| Ex-17 | 0.36 | 1.2 | 2.9 | 6.5 |
| Ex-18 | 0.15 | 1.4 | 1.1 | 3.7 |
| Ex-19 | 0.33 | 3.3 | 2.3 | 6.4 |
| Ex-20 | 0.1 | 0.53 | 0.43 | 1.0 |
| Ex-21 | 0.21 | 0.72 | 0.64 | 6.9 |
| Ex-22 | 0.14 | 0.68 | 0.48 | 1.1 |
| Ex-23 | 0.15 | 0.68 | 0.49 | 0.96 |
| Ex-24 | 0.37 | 1.3 | 3.3 | 23 |
| Ex-25 | 0.4 | 2.8 | 2.5 | 7.0 |
| Ex-26 | 0.43 | 0.43 | 0.57 | 1.7 |
| Ex-27 | 0.92 | 6.3 | 4.4 | 9.2 |
| Ex-28 | 0.14 | 0.86 | 1.0 | 1.6 |
| Ex-29 | 1.1 | 13.3 | 9.3 | 16.8 |
| Ex-30 | 0.52 | 1.8 | 4.5 | 30 |
| Ex-31 | 0.1 | 1.6 | 3.7 | 17.3 |
| Ex-32 | 0.27 | 0.89 | 1.9 | 11.6 |
| Ex-33 | 0.58 | 1.4 | 1.7 | 13.3 |
| Ex-34 | 0.15 | 1.0 | 0.5 | 1.1 |
| Ex-35 | 0.32 | 0.63 | 0.85 | 5.2 |
| Ex-36 | 0.11 | 0.55 | 0.48 | 0.83 |
| Ex-37 | 0.1 | 0.66 | 0.55 | 1.9 |
| Ex-38 | 0.1 | 1.2 | 2.1 | 11 |

The above experimental results show that all compounds of the present disclosure tested in assay can inhibit JAK1, JAK2, JAK3, and TYK3 at very low concentrations and the inhibitory activities of these compounds are much higher than that of Filgotinib.

Although specific embodiments of the present disclosure have been illustrated and described, it does not mean that these embodiments illustrate and describe all possible implementation forms of the present disclosure. More precisely, the language used in this specification are only descriptive words and not restrictive. It will be obvious to those skilled in the art that various kinds of changes and modifications can be made without departing from the general scope of the present disclosure. Therefore, the appended claims are intended to include all these changes and modifications within the scope of the present disclosure.

What is claimed is:

1. A compound of Formula (I) as a JAK inhibitor

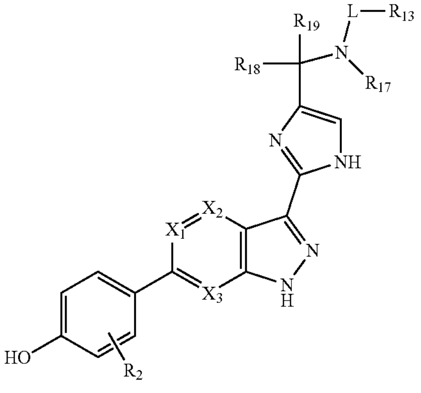

or an isotopically labeled compound thereof, or an optical isomer thereof, a tautomer thereof, or a pharmaceutically acceptable salt thereof, wherein L is C═O, O═S═O, $CH_2$ or a bond; and $X_1$ is CH; and $X_2$ is CH; and $X_3$ is CH; and $R_{13}$ is H, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclic, $C_{5-11}$ bicycloalkyl, 5-11 membered bicyclic heteroalkyl, and $R_{13}$ is substituted with 0, 1, 2, 3, or 4 $R_1$(s); and $R_{17}$ is selected from the group consisting of H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, —C(═O)—N($R_9$)($R_{10}$), —C(═O)—$R_{12}$, —C(═O)—O$R_{12}$, and —S(═O)$_2$—N($R_9$)($R_{10}$), in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; or $R_{13}$ and $R_{17}$ form a 4-10 membered heterocycloalkyl with Land N atoms to which they are attached together, and the 4-10 membered heterocycloalkyl is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; and $R_{18}$ and $R_{19}$ are each independently selected from the group consisting of H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl-, (5-10-membered heteroaryl)-$C_{1-4}$ alkyl-, in which each option in the group is optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; or $R_{18}$ and $R_{19}$ form $C_{3-10}$ cycloalkyl or a 4-10 membered heterocycloalkyl with carbon atom to which they are attached together, and the $C_{3-10}$ cycloalkyl and 4-10 membered heterocycloalkyl are optionally substituted with 1, 2, 3 or 4 substitutes each independently selected from halogen, —$CF_3$, —OH, —$NH_2$, —NH($CH_3$), —N($CH_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, —N($C_{1-4}$ alkyl)(C(═O)$C_{1-4}$ alkyl), $C_{1-4}$ haloalkyl, $C_{1-4}$ alkoxy and $C_{1-4}$haloalkoxy; and 0, 1, 2, 3 or 4 $R_2$(s) are present in formula (I), and each $R_2$ is independently selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, —N($R_9$)($R_{10}$), —N($R_{11}$)(C(═O)$R_{12}$), —C(═O)—N($R_9$)($R_{10}$), —C(═O)—$R_{12}$, —C(═O)—O$R_{12}$, —OC(═O)$R_{12}$, —N($R_{11}$)(S(═O)$_2$$R_{12}$), —S(═O)$_2$—N($R_9$)($R_{10}$), —S$R_{12}$ and —O$R_{12}$, in which the —S—$C_{1-4}$ alkyl, $C_{1-6}$ alkyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—O$R_{12}$, —C(═O)H, —C(═O)$R_{12}$, —C(═O)—N($R_9$)($R_{10}$), —N($R_{11}$)(S(═O)$_2$$R_{12}$), —S(═O)$_2$—N($R_9$)($R_{10}$), —S$R_{12}$ and —O$R_{12}$; and each $R_1$ is independently selected from H, halogen, —OH, —$NO_2$, —CN, —$SF_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclic, $C_{5-11}$bicycloalkyl, 5-11 membered bicyclic heteroalkyl, —$N(R_9)(R_{10})$, —$N(R_{11})(C(=O)$ $R_{12})$, —C(=O)—$N(R_9)(R_{10})$, —C(=O)—$R_{12}$, —C(=O)—$OR_{12}$, —OC(=O)$R_{12}$, —$N(R_{11})(S(=O)_2R_{12})$, —$S(=O)_2$—$N(R_9)(R_{10})$, —$SR_{12}$ and —$OR_{12}$, in which the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4$(s); and $R_3$ and $R_4$ are each independently selected from H, halogen, —OH, —$NO_2$, —CN, —$SF_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, —$N(R_5)(R_6)$, —$N(R_{11})(C(=O)R_{12})$, —$CON(R_7)(R_8)$, —C(=O)—$R_{12}$, —C(=O)—$OR_{12}$, —OC(=O)$R_{12}$, —$N(R_{11})(S(=O)_2R_{12})$, —$S(=O)_2$—$N(R_9)(R_{10})$, —$SR_{12}$ and —$OR_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, or 3 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —$N(R_9)(R_{10})$, —$N(R_{11})(C(=O)R_{12})$, —C(=O)—$OR_{12}$, —C(=O)H, —C(=O)$R_{12}$, —C(=O)—$N(R_9)(R_{10})$, —$N(R_{11})(S(=O)_2R_{12})$, —$S(=O)_2$—$N(R_9)(R_{10})$, —$SR_{12}$ and —$OR_{12}$; and $R_5$, $R_6$, $R_7$, $R_8$, $R_9$, $R_{10}$, $R_{11}$, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein the substituents included in the above group are each optionally substituted with 1, 2, 3 or 4 substituent(s) each independently selected from the group consisting of halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}$ alkyl$)_2$, $C_{1-4}$ haloalkyl, $C_{1-4}$ alkoxy and $C_{1-4}$ haloalkoxy.

2. The compound, or an isotopically labeled compound thereof, or an optical isomer thereof, a tautomer thereof, or a pharmaceutically acceptable salt thereof according to claim 1, which is an isotopically labeled compound of the compound of formula (I), wherein all Hs are each independently and optionally replaced by D.

3. The compound, or an isotopically labeled compound thereof, or an optical isomer thereof, a tautomer thereof, or a pharmaceutically acceptable salt thereof according to claim 1, wherein L is C=O, O=S=O or $CH_2$.

4. The compound, or an isotopically labeled compound thereof, or an optical isomer thereof, a tautomer thereof, or a pharmaceutically acceptable salt thereof according to claim 1, wherein $R_{13}$ is H, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, or 11-15 membered tricyclic, and optionally substituted with 1, 2, 3 or 4 $R_1$(s).

5. The compound, or an isotopically labeled compound thereof, or an optical isomer thereof, a tautomer thereof, or a pharmaceutically acceptable salt thereof according to claim 1, wherein $R_{17}$ is H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, or 5-10 membered heteroaryl, and optionally substituted with 1, 2, 3 or 4 substitutes each independently selected from halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}$ alkyl$)_2$, —$N(C_{1-4}$ alkyl)(C(=O)$C_{1-4}$ alkyl), $C_{1-4}$ haloalkyl, $C_{1-4}$ alkoxy and $C_{1-4}$haloalkoxy.

6. The compound, or an isotopically labeled compound thereof, or an optical isomer thereof, a tautomer thereof, or a pharmaceutically acceptable salt thereof according to claim 1, wherein $R_{13}$ and $R_{17}$ form a 4-6 membered heterocycloalkyl with L and N atoms to which they are attached together, and the 4-6 membered heterocycloalkyl is optionally substituted with 1, 2, 3 or 4 substitutes each independently selected from halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}$ alkyl$)_2$, —$N(C_{1-4}$ alkyl)(C(=O)$C_{1-4}$ alkyl), $C_{1-4}$ haloalkyl, $C_{1-4}$ alkoxy and $C_{1-4}$ haloalkoxy.

7. The compound, or an isotopically labeled compound thereof, or an optical isomer thereof, a tautomer thereof, or a pharmaceutically acceptable salt thereof according to claim 1, wherein $R_{18}$ and $R_{19}$ are each independently selected from the group consisting of H, $C_{1-6}$ alkyl, $C_{1-4}$ haloalkyl, $C_{2-8}$ alkenyl, $C_{2-8}$ alkynyl, $C_{1-6}$ alkoxy, $C_{3-7}$ cycloalkyl, 4-14 membered heterocycloalkyl, $C_{6-10}$ aryl, and 5-10 membered heteroaryl, in which each option in the group is optionally substituted with 1, 2, 3 or 4 substitutes each independently selected from halogen, —$CF_3$, —OH, —$NH_2$, —$NH(CH_3)$, —$N(CH_3)_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}$ alkyl$)_2$, —$N(C_{1-4}$ alkyl)(C(=O)$C_{1-4}$ alkyl), $C_{1-4}$ haloalkyl, $C_{1-4}$ alkoxy and $C_{1-4}$haloalkoxy.

8. The compound, or an isotopically labeled compound thereof, or an optical isomer thereof, a tautomer thereof, or a pharmaceutically acceptable salt thereof according to claim 1, wherein $R_{18}$ and $R_{19}$ form $C_{3-6}$cycloalkyl or a 4-6 membered heterocycloalkyl with carbon atom to which they are attached together, and the $C_{3-6}$ cycloalkyl and 4-6 membered heterocycloalkyl are optionally substituted with 1, 2, or 3 substitutes each independently selected from halogen, —$CF_3$, —OH, —$NH_2$, —$NH(CH_3)$, —$N(CH_3)_2$, —CN, oxo, and $C_{1-4}$ alkyl.

9. The compound, or an isotopically labeled compound thereof, or an optical isomer thereof, a tautomer thereof, or a pharmaceutically acceptable salt thereof according to claim 1, wherein 1, 2 or 3 $R_2$(s) are present and each independently $R_2$ is selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, and 4-10 membered heterocycloalkyl, in which the —S—$C_{1-4}$ alkyl, $C_{1-6}$ alkyl, $C_{3-7}$ cycloalkyl, and 4-10 membered heterocycloalkyl are each optionally substituted with 1, 2 or 3 substituent(s) each independently selected from the group consisting of halogen, —OH, —$NH_2$, —NH($CH_3$), —$N(CH_3)_2$, —CN, $C_{1-4}$ alkyl, $C_{1-4}$ haloalkyl, $C_{1-4}$ alkoxy, and $C_{1-4}$ haloalkoxy.

10. The compound, or an isotopically labeled compound thereof, or an optical isomer thereof, a tautomer thereof, or a pharmaceutically acceptable salt thereof according to claim 1, wherein $R_{13}$ is substituted with 0 or 1 $R_1$, and $R_1$ is selected from halogen, —OH, $C_{1-6}$ alkyl, 5-7 membered heterocycloalkyl, and $C_{3-7}$ cycloalkyl, in which the $C_{1-6}$ alkyl is optionally substituted with 1, 2, or 3 $R_3$(s) and in which the 5-7 membered heterocycloalkyl, and $C_{3-7}$ cycloalkyl is optionally substituted with 1, 2, 3 or 4 $C_{1-3}$ alkyl.

11. The compound, or an isotopically labeled compound thereof, or an optical isomer thereof, a tautomer thereof, or a pharmaceutically acceptable salt thereof according to claim 1, wherein the compound is selected from a group consisting of:

N-((2-(6-(2-ethyl-5-fluoro-4-hydroxyphenyl)-1H-indazol-3-yl)-1H-imidazol-4-yl)methyl)-5-(piperidin-1-yl)pyrazine-2-carboxamide;

N-((2-(6-(2-ethyl-5-fluoro-4-hydroxyphenyl)-1H-indazol-3-yl)-1H-imidazol-4-yl) methyl)propionamide;

N-((2-(6-(2-ethyl-5-fluoro-4-hydroxyphenyl)-1H-indazol-3-yl)-1H-imidazol-4-yl)methyl)cyclopropanecarboxamide;

N-((2-(6-(2-ethyl-5-fluoro-4-hydroxyphenyl)-1H-indazol-3-yl)-1H-imidazol-4-yl)methyl)isobutyramide;

N-((2-(6-(2-ethyl-5-fluoro-4-hydroxyphenyl)-1H-indazol-3-yl)-1H-imidazol-4-yl)methyl)methanesulfonamide;

N-((2-(6-(2-ethyl-5-fluoro-4-hydroxyphenyl)-1H-indazol-3-yl)-1H-imidazol-4-yl)methyl)-5-morpholinopyrazine-2-carboxamide;

(S)-1-((2-(6-(2-ethyl-5-fluoro-4-hydroxyphenyl)-1H-indazol-3-yl)-1H-imidazol-4-yl)methyl)pyrrolidin-3-ol;

1-((2-(6-(2-ethyl-5-fluoro-4-hydroxyphenyl)-1H-indazol-3-yl)-1H-imidazol-4-yl)methyl)piperidin-4-ol;

N-((2-(6-(2-ethyl-5-fluoro-4-hydroxyphenyl)-1H-indazol-3-yl)-1H-imidazol-4-yl)methyl)-N-methylcyclopropanecarboxamide (Ex-10)

1-((2-(6-(2-ethyl-5-fluoro-4-hydroxyphenyl)-1H-indazol-3-yl)-1H-imidazol-4-yl)methyl)piperidine-4-nitrile;

1-((2-(6-(2-ethyl-5-fluoro-4-hydroxyphenyl)-1H-indazol-3-yl)-1H-imidazol-4-yl)methyl)pyrrolidine-3-carbonitrile;

5-ethyl-2-fluoro-4-(3-(4-(morpholinomethyl)-1H-imidazol-2-yl)-1H-indazol-6-yl)phenol;

5-ethyl-2-fluoro-4-(3-(4-((pyridin-3-ylamino) methyl)-1H-imidazol-2-yl)-1H-indazol-6-yl)phenol;

5-ethyl-2-fluoro-4-(3-(4-(((1-methyl-1H-pyrazol-4-yl)amino) methyl)-1H-imidazol-2-yl)-1H-indazol-6-yl)phenol;

3-((2-(6-(2-ethyl-5-fluoro-4-hydroxyphenyl)-1H-indazol-3-yl)-1H-imidazol-4-yl)methyl)-1-(2-hydroxyethyl)-1-methylurea;

4-(3-(4-(((cyclopropylmethyl)amino)methyl)-1H-imidazol-2-yl)-1H-indazol-6-yl)-5-ethyl-2-fluoro phenol;

N-((2-(6-(2-ethyl-5-fluoro-4-hydroxyphenyl)-1H-indazol-3-yl)-1H-imidazol-4-yl) methyl)cyclopropanesulfonamide;

N-((2-(6-(2-ethyl-5-fluoro-4-hydroxyphenyl)-1H-indazol-3-yl)-1H-imidazol-4-yl) methyl)ethanesulfonamide;

N-((2-(6-(2-ethyl-5-fluoro-4-hydroxyphenyl)-1H-indazol-3-yl)-1H-imidazol-4-yl)methyl)-4-hydroxypiperidine-1-carboxamide;

(R)—N-((2-(6-(2-ethyl-5-fluoro-4-hydroxyphenyl)-1H-indazol-3-yl)-1H-imidazol-4-yl)methyl)-3-hydroxy-N-methylpyrrolidine-1-carboxamide;

(R)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide;

(S)—N-((2-(6-(2-ethyl-5-fluoro-4-hydroxyphenyl)-1H-indazol-3-yl)-1H-imidazol-4-yl)methyl)-3-hydroxypyrrolidine-1-carboxamide;

5-ethyl-2-fluoro-4-(3-(4-(((2-hydroxyethyl)(methyl)amino)methyl)-1H-imidazol-2-yl)-1H-indazol-6-yl)phenol;

N-((2-(6-(2-ethyl-5-fluoro-4-hydroxyphenyl)-1H-indazol-3-yl)-1H-imidazol-4-yl)methyl)propane-2-sulfonamide;

methyl ((2-(6-(2-ethyl-5-fluoro-4-hydroxyphenyl)-1H-indazol-3-yl)-1H-imidazol-4-yl)methyl)carbamate;

2-cyanoethyl ((2-(6-(2-ethyl-5-fluoro-4-hydroxyphenyl)-1H-indazol-3-yl)-1H-imidazol-4-yl)methyl)carbamate;

N-((2-(6-(2-ethyl-5-fluoro-4-hydroxyphenyl)-1H-indazol-3-yl)-1H-imidazol-4-yl) methyl)cyclobutanecarboxamide;

N-((2-(6-(2-ethyl-5-fluoro-4-hydroxyphenyl)-1H-indazol-3-yl)-1H-imidazol-4-yl)methyl)-1-methylpyrrolidine-3-carboxamide;

4-(3-(4-((2-azabicyclo[2.2.2]octan-2-yl)methyl)-1H-imidazol-2-yl)-1H-indazol-6-yl)-5-ethyl-2-fluorophenol;

4-(3-(4-((cyclobutylamino)methyl)-1H-imidazol-2-yl)-1H-indazol-6-yl)-5-ethyl-2-fluorophenol;

5-ethyl-2-fluoro-4-(3-(4-(((tetrahydrofuran-3-yl)amino)methyl)-1H-imidazol-2-yl)-1H-indazol-6-yl)phenol;

5-ethyl-2-fluoro-4-(3-(4-((pyridin-2-ylamino)methyl)-1H-imidazol-2-yl)-1H-indazol-6-yl)phenol;

N-((2-(6-(2-ethyl-5-fluoro-4-hydroxyphenyl)-1H-indazol-3-yl)-1H-imidazol-4-yl)methyl)-1-methyl-1H-pyrazole-4-carboxamide;

5-ethyl-2-fluoro-4-(3-(4-(((1-methylpyrrolidin-3-yl)amino)methyl)-1H-imidazol-2-yl)-1H-indazole-6-yl)phenol;

N-((2-(6-(2-ethyl-5-fluoro-4-hydroxyphenyl)-1H-indazol-3-yl)-1H-imidazol-4-yl)methyl)morpholine-4-carboxamide;

N-((2-(6-(2-ethyl-5-fluoro-4-hydroxyphenyl)-1H-indazol-3-yl)-1H-imidazol-4-yl)methyl)-4-methylpiperazine-1-carboxamide; and 5-ethyl-4-(3-(4-((4-ethylpiperazin-1-yl)methyl)-1H-imidazol-2-yl)-1H-indazol-6-yl)-2-fluorophenol.

12. A pharmaceutical composition, comprising the compound, or an isotopically labeled compound thereof, or an optical isomer thereof, a tautomer thereof, or a pharmaceutically acceptable salt thereof according to claim 1, and one or more pharmaceutically acceptable carriers, adjuvants or excipients.

* * * * *